(12) United States Patent
Zhu et al.

(10) Patent No.: US 10,227,565 B2
(45) Date of Patent: *Mar. 12, 2019

(54) GENERATING HEPATOCYTES

(71) Applicants: The J. David Gladstone Institutes, a testamentary trust established under the Will of J. David Gladstone, San Francisco, CA (US); The Regents of the University of California, Oakland, CA (US)

(72) Inventors: Saiyong Zhu, San Francisco, CA (US); Sheng Ding, Orinda, CA (US); Holger Willenbring, San Francisco, CA (US); Milad Rezvani, San Francisco, CA (US); Jack Harbell, San Francisco, CA (US)

(73) Assignees: The J. David Gladstone Institutes, San Francisco, CA (US), A testamentary trust established under the Will of J. David Gladstone; The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/361,900

(22) Filed: Nov. 28, 2016

(65) Prior Publication Data
US 2017/0073636 A1  Mar. 16, 2017

Related U.S. Application Data

(62) Division of application No. 14/578,377, filed on Dec. 20, 2014, now Pat. No. 9,512,406.

(60) Provisional application No. 61/919,523, filed on Dec. 20, 2013.

(51) Int. Cl.

| | |
|---|---|
| *A61K 38/18* | (2006.01) |
| *C12N 5/071* | (2010.01) |
| *A61K 31/506* | (2006.01) |
| *A61K 31/661* | (2006.01) |
| *A61K 31/19* | (2006.01) |
| *A61K 31/135* | (2006.01) |
| *A61K 31/405* | (2006.01) |
| *A61K 31/4709* | (2006.01) |
| *A61K 31/573* | (2006.01) |
| *A61K 35/407* | (2015.01) |
| *A61K 45/06* | (2006.01) |

(52) U.S. Cl.
CPC ............ *C12N 5/067* (2013.01); *A61K 31/135* (2013.01); *A61K 31/19* (2013.01); *A61K 31/405* (2013.01); *A61K 31/4709* (2013.01); *A61K 31/506* (2013.01); *A61K 31/573* (2013.01); *A61K 31/661* (2013.01); *A61K 35/407* (2013.01); *A61K 38/18* (2013.01); *A61K 38/1808* (2013.01); *A61K 38/1825* (2013.01); *A61K 38/1833* (2013.01); *A61K 38/1875* (2013.01); *A61K 45/06* (2013.01); *C12N 2501/065* (2013.01); *C12N 2501/11* (2013.01); *C12N 2501/115* (2013.01); *C12N 2501/119* (2013.01); *C12N 2501/12* (2013.01); *C12N 2501/15* (2013.01); *C12N 2501/155* (2013.01); *C12N 2501/16* (2013.01); *C12N 2501/237* (2013.01); *C12N 2501/38* (2013.01); *C12N 2501/415* (2013.01); *C12N 2501/42* (2013.01); *C12N 2501/72* (2013.01); *C12N 2506/02* (2013.01); *C12N 2506/1307* (2013.01); *C12N 2506/45* (2013.01)

(58) Field of Classification Search
None
See application file for complete search history.

(56) References Cited

U.S. PATENT DOCUMENTS

| | | |
|---|---|---|
| 4,683,202 A | 7/1987 | Mullis |
| 5,284,835 A | 2/1994 | Lieber |
| 5,928,906 A | 7/1999 | Koster et al. |
| 6,506,574 B1 | 1/2003 | Rambhatla et al. |
| 7,256,042 B2 | 8/2007 | Rambhatla et al. |
| 7,645,610 B2 | 1/2010 | Sherley et al. |
| 7,989,204 B2 | 8/2011 | D'Amour |
| 8,062,632 B2 | 11/2011 | Lee et al. |
| 8,148,151 B2 | 4/2012 | Zhao et al. |
| 8,257,941 B2 | 9/2012 | Sakurada et al. |
| 8,404,481 B2 | 3/2013 | Sherley et al. |
| 8,410,085 B2 | 4/2013 | Moore et al. |
| 8,440,460 B2 | 5/2013 | Estrov et al. |
| 8,445,491 B2 | 5/2013 | Lum |

(Continued)

FOREIGN PATENT DOCUMENTS

| | | |
|---|---|---|
| WO | WO 2004067896 A2 | 10/2004 |
| WO | WO-2007127454 A2 | 11/2007 |

(Continued)

OTHER PUBLICATIONS

"U.S. Appl. No. 14/578,377, Notice of Allowance dated Jul. 28, 2016", 8 pgs.

(Continued)

*Primary Examiner* — Daniel C Gamett
(74) *Attorney, Agent, or Firm* — Schwegman Lundberg & Woessner, P.A.

(57) ABSTRACT

Compositions and methods are described herein for inducing reprogramming of non-pluripotent cells across lineage and differentiation boundaries to generate endodermal progenitor cells and hepatocytes. Compositions and methods for expansion of endodermal progenitor cells without loss of phenotype are also described herein.

19 Claims, 42 Drawing Sheets
(41 of 42 Drawing Sheet(s) Filed in Color)
Specification includes a Sequence Listing.

(56) References Cited

U.S. PATENT DOCUMENTS

| | | | |
|---|---|---|---|
| 8,481,317 | B2 | 7/2013 | Yu et al. |
| 9,284,531 | B2 | 3/2016 | Stachelscheid et al. |
| 9,284,576 | B2 | 3/2016 | Vallier et al. |
| 9,512,406 | B2 | 12/2016 | Zhu et al. |
| 2006/0154235 | A1 | 7/2006 | Ochiya et al. |
| 2006/0251642 | A1 | 11/2006 | Wolffe et al. |
| 2010/0086999 | A1 | 4/2010 | Zhao et al. |
| 2010/0233804 | A1 | 9/2010 | Zhou et al. |
| 2010/0331281 | A1 | 12/2010 | Moore et al. |
| 2011/0110899 | A1 | 5/2011 | Shi et al. |
| 2011/0275157 | A1 | 11/2011 | You et al. |
| 2011/0280844 | A1 | 11/2011 | Yu et al. |
| 2012/0028351 | A1 | 2/2012 | Li et al. |
| 2012/0183989 | A1 | 7/2012 | Matsui et al. |
| 2013/0059385 | A1 | 3/2013 | Li et al. |
| 2013/0095567 | A1 | 4/2013 | Brolen et al. |
| 2015/0175962 | A1 | 6/2015 | Zhu et al. |

FOREIGN PATENT DOCUMENTS

| | | |
|---|---|---|
| WO | WO-2010014949 A2 | 2/2010 |
| WO | WO-2010050626 A1 | 5/2010 |
| WO | WO-2011050476 A1 | 5/2011 |
| WO | WO-2011109015 A1 | 9/2011 |

OTHER PUBLICATIONS

"U.S. Appl. No. 14/578,377, Response filed Mar. 3, 2016 to Restriction Requirement dated Jan. 7, 2016", 9 pgs.

"U.S. Appl. No. 14/578,377, Response filed Jun. 17, 2016 to Restriction Requirement dated Mar. 21, 2016", 8 pgs.

"U.S. Appl. No. 14/578,377, Restriction Requirement dated Jan. 7, 2016", 11 pgs.

"U.S. Appl. No. 14/578,377, Restriction Requirement dated Mar. 21, 2016", 9 pgs.

Efe, Jem A., et al., "Development unchained: how cellular reprogramming is redefining our view of cell fate and identity", Science Progress 94(3), (2011), 298-322.

Gramignoli, Roberto, et al., "New potential cell source for hepatocyte transplantation: Discarded livers from metabolic disease liver transplants", Stem Cell Research, 11, (2013), 563-573.

Li, Fuming, et al., "Combined activin A/LiCl/Noggin treatment improves production of mouse embryonic stem cell-derived definitive endoderm cells", J. Cell Biochem., 112(4), (2011), 1022-1034.

Li, Wenlin, et al., "Rapid induction and long-term self-renewal of primative neural precursors from human embryonic stem cells by small molecule inhibitors", Proc. Natl. Acad. Sci. USA, 108(20), (2011), 8299-8304.

Ma, X., et al., "Highly efficient differentiation functional hepatocytes from human induced pluripotent stem cells", Stem Cells Transl. Med., 2(6), (2013), 409-419.

Puppi, Juliana, et al., "Improving the Techniques for Human Hepatocyte Transplantation: Report From a Consensus Meeting in London", Cell Transplantation, 21(1), (2012), 1-10.

Rashid, S. Tamir, et al., "Modeling inherited metabolic disorders of the liver using human induced pluripotent stem cells", J. Clin. Invest., 120(9), (2010), 3127-3136.

Seiffert, Dietmar, et al., "Presenilin-1 and -2 Are Molecular Targets for y-Secretase Inhibtors", J. Bio. Chem., 275(44), (2000), 34086-34091.

Si-Tayeb, Karim, et al., "Highly Efficient Generation of Human Heaptocyte-Like Cells from Induced Pluripotent Stem Cells", Hepatology, 51(1), (2010), 297-305.

Wang, Jing, et al., "Novel Histone Demethylase LSD1 Inhibitors Selectively Target Cancer Cells with Pluripotent Stem Cells Properties", Cancer Res., 71(23), (2011), 7238-7249.

Warren, Luigi, et al., "Highly efficient reprogramming to pluripotency and directed differentiation of human cells with synthetic modified mRNA", Cell Stem Cell, 7(5), (2010), 618-630.

Zhu, S., et al., "Mouse liver repopulation with hepatocytes generated from human fibroblasts", Nature, 508, (2014), 93-97.

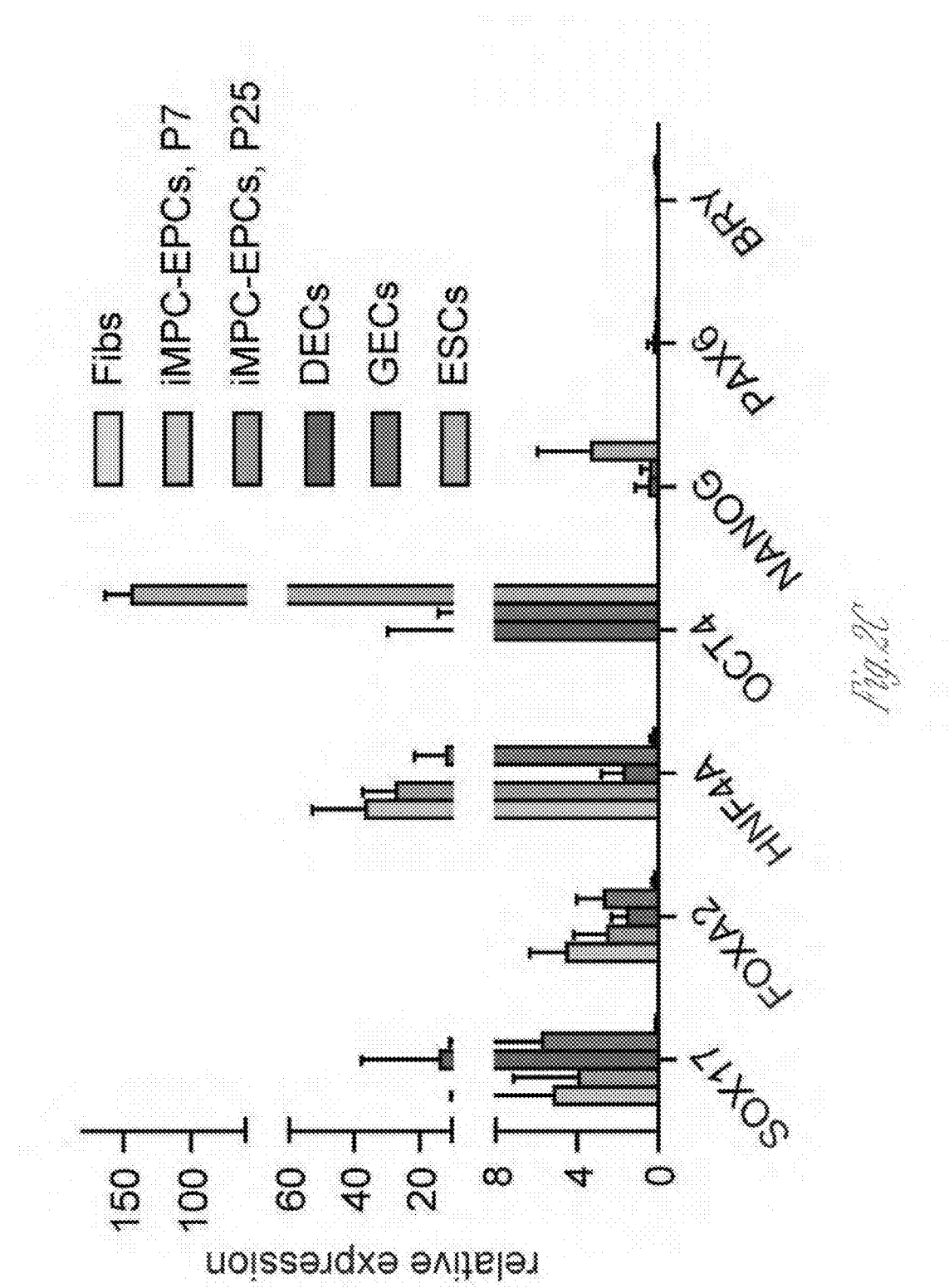

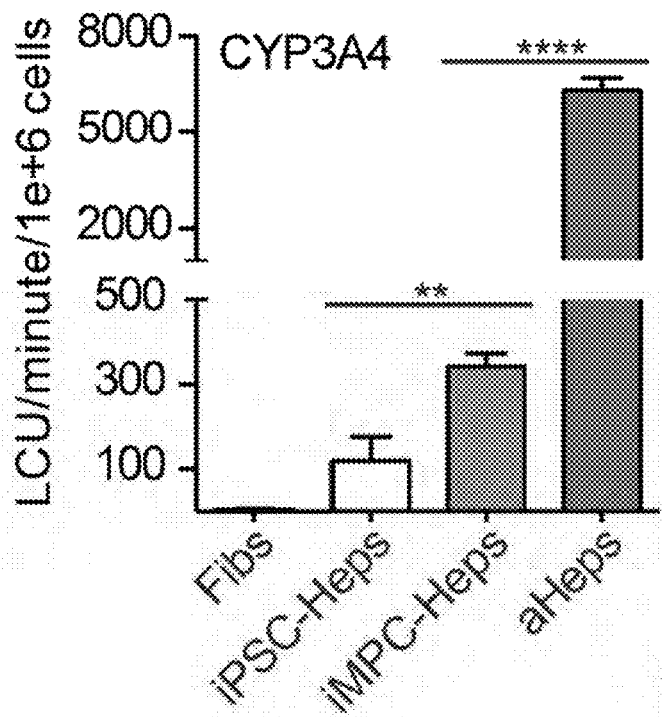
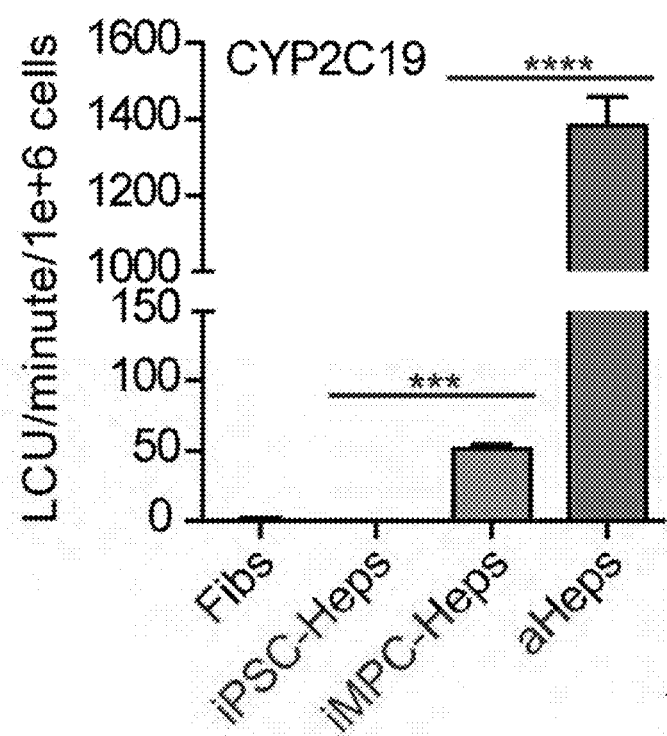

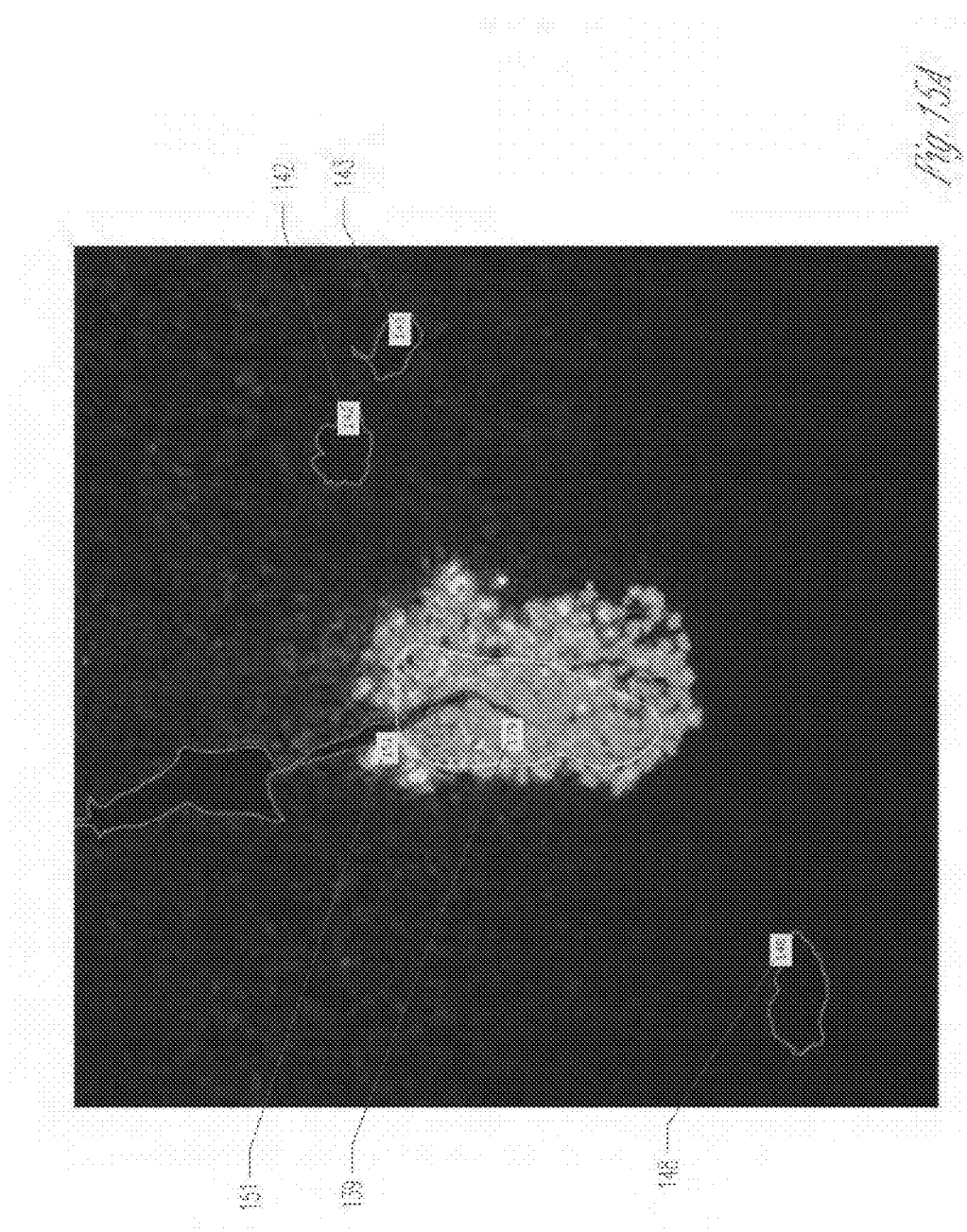

RESPONSE TO XENOBIOTICS

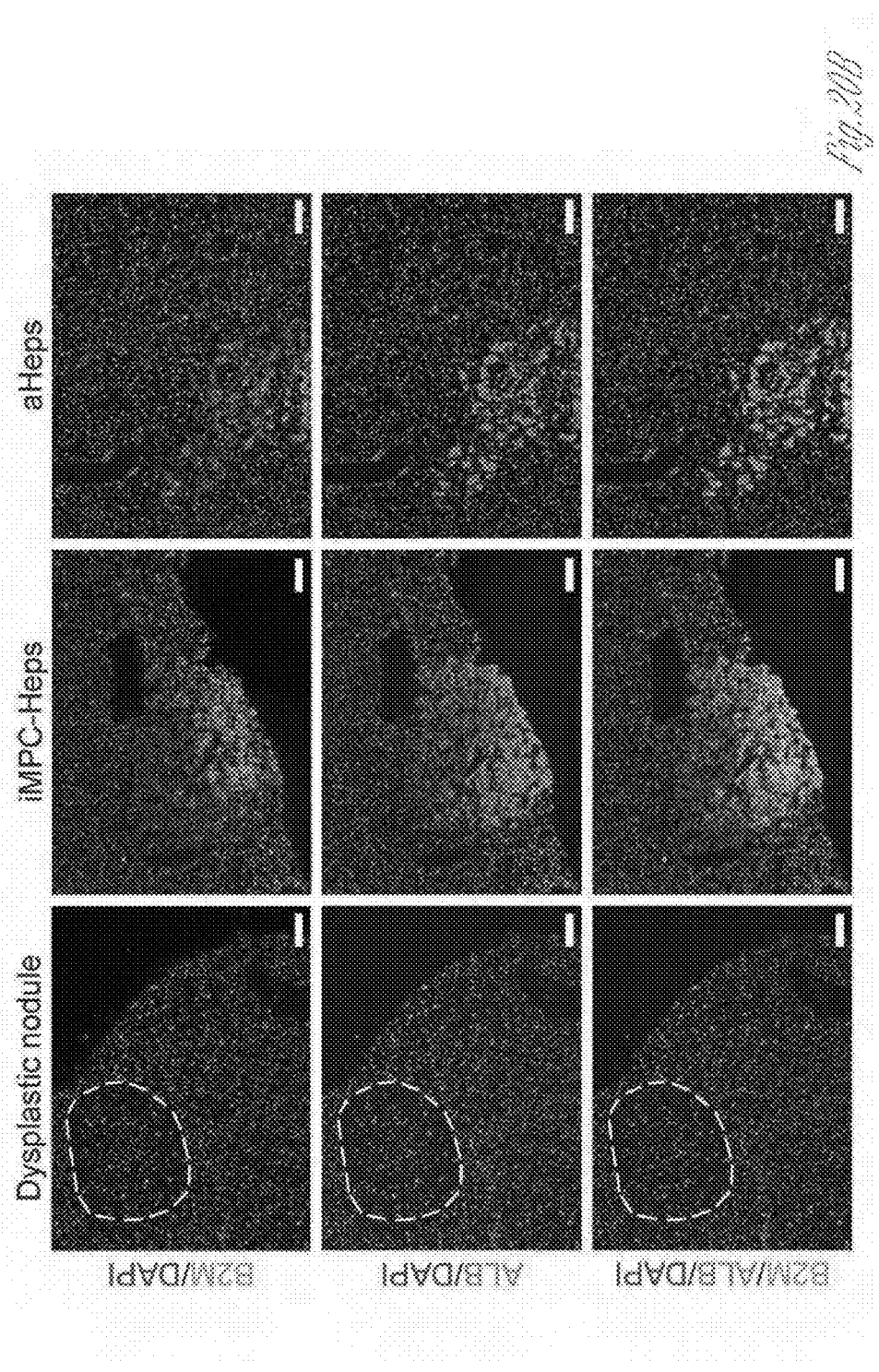

GENERATING HEPATOCYTES

CLAIM OF PRIORITY

This application is a divisional application of U.S. application Ser. No. 14/578,377, filed Dec. 2, 2014, which application, claims benefit of priority to the filing date of U.S. Provisional Application Ser. No. 61/919,523, filed Dec. 20, 2013, the contents of which, are specifically incorporated herein by reference in their entity.

BACKGROUND

Human induced pluripotent stem cells (iPSCs) are thought to have the potential to revolutionize research and therapy of liver diseases by providing a source of hepatocytes for autologous cell therapy and disease modeling. Progress has been made in advancing the differentiation of iPSCs into hepatocytes (iPSC-Heps) in vitro (see, e.g., Si-Tayeb et al., HEPATOLOGY 51: 297-305 (2010); Rashid et al., J CLIN INVEST 120: 3127-3136 (2010); Ma et al., STEM CELLS TRANSL MED (2013)). However, cells that replicate the ability of human primary adult hepatocytes (aHeps) to proliferate extensively in vivo have not been reported. This deficiency has not only hampered efforts to recreate human liver diseases in mice, it has also cast doubt on the potential of iPSC-Heps for liver cell therapy. Significant problems remain that include the need for extensive post-transplant expansion to establish and sustain a therapeutically effective liver cell mass in patients, a lesson learned from clinical trials of adult hepatocyte transplantation (see, e.g., Puppi et al., CELL TRANSPLANT 21: 1-10 (2012)).

SUMMARY

The methods and compositions solve the problems of efficient reprogramming of differentiated cells into hepatocytes that can be extensively expanded into quantities useful for therapeutic treatment of liver conditions and diseases. As described herein, human endodermal progenitor cells and immature hepatocytes capable of extensive proliferation can be generated from differentiated cells. Such an expanded population of cells can significantly repopulate mammalian liver tissues in vivo. Unlike current protocols for deriving hepatocytes from human fibroblasts, iPSCs were not generated as a step in the production of hepatocytes. Instead, a shortcut reprogramming process was used to generate induced multipotent progenitor cells (iMPC) from which endoderm progenitor cells (iMPC-EPCs) and subsequently hepatocytes (iMPC-Heps) were efficiently differentiated.

Compositions containing combinations of small molecules were employed that aided endoderm fate choice and hepatocyte differentiation without compromising proliferation. After transplantation into an immune-deficient mouse model of human liver failure, hepatocytes generated from induced multipotent progenitor cells were able to engraft and proliferate, and the engrafted cells acquired levels of hepatocyte function similar to adult hepatocytes. Unfractionated hepatocytes generated from induced multipotent progenitor cells did not form tumors, most likely because they never entered a pluripotent state. This represents, to our knowledge, the first demonstration of significant liver repopulation of mice with hepatocytes generated in vitro, which removes a long-standing roadblock on the path to autologous liver cell therapy.

Compositions described herein include those containing an epidermal growth factor (EGF), basic fibroblast growth factor (bFGF), an activator of WNT signaling (e.g., a GSK3 inhibitor), a nuclear receptor liver receptor homolog 1 agonist, a histone deacetylase (HDAC) inhibitor, a histone demethylase LSD1 inhibitor, a DNA methyltransferase (DNMT) inhibitor, or a combination thereof. Also described herein are methods that involve administering such a composition to a cell, and/or incubating a cell in such a composition. The cell can be a nonpluripotent cell, a somatic cell, an adult cell, a multipotent cell, a unipotent cell, a progenitor cell, a newborn cord blood cell, a newborn (non-pluripotent) stem cell, an allogenic cell, an autologous cell, a heterogeneous mixture of cells, a homogeneous mixture of cells, or any combination thereof. In some cases a population of cells is incubated in the composition, After several days the cells can be incubated in such a reprogramming composition that does not contain epidermal growth factor (EGF) or basic fibroblast growth factor (bFGF), but does contain Activin A.

Such compositions and methods generate cells that express endodermal cell markers, which can be expanded using the expansion compositions and methods described herein. The cells can be employed for treatment of liver conditions and/or diseases, for example, after expansion, into a population of cells.

DESCRIPTION OF THE FIGURES

The patent or application file contains at least one drawing executed in color. Copies of this patent or patent application publication with color drawing(s) will be provided by the Office upon request and payment of the necessary fee.

FIG. 1A is a schematic showing an example of stepwise method for generation of iMPC-Heps. Reprogramming of newborn fibroblasts (Fibs) to endoderm was initiated in medium containing the small molecules CHIR9902 (CHIR, a WNT activator/GSK3 inhibitor), dilauroyl phosphatidylcholine (DLPC; a nuclear receptor liver receptor homolog 1 agonist), sodium butyrate (NaB; a histone deacetylase (HDAC) inhibitor, parnate (Par; a histone demethylase LSD1 inhibitor), and RG108 (RG; a DNA methyltransferase (DNMT) inhibitor), and the growth factors EGF and bFGF. For reprogramming, medium containing CHIR, DLPC, NaB, Par, RG, and Activin A was used, yielding colonies of iMPC-endoderm progenitor cells (EPCs) between days 21-28. Individual iMPC-EPC colonies were expanded in medium containing EGF, bFGF, CHIR, and A83 (a TGF-β inhibitor). For hepatocyte specification, medium containing bFGF, A83, BMP4, Dexamethasone, HGF, oncostatin M (OSM), and compound E was used. FIG. 1B illustrates that the procedures described herein reprogram fibroblasts to express SOX17 as detected by qRT-PCR (SOX17 is a marker for endoderm progenitor cells). FIG. 1C also illustrates that the endoderm-specific gene FOXA2 is expressed during the reprogramming process relative to starting cells at day 0. FIG. 1D shows that SOX17 and FOXA2, as well as the pluripotency-specific markers OCT4 and NANOG are not detected in the starting cells (newborn fibroblasts) as detected by immunostaining. Scale bars=100 μm, FIG. 1E shows co-expression of SOX17 and FOXA2 in colonies at day 28 of the reprogramming protocol. Scale bars=100 μm.

FIG. 2A-2D illustrates the characteristics of iMPC-EPCs generated from fibroblasts. FIG. 2A shows bright field (BF) photomicrographs illustrating the morphology of iMPC- EPCs at passage 25. Immunostainings show that these cells express FOXA2, SOX17, and HNF4α. Scale bar=100 μm. FIG. 2B illustrates the expansion capacity of iMPC-EPCs as compared to fibroblasts. Cell numbers were counted at indicated time points. Error bars represent SEM of technical replicates (n=3). FIG. 2C illustrates the relative expression (as detected by qRT-PCR) of genes specific for pluripotency, endoderm, ectoderm, or mesoderm in iMPC-EPCs as compared to fibroblasts, embryonic stem cells (ESCs), and definitive endoderm cells (DECs) or primitive gut-tube endoderm cells (GECs) derived from ESCs. Gene expression levels are shown relative to fibroblasts. Error bars represent SEM of technical replicates (n=3). The expression levels (bars) from left to right are for: fibroblasts (leftmost bar, almost no expression), iMPC-EPCs (passage 7), iMPC-EPCs (passage 25), definitive endoderm cells (DECs), primitive gut-tube endoderm cells (GECs), and embryonic stem cells (ESCs; rightmost bar). FIG. 2D illustrates that small molecules enhance the efficiency of reprogramming to the endodermal lineage. The small molecules tested included combinations of CHIR99021 (CH), dilauroyl phosphatidylcholine (DLPC), sodium butyrate (NaB), parnate (Par), and RG108 (RG). The number of colonies exhibiting positive immunostaining for FOXA2 was counted at day 28 of the reprogramming step of the protocol. Medium containing Activin A was additionally supplemented with the indicated small molecules.

FIG. 3A-3J illustrate the characteristics of iMPC-Heps generated from iMPC-EPCs. FIG. 3A shows a bright-field (BF) photomicrograph illustrating the morphology of iMPC-Heps. Immunostainings illustrate expression of HNF4α. ALB. AAT, and CK18. Scale bars=100 μm. FIG. 3B illustrates the distribution of albumin (ALB), HNF4α, and CK18 expression in iMPC-Heps as detected by flow cytometry. As shown, the majority of iMPC-Heps express ALB. HNF4α, and CK18. FIG. 3C graphically illustrates the relative expression levels of hepatocyte-specific gene expression in iMPC-Heps relative to fetal hepatocytes (fHeps) as detected by qRT-PCR. CYP1A1 and CYP3A7, genes specific for immature hepatocytes, were expressed at similar levels in iMPC-Heps and fHeps, iMPC-Heps also express the mature hepatocyte-specific CYP450 genes CYP2B6/2C9/2C19/3A4 at similar levels, but not CYP1A2/2D6, Error bars represent SEM of technical replicates (n=3). FIG. 3D illustrates significant ALB secretion by iMPC-Heps as detected by enzyme-linked immunosorbent assay (ELISA) compared to newborn fibroblasts (Fibs), hepatocytes generated from induced pluripotent stem cells (iPSC-Heps), and adult hepatocytes (aHeps). Error bars represent SEM of biological replicates (i=3), t test, $P<0.01$. FIG. 3E graphically illustrates CYP3A expression in iMPC-Heps, Fibs, iPSC-Heps, and aHeps. The assay selectivity was: CYP3A5≥CYP3A7>CYP3A4. FIG. 3F graphically illustrates CYP3A4 expression in iMPC-Heps, Fibs, iPSC-Heps, and aHeps. FIG. 3G graphically illustrates CYP2C19 expression in iMPC-Heps, Fibs, iPSC-Heps, and aHeps. As shown in FIGS. 3E-3G, the CYP3A, CYP3A4, and CYP2C19 genes are expressed at higher levels in iMPC-Heps than in iPSC-Heps. The expression of these genes in Fibs and aHeps was used as negative and positive controls, respectively. Error bars represent SEM of biological replicates (n=3), t test, $P<0.01$, *$P<0.001$, *$P<0.0001$. FIG. 3H illustrates that expression of the pluripotency-specific genes OCT4 and NANOG was not detectable even at the earliest stages of the reprogramming process. FIG. 3I illustrates proportions of cells that express TRA-1-60 subjected to the methods described herein (top panels) compared to untreated embryonic stem cells (bottom panels) as detected by cell sorting. FIG. 3J shows proportions of cells that express NANOG and/or TRA-1-60 positive cells at the end of the reprogramming process as detected by flow cytometry. As illustrated, NANOG and TRA-1-60 expression was essentially absent at all stages of the reprogramming process (FIG. 4H-4J).

FIG. 4A-4J illustrates post-transplant proliferation and maturation of iMPC-Heps. FIG. 4A graphically illustrates human serum albumin (HSA) levels in recipients of iMPC-Heps or adult hepatocytes (aHeps). Stars indicate time when mice were killed for analysis. Arrow marks fatality. FIG. 4B illustrates co-expression of human-specific albumin (ALB) and Ki67 in proliferating iMPC-Heps at the periphery of a repopulating nodule (arrowheads). Scale bar=100 μm. FIG. 4C illustrates global gene expression profiling as detected by microarray analysis, showing a close resemblance between iMPC-Heps and aHeps in vivo, but differences between iMPC-Heps and freshly isolated aHeps in vitro. The global gene expression profile of freshly isolated aHeps is similar to that of aHeps and iMPC-Heps in vivo. Expression levels of most, but not all, genes were similar between iMPC-Heps and iPSC-Heps in vitro. For heatmap generation, genes with expression, levels below background (log 2 normalized expression <3) and genes not varying over all samples (standard deviation expression <1) were filtered out. The remaining 1,299 genes and all samples were hierarchically clustered using the helust function in R v2.15.1. FIG. 4D shows expression of CYP genes and ALB and AFP in iMPC-Heps in vivo relative to aHeps in vivo as detected by qRT-PCR analysis. FIG. 4E shows LC/MS/MS analysis of human-specific CYP2D6-mediated metabolism of debrisoquine (DB) in mice repopulated with iMPC-Heps or aHeps. Plasma levels of debrisoquine and its metabolite 4-hydroxydebrisoquine (4-OH-DB) peaked 1 hour after gavage. Molar 4-hydroxydebrisoquine/debrisoquine ratios at 1 hour are shown, calculated as the mean of the ratios for repeat injections (n=3). Error bars represent analytical SEM, t test, **$P<0.01$. FIG. 4F illustrates co-expression of human-specific ALB and mouse-specific Alb, which rules out fusion of iMPC-Heps and mouse hepatocytes. Scale bars=100 μm. FIG. 4G is a schematic diagram showing the timing of iMPC-EPC reprogramming. FIG. 4H illustrates FOXA2 and NANOG expression in iMPC-EPC colonies as function of time after initiation of reprogramming. FIG. 4I shows representative immunostainings illustrating FOXA2-positive colonies emerging at day 16 of the reprogramming process and absence of NANOG-positive colonies or cells at all time points. Scale bars=100 μm. FIG. 4J shows a gradual, increase in the number of FOXA2-positive cells beginning at day 16 of the reprogramming process, whereas NANOG-positive cells are absent at all time points, as detected by flow cytometry. Newborn fibroblast (Fibs), embryonic stem cells (ESCs), and induced multipotent endodermal progenitor cells (iMPC-EPCs) were used as controls. At least 10,000 events were collected.

FIG. 5A-SC illustrates reprogramming of Fibs into iMPC-EPCs occurs earlier and is more efficient than reprogramming into iPSCs. FIG. 5A is a schematic diagram showing the duration of doxycycline (Dox) treatment and time allowed for reprogramming to occur until analysis.

FIG. 6A shows increased expansion of colonies reprogrammed to endoderm fate in medium containing CHIR99021 (CHIR) and A83. As shown, CHIR99021 (CHIR) and A83 promote colony expansion. Scale bars=100 µm. FIG. 6B graphically illustrates the number of colonies formed in media supplemented with various agents. As shown, supplementation with EGF and bFGF further increases the number of colonies by passage 3-4.

FIG. 9A shows that iMPC-EPCs acquire AFP expression after exposure to bFGF and BMP4 for 4 days as detected by immunostaining. FIG. 9B shows that iMPC-EPCs acquire PDX1 expression after exposure to retinoic acid, GDC-0449 (Sonic Hedgehog inhibitor), and LDN-193189 (BMP inhibitor) for 4 days, as detected by immunostaining. Scale bars=100 tan.

FIG. 12A shows that iMPC-Heps contain glycogen as detected by Periodic acid-Schiff (PAS) staining. Adding the Dil-acetylated low-density lipoprotein (Dil-ac-LDL) fluorescent substrate to the culture medium shows that iMPCHeps take up LDL. Incubation with BODIPY 493/503 or staining with Oil-red-O (ORO) shows that the iMPC-Heps store lipids. Newborn fibroblasts (Fibs) were used as negative controls. Scale bars=100 µm. FIG. 12B shows that iMPC-Heps produce urea. Fibs were used as negative control. FIG. 12C shows that when compared to iPSC-Heps generated using current standard protocols, iMPC-Heps exhibit lower expression of AFP, and increased expression of several hepatocyte-specific genes including ALI and SERPINA1. Gene expression of many CYP450 enzymes is also higher in iMPC-Heps than in iPSC-Heps, indicating that iMPC-Heps have a more mature hepatocyte phenotype than iPSC-Heps. Gene expression levels in iPSC-Heps were set to 1. Error bars represent SEM of technical replicates (n=3).

FIG. 13A-13D show that iMPC-Heps secrete more ALB (FIG. 13A) and have higher CYP3A family (FIG. 13B), CYP3A4 (FIG. 13C), and CYP2C19 (FIG. 131)) activities than iPSC-Heps generated with the iMPC-EPC/Hep generation protocol Results were calculated as the mean of biological replicates (n=3). Error bars represent analytical SEM, t test, *P<0.05, **P<0.01.

FIG. 14A shows a small (left) and a large (right) nodule of iMPC-Heps that express ALB at 3 (left) and 9 (right) months after transplantation, respectively. Scale bars=100 µm. FIG. 14B shows multiple large nodules of iMPC-Heps identified by FAH immunostaining at 9 months after transplantation. Scale bar=100 µm. FIG. 14C graphically illustrates the size distribution of nodules of iMPC-Heps 9 months after transplantation based on ALB and FAH immunostaining.

FIG. 15A-15B shows repopulating nodules isolated by laser capture microdissection (LCM). FIG. 15A shows an example of a repopulating nodule identified by immunostaining for human-specific ALB. Blood vessels were used as additional markers of the location of a nodule in an adjacent, unfixed cryosection. FIG. 15B illustrates successful isolation of a repopulating nodule as confirmed by ALB immunostaining after LCM. The middle image shows a cryosection fixed and immunostained for ALB after LCM to confirm specific isolation of a repopulating nodule. The left and right images show ALB immunostainings of cryosections flanking the cryosection used for LCM. Scale bars=100 µm.

FIG. 18A-18B illustrates mature hepatocyte-specific marker (CYP3A4 and CYP2D6) expression patterns in iMPC-Heps matured in vivo versus adult hepatocytes (aHeps) as detected by immunostaining. FIG. 18A shows iMPC-Heps and aHeps co-immunostained for ALB and CYP3A4. FIG. 18B shows iMPC-Heps and aHeps co-immunostained for ALB and CYP2D6. Of note, the CYP450 antibodies detect the mouse homologues of CYP3A4 and CYP2D6, which, as in humans, appear to be expressed in hepatocytes, but not in nonparenchymal cells. Scale bars=100 µm.

FIG. 19A shows a Kaplan-Meier survival curve illustrating that $1\times10^6$ transplanted iMPC-Heps, iPSC/ESC-Heps, and aHeps are not effective in rescuing mice from death from acute liver failure. Logrank test (Mantel-Cox test) P=0.4426 between iMPC-Heps and iPSC/ESC-Heps, P=0.4031 between iMPC-Heps and aHeps. FIG. 19B shows a Kaplan-Meier survival curve illustrating that the efficacy of $1\times10^6$ transplanted aHeps is similar to the efficacy of 1×10⁶ transplanted iMPCHeps, but that iPSC/ESC-Heps were not effective in preventing death in mice suffering from chronic liver failure. Logrank test (Mantel-Cox test) P<0.01 between iMPC-Heps and iPSC/ESC-Heps, P=0.9501 between iMPC-Heps and aHeps. The number of mice in each group is shown in parentheses.

FIG. 20A-20B illustrates expression patterns in iMPC-Heps or aHeps dysplastic nodules of mouse origin. FIG. 20A shows a dysplastic nodule in an FRG mouse transplanted with iMPC-Heps after H&E staining. Scale bar=100 μm. FIG. 20B shows expression of B2M and ALB after co-immunostaining dysplastic nodules with human-specific anti-B2M and anti-ALB antibodies. As shown, the cells within the dysplastic nodules are negative for both markers and therefore of mouse origin. Scale bars=100 μm. Nodules of aHeps are shown as controls.

DETAILED DESCRIPTION

Figure 1A:
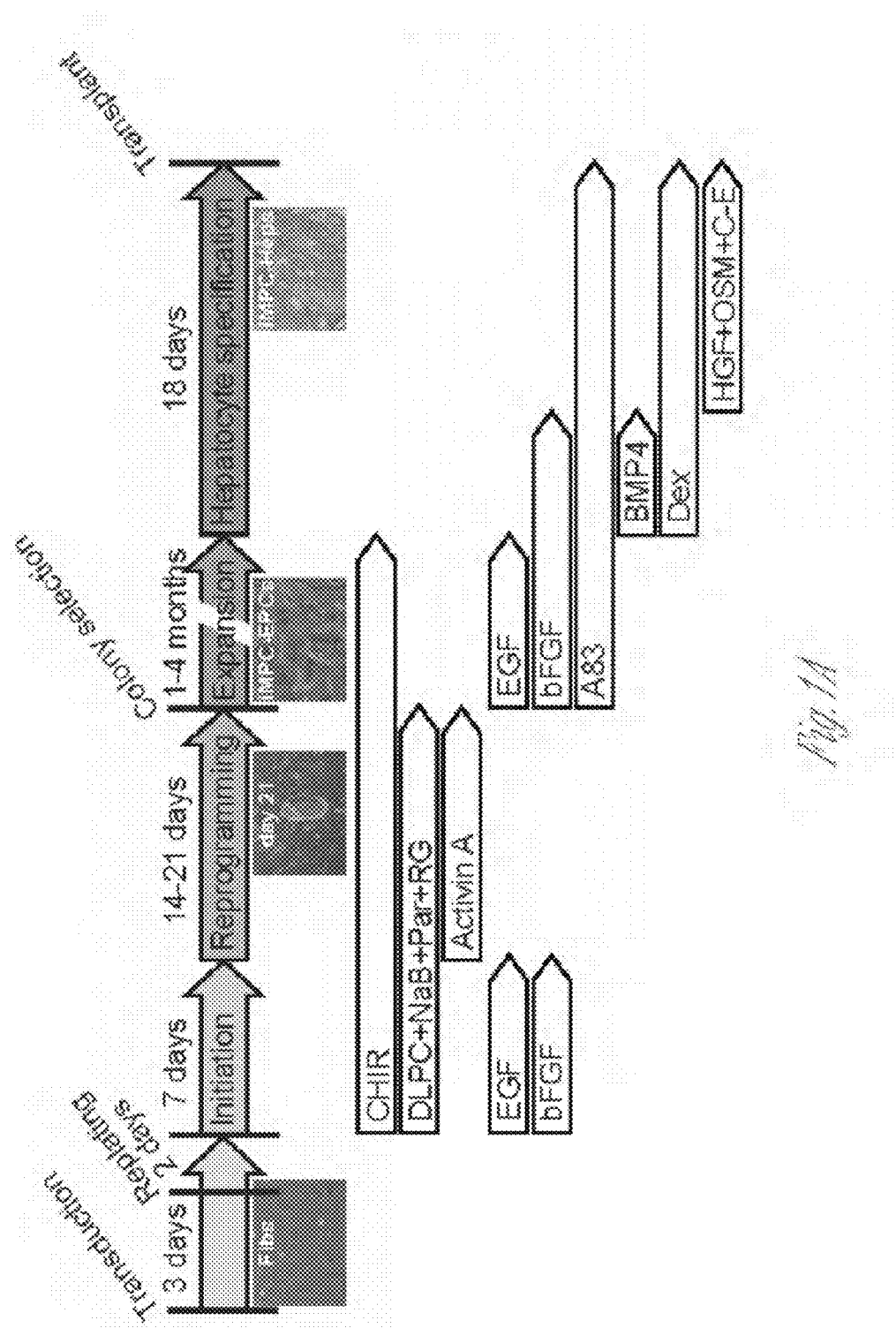
FIG. 1A-1E illustrates the process for generating induced multipotent progenitor cells (iMPCs), expansion of iMPCs, and maturation of hepatocytes from starter cells (e.g., newborn fibroblasts).

The methods and compositions described herein can efficiently generate hepatocytes that can extensively proliferate. The hepatocytes can be generated from differentiated cells by passage through an induced multipotent progenitor stage rather than an induced pluripotent stage. The methods can include inducing multipotency in one or more mammalian cells and inducing multipotent cells to differentiate into the endodermal lineage, Compositions useful for forming endodermal progenitor cells include those containing an epidermal growth factor (EGF), basic fibroblast growth factor (bFGF), an activator of WNT signaling (e.g., a GSK3 inhibitor), a nuclear receptor liver receptor homolog 1 agonist, a histone deacetylase (HDAC) inhibitor, a histone demethylase LSD inhibitor, a DNA methyltransferase (DNMT) inhibitor, or a combination thereof. After several days the cells are incubated in such a reprogramming composition that does not contain epidermal growth factor (EGF) or basic fibroblast growth factor (bFGF), but does contain Activin A. Such compositions and methods generate cells that express endodermal cell markers, which can be expanded using the expansion compositions and methods described herein.

To generate hepatocytes, the multipotent endodermal progenitor cells can be contacted with a differentiation composition that can contain bone morphogenetic protein 4 (BMP4), basic fibroblast growth factor (bFGF), one or more TGFβ inhibitors, hepatocyte growth factor (HGF), dexamethasone (Dex), oncostatin M (OSM), compound E, or any combination thereof.

Endodermal Progenitor Cells Endodermal progenitor cells can be generated from a variety of starting cells, for example, by inducing multipotency as described herein. The starting cells can be, but need not be, pluripotent stem cells. Multipotency can be induced by expression of pluripotency factors (e.g., OCT4, SOX2, KLF4, and combinations thereof) in a differentiated cell, without induction of full pluripotency in the cells. Reprogramming to the endodermal lineage can be induced at the same time as, or after, expression of the pluripotency factors. Reprogramming to the endodermal lineage can involve incubating the starting cells in a composition containing epidermal growth factor (EGF), basic fibroblast growth factor (bFGF), an activator of WNT signaling (e.g., a GSK3 inhibitor), a nuclear receptor liver receptor homolog 1 agonist (e.g., dilauroyl phosphatidylcholine (DLPC)), a histone deacetylase (HDAC) inhibitor (e.g., sodium butyrate), a histone demethylase LSD1 inhibitor (e.g., parnate), a DNA methyltransferase (DNMT) inhibitor (e.g., RG108), or a combination thereof for a time and at concentrations sufficient to stimulate expression of one or more endodermal marker genes in the cells. The composition for reprogramming cells into the endoderm lineage can include two or more of an epidermal growth factor (EGF), a basic fibroblast growth factor (bFGF), an activator of WNT signaling, a nuclear receptor liver receptor homolog 1 agonist, a histone deacetylase (HDAC) inhibitor, a histone demethylase LSD1 inhibitor, and/or a DNA methyltransferase (DNMT) inhibitor. In some embodiments, the composition for reprogramming differentiated cells into the endoderm lineage can include three or more, or four or more, or five or more, or six or more, of an epidermal growth factor (EGF), a basic fibroblast growth factor (bFGF), an activator of WNT signaling, a nuclear receptor liver receptor homolog 1 agonist, a histone deacetylase (HDAC) inhibitor, a histone demethylase LSD1 inhibitor, and/or a DNA methyltransferase (DNMT) inhibitor.

Starting cells that express pluripotency factors (e.g., OCT4, SOX2, KLF4, and combinations thereof) can become induced multipotent cells. Such induced multipotent cells can be induced to become endodermal progenitor cells by incubation in such an endodermal reprogramming medium for about 2 to 14 days, or about 3 to 12 days, or about 4 to 10 days, or about 5 to 9 days, or about 6 to 8 days (for example, about 7 days). The cells can then be incubated in such a composition without the epidermal growth factor (EGF), and the basic fibroblast growth factor (bFGF), but with Activin A. After about 15 to 35 days, or about 17 to 33 days, or about 19 to 31 days, or about 20 to 30 days the cells express endodermal markers. Such endodermal markers include, for example, Sox17, Foxa2, Ceeberus 1 (Cer), C—X—C chemokine receptor type 4 (Cxcr4), or a combination thereof. Such compositions and methods generate a population of cells that include endodermal cells.

Cells can express pluripotency factors before or during incubation in such a reprogramming composition. Methods for expression of pluripotency factors in cells are available to those of skill in the art, and examples of such methods are described herein below.

Growth Factors

The endodermal reprogramming composition can contain epidermal growth factor and basic fibroblast growth factor.

Epidermal growth factor can stimulate cell growth, cell proliferation, and cellular differentiation. Human epidermal growth factor is a small protein (approximately 6045 daltons) with about 53 amino acids and three intramolecular disulfide bonds. Epidermal growth factor is available commercially, for example, from MP Biomedicals (see, e.g., mpbio.com), PeproTech (see, e.g., peprotech.com), and Cell Signaling Technology (see, e.g., cellsignal.com).

Basic fibroblast growth factor can help maintain cells in an undifferentiated state. Basic fibroblast growth factor is commercially available, for example, from BD Biosciences (see, e.g., bdbiosciences.com), and EMD Millipore (see, e.g., Millipore.com).

As illustrated herein epidermal growth factor and basic fibroblast growth factor can facilitate reprogramming of differentiated cells to the endoderm lineage. Experiments described herein show that addition of epidermal growth factor and basic fibroblast growth factor to a selected population of cells during or after expression of pluripotency factors can increase the proportion and yield of cells that express endoderm markers. In particular, addition of epidermal growth factor and basic fibroblast growth factor to cells induces those cells to express markers indicative of a endoderm phenotype such as Sox17, Foxa2, Cerberus 1 (Cer), C—X—C chemokine receptor type 4 (Cxcr4), or a combination thereof. For example, after treatment of a selected population of cells with epidermal growth factor and basic fibroblast growth factor at least about 1%, or at least about 2%, or at least about 3%, or at least about 4%, or at least about 5%, or at least about 6%, or at least about 7%, or at least about 8% of cells in the selected mammalian cell population express Sox17, Foxa2, Cerberus 1 (Cer), C—X—C chemokine receptor type 4 (Cxcr4), or a combination thereof.

To increase the proportion of cells that express markers indicative of an endoderm phenotype, a selected population of cells is contacted or mixed with epidermal growth factor and/or basic fibroblast growth factor for a time and at a concentration sufficient to differentiate or re-direct the cells to an endoderm lineage.

The time of contacting or mixing epidermal growth factor and/or basic fibroblast growth factor with the selected population of cells can vary, for example, from about 2 days to about 20 days, or from 3 days to about 15 days, or from 4 days to about 10 days, or from 5 days to about 9 days, or from 6 days to about 8 days, or about 7 days.

Epidermal growth factor and basic fibroblast growth factor can be added to a selected cell population during induced pluripotency and while directing the cells into the endoderm lineage.

Epidermal growth factor and basic fibroblast growth factor can be employed in the compositions and methods described herein in a variety of amounts and/or concentrations. For example, epidermal growth factor and/or basic fibroblast growth factor can be employed at a concentration of about 0.01 ng/ml to about 1 mg/ml, or about 0.1 ng/ml to about 300 ng/ml in a solution, or about 0.5 ng/ml to about 100 ng/ml in a solution, or about 1 ng/ml to about 50 ng/ml, or about 5 ng/ml to about 20 ng/ml in a solution, or about 10 ng/ml in a solution. In a dry formulation, the epidermal growth factor and basic fibroblast growth factor can be present in amounts of about 0.01 mg to about 1000 mg, or about 0.1 mg to about 100 mg, or about 1 mg to about 10 mg.

WNT Signaling Activators/GSK3 Inhibitors

The WNT signaling pathway includes a series of events that occur when a WNT protein binds to a cell-surface receptor of a Frizzled receptor family member. Such events result in the activation of Dishevelled family proteins which inhibit a complex of proteins that includes axin, GSK-3, and the protein APC to degrade intracellular beta-catenin. The resulting enriched nuclear beta-catenin enhances transcription by TCF/LEF family transcription factors. A WNT agonist can therefore include an agent that activates TCF/LEF-mediated transcription in a cell. WNT agonists can be selected from true WNT agonists that bind and activate a Frizzled receptor family member including any and all of the WNT family proteins, an inhibitor of intracellular beta-catenin degradation, activators of TCF/LEF, and inhibitors of GSK-3.

Activation of the WNT pathway leads to inhibition of GSK3, subsequent nuclear accumulation of β-catenin and the expression of target genes. WNT agonists can include WNT-3a, a GSK-inhibitor, WNT 5, WNT-6a, Norrin, and any other WNT family protein.

Glycogen synthase kinase 3 (GSK3) is a serine/threonine protein kinase that catalyzes the addition of phosphate molecules on certain serine and threonine amino acid residues in target protein substrates within cells. Phosphorylation of such target protein substrates often results in the modification of their specific activities or function.

As illustrated herein GSK3 inhibitors can facilitate reprogramming of differentiated cells to the endoderm lineage.

Experiments described herein show that addition of one or more GSK3 inhibitors to a selected population of cells during or after expression of pluripotency factors can increase the proportion and yield of cells that express endoderm markers. In particular, addition of a GSK3 inhibitor to cells induces those cells to express markers indicative of a endoderm phenotype such as Sox17, Foxa2, Cerberus 1 (Cer), C—X—C chemokine receptor type 4 (Cxcr4), or a combination thereof. For example, after treatment of a selected population of cells with a GSK3 inhibitor at least about 1%, or at least about 2%, or at least about 3%, or at least about 4%, or at least about 5%, or at least about 6%, or at least about 7%, or at least about 8% of cells in the selected mammalian cell population express Sox17, Foxa2, Cerberus 1 (Cer), C—X—C chemokine receptor type 4 (Cxcr4), or a combination thereof.

Examples of GSK3 inhibitors that can be employed include one or more of the following compounds:

CHIR99021 (6-(2-(4-(2,4-dichlorophenyl)-5-(4-methyl-1H-imidazol-2-yl)pyrimidin-2-ylamino)ethylamino) nicotinonitrile);

1-azakenpaullone (9-Bromo-7,12-dihydro-pyrido[3',2':2,3]azepino[4,5b]indol-6(5H)-one), BIO ((2'Z,3'E)-6-Bromoindirubin-3'-oxime);

AR-A014418 (N-(4-Methoxybenzyl)-N'-(5-nitro-1,3-thiazol-2-yl)urea);

Indirubin-3'-monoxime;

5-Iodo-indirubin-3'-monoxime;

kenpaullone (9-Bromo-7,12-dihydroindolo-[3,2-d][1]benzaxepin-6(5H)-one);

SB-415286 (3-[(3-Chloro-4-hydroxyphenyl)amino]-4-(2-nitro-phenyl)-1H-pyrrole-2,5-dione);

SB-216763 (3-(2,4-Dichlorophenyl)-4-(1-methyl-1H-indol-3-yl)-1H-pyrrole-2,5-dione);

Maybridge SEW00923SC (2 anilino-5-phenyl-1,3,4-oxadiazole);

(Z)-5-(2,3-Memylenedioxyphenyl)imidazolidine-2,4-dione,

TWS119 (3-(6-(3-aminophenyl)-7H-pyrrolo[2,3-d]pyrimidin-4-yloxy)phenol);

CHIR98014 (N2-(2-(4(4-(2,4-dichlorophenyl)-5-(1H-imidazol-1-yl)pyrimidin-2-ylamino)ethyl)-5-nitropyridine 2,6-diamine);

SB415286 (3-(3-chloro-4-hydroxyphenylamino)-4-(2-nitrophenyl)-1H-pyrrole-2,5-dione);

Tideglusib (also known as NP031112, or NP-12; 1,2,4-Thiadiazolidine-3,5-dione, 2-(1-naphthalenyl)-4-(phenylmethyl));

LY2090314 (1H-Pyrrole-2,5-dione, 3-imidazo[1,2-a]pyridin-3-yl-4-[1,2,3,4-tetrahydro-2-(1-piperidinylcarbonyl)pyrrolo[3,2,1-jk][1,4]benzodiazepin-7-yl]);

lithium salt (e.g., LiCl); or any combination thereof.

GSK-inhibitors can also include small-interfering RNAs (siRNA, Cell Signaling), lithium (Sigma), kenpaullone (Biomol International, Leost, Metal (2000) *Eur J Biochem* 267, 5983-5994), 6-Bromoindirubin-30-acetoxime (Meyer. L et al (2003) *Chem Biol* 10, 1255-1266), SB 216763 and SB 415286 (Sigma-Aldrich), and FRAT-family members and FRAT-derived peptides that prevent interaction of GSK-3 with axin. An overview is provided by Meijer et al, (2004) *Trend in Pharmacological Science* 25, 471-480, which is hereby incorporated by reference in its entirety. GSK3 inhibitors that can be used in the compositions and methods described herein can also include those disclosed in US 20120329152 by Pera et al., which is specifically incorporated herein in its entirety.

The GSK3 inhibitor can, for example, be CHIR99021, SB216763, TWS119, CHIR98014, Tideglusib, SB415286, LY2090314, or any combination thereof. In some embodiments, the GSK3 inhibitor can be CHIR99021, whose structure is shown below.

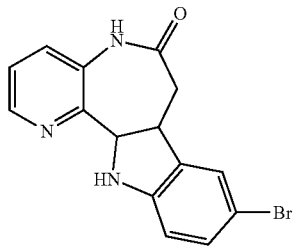 [SMILES: O=C1CC2c3cc(Br)ccc3NC2c2ncccc2N1]

The GSK3 inhibitors can also be in the form of a salt or hydrate of any of the foregoing compounds.

To increase the proportion of cells that express markers indicative of an endoderm phenotype, a selected population of cells is contacted or mixed with one or more GSK3 inhibitors for a time and at a concentration sufficient to differentiate or re-direct the cells to an endoderm lineage.

The time of contacting or mixing GSK3 inhibitor(s) with the selected population of cells can vary, for example, from about 2 days to about 50 days, or from 3 days to about 40 days, or from 4 days to about 35 days, or from 5 days to about 33 days, or from 6 days to about 30 days, or about 21 to 28 days.

GSK3 inhibitors can be added to a selected cell population during induced pluripotency and while directing the cells into the endoderm lineage.

The GSK3 inhibitors can be employed in the compositions and methods described herein in a variety of amounts and/or concentrations. For example, the GSK3 inhibitor can be employed at a concentration of about 0.01 micromolar to about 1 millimolar in a solution, or about 0.1 micromolar to about 100 micromolar in a solution, or about 0.5 micromolar to about 10 micromolar in a solution, or about 1 micromolar to about 5 micromolar in a solution. In a dry formulation, the GSK3 inhibitor can be present in amounts of about 0.01 mg to about 1000 mg, or about 1 mg to about 100 mg, or about 1 mg to about 10 mg can be present in amounts of about 0.01 mg to about 1000 mg, or about 0.1 mg to about 100 mg, or about 1 mg to about 10 mg.

Methods and assays for determining a level of GSK-3 inhibition are available to a skilled person and include, for example, the methods and assays described in Liao et al., *Endocrinology*, 145(6): 2941-2949 (2004); and in U.S. Pat. No. 8,323,919, both of which are specifically incorporated by reference herein in their entireties.

Liver Receptor homolog 1 Agonists Liver receptor homolog 1 (LRH-1, also known as NR5A2), a member of the NR5A superfamily of nuclear receptors, is highly expressed in the liver. Human LRH-1 can bind several phospholipid species, including phosphoinositides. Dilauroyl phosphatidylcholine (DLPC) is a ligand for both mouse and human LRH-1, and is an agonist thereof.

As shown herein, addition of agonists of liver receptor homolog 1 such as dilauroyl phosphatidylcholine to a selected population of cells during expression of pluripotency factors increases the proportion and yield of cells that express endoderm markers. In particular, addition of such agonists to cells induces those cells to express markers indicative of a definitive endoderm phenotype such as Sox17, Foxa2, Cerberus 1 (Cer), C—X—C chemokine receptor type 4 (Cxcr4), or a combination thereof. For example, after treatment of a selected population of cells with agonists of liver receptor homolog 1 at least about 1%, or at least about 2%, or at least about 3%, or at least about 4%, or at least about 5%, or at least about 6%, or at least about 7%, or at least about 8% of cells in the selected mammalian cell population express Sox17, Foxa2, Cerberus 1 (Cer), C—X—C chemokine receptor type 4 (Cxcr4), or a combination thereof.

To increase the proportion of cells that express markers indicative of an endoderm phenotype, a selected population of cells is contacted or mixed with at least one agonist of liver receptor homolog 1 for a time and at a concentration sufficient to differentiate or re-direct the cells to an endoderm lineage.

The time of contacting or mixing agonists of liver receptor homolog 1 with the selected population of cells can vary, for example, from about 2 days to about 50 days, or from 3 days to about 40 days, or from 4 days to about 35 days, or from 5 days to about 33 days, or from 6 days to about 30 days, or about 21-28 days.

Agonists of liver receptor homolog 1 can be added to a selected cell population during induced pluripotency and while directing the cells into the endoderm lineage.

An agonist of liver receptor homolog 1 can be used at a variety of concentrations, for example, at about 100 nM to about 1 mM, or from about 1 µM to about 750 µM, or from about 10 µM to about 500 µM, or from about 40 µM to about 400 µM, or from about 50 µM to about 300 µM, or from about 60 µM to about 250 µM, or from about 70 µM to about 200 µM, or from about 80 µM to about 150 µM, or about 100 µM.

Dilauroyl phosphatidylcholine is available commercially from various suppliers, for example, from Toronto Research Chemicals Inc. and Sigma Aldrich.

HDAC1 Inhibitors

Histone deacetylases (HDAC) are a class of enzymes that remove acetyl groups from an ε-N-acetyl lysine amino acid on a histone. Exemplary HDACs include those Class I HDAC: HDAC1, HDAC2, HDAC3, HDAC8; and Class II HDACs: HDAC4, HDAC5, HDAC6, HDAC7A, HDAC9, HDAC10. Type I mammalian HDACs include: HDAC1, HDAC2, HDAC3, HDAC8, and HDAC11, Type II mammalian HDACs include: HDAC4, HDAC5, HDAC6, HDAC7, HDAC9, and HDAC1.

As illustrated herein use of one or more histone deacetylase inhibitors can facilitate conversion of differentiated cells into the hepatocyte lineage. The histone deacetylase inhibitors can inhibit one or more of these histone deacetylases. In some instances the histone deacetylase inhibitors are inhibitors of HDAC1.

Inhibitors of HDACs (HDAC inhibitors) can include, for example, butyrate, small molecular weight carboxylates (e.g., less than about 250 amu), hydroxamic acids, benzamides, epoxyketones, cyclic peptides, and hybrid molecules. (See, for example, Drummond et al., *Annu Rev Pharmacol Toxicol* 45: 495-528 (2005), (including specific examples therein) which is hereby incorporated by reference in its entirety). Non-limiting examples of negative regulators of type I/II HDACs include:

Sodium butyrate, phenyl butyrate, or butyrate;
Suberoylanilide Hydroxamic Acid (SAHA; also called Vorinostat and MK0683), which inhibits the activities of HDAC1 and HDAC3, for example, with IC50 values of about 10 nM and 20 nM, respectively;

BML-210 (N1-(2-aminophenyl)-N8-phenyl-octanediamide, available from Sigma-Aldrich); in HeLa extracts, the IC50 of BML-210 for inhibition of HDAC activity can, for example, be about 80 µM;

Depudecin (e.g., (–)-Depudecin; 4,5:8,9-Dianhydro-1,2,6,7,11-pentadeoxy-D-threo-D-ido-undeca-1,6-dienitol), which can, for example, have an IC50 for HDAC1 of about 4.7 µM, HC Toxin ((6R,9S,14aR)-3,6R-dimethyl-9S-(7-((S)-oxiran-2-yl)-7-oxoheptyl)decahydropyrrolo[1,2-a][1,4,7,10]tetraazacyclododecine-1,4, 7,10-tetranone, available from Cayman Chemical); HC Toxin is a cell-permeable, reversible inhibitor of histone deacetylases (HDACs) (e.g., $IC_{50}$=30 nM);

Scriptaid (N-Hydroxy-1,3-dioxo-1H-benz[de]isoquinoline-2(3)-hexananmide);

Phenylbutyrate (e.g., sodium phenylbutyrate), Sodium Butyrate, pivaloyloxymethyl butyrate (Pivanex, AN-9);

Valproic Acid ((VPA) and other short chain fatty acids),

Suramin (e.g., Suramin Sodium);

Trichostatin A (TSA; (R,2E,4E)-6-(4-(dimethylamino) benzoyl)-N-hydroxy-4-methylhept-2,4-dienamide), for example, with an IC50 of about 1.8 nM;

APHA Compound 8 (3-(1-Methyl-4-phenylacetyl-1H-2-pyrrolyl)-N-hydroxy-2-propenamide), which is HDAC class I-selective;

Apicidin (Cyclo[(2S)-2-Amino-8-oxodecanoyl-1-methoxy-L-tryptophyl-L-isoleucyl-(2R)-2-piperidinecarbonyl]), which is a potent histone decetylase with, for example, an IC50=0.7 nM;

Trapoxin B (3,6-dibenzyl-9-[6-(oxiran-2-yl)-6-oxohexyl]-1,4,7,10-tetrazabicyclo[10.3.0]pentadecane-2,5,8,11-tetrone), an HDAC1 inhibitor with, for example, an IC50 of about 0.1 nM;

Chlamydocin ((3R)-3-benzyl-6,6-dimethyl-9-[6-[(2R)-oxiran-2-yl]-6-oxohexyl]-1,4,7,10-tetrazabicyclo [10.3.0]pentadecane-2,5,8,11-tetrone), with, for example, an IC50 of about 0.15 nM;

Depsipeptide (also known as romidepsin, FR1901228 or FK228; (1S,4S,7Z,10S,16E,21R)-7-ethylidene-4,21-di (propan-2-yl)-2-oxa-12,13-dithia-5,8,20,23-tetrazabicyclo[8.7.6]tricos-16-ene-3,6,19,22-pentone);

CI-994 (also known as acetyldinaline or Tacedinaline; 4-acetamido-N-(2-aminophenyl)benzamide), with, for example, a Ki of 0.05 for HDAC1;

MS-27-275 (also known as MS275 or entinostat; pyridin-3-ylmethyl-N-[[4-[(2-aminophenyl)carbamoyl]phenyl] methyl]carbamate), with, for example, an IC50 of about 0.1-1 µM;

MGCD103 (also known as Mocetinostat, N-(2-aminophenyl)-4-[[4-pyridin-3-ylpyrimidin-2-yl)amino]methyl] benzamide), with, for example, an 1C50 of about 0.1 µM;

NVP-LAQ-824 (also known as Dacinostat or LAQ824, (E)-N-hydroxy-3-[4-[[2-hydroxyethyl-[2-(1H-indol-3-yl)ethyl]amino]methyl]phenyl]prop-2-enamide), with, for example, an IC50 for HDAC1 of about 0.003-0.008 µM;

CBHA (also known as m-carboxycinnaminic acid bishydroxamic acid; N-hydroxy-3-[(E)-3-(hydroxyamino)-3-oxoprop-1-enyl]benzamide);

JNJ16241199 (also known as R306465; N-hydroxy-2-(4-(naphthalen-2-ylsulfonyl)piperazin-1-yl)pyrimidine-5-carboxamide), a potent inhibitor of HDAC1 with, for example, IC50 values of about 30 to 300 nM;

Tubacin (also known as 537049-40-4, AC1O7Y2P, CHEMBL356769, CTK8E6516, DIOX-H_003551, Y6280; N-[4-[(2R,4R,6S)-4-[(4,5-diphenyl-1,3-oxazol-2-yl)sulfanylmethyl]-6-[4-(hydroxymethyl)phenyl]-1,3-dioxan-2-yl]phenyl]-N'-hydroxyoctanediamide), with, for example, a Ki for HDAC1 of about 0.028 µM;

A-161906 (7-[4-(4-cyanophenyl)phenoxy]-heptanohydroxamic acid);

Proxamide (see WO2007031853A2);

Oxamflatin ((E)-5-[3-(benzenesulfonamido)phenyl]-N-hydroxypent-2-en-4-ynamide);

3Cl-UCHA (6-(3-chlorophenylureido)caproic hydroxamic acid);

AOE (2-amino-8-oxo-9,10-epoxydecanoic acid);

CHAP31 ((2S)—N'-hydroxy-N-[(2R)-3-(4-methoxyphenyl)-1-[[(2S,3R)-3-methyl-1-oxopentan-2-yl]amino]-1-oxopropan-2-yl]-2-(pyrrolidine-2-carbonylamino) octanediamide); or any combination thereof.

See WO2007031853A2, which is incorporated by reference herein in its entirety, for structures of many of these HDAC inhibitors.

Other inhibitors include, for example, dominant negative forms of the HDACs (e.g., catalytically inactive forms), siRNA inhibitors of the HDACs, and antibodies that specifically bind to the HDACs. Inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

In some embodiments the HDAC inhibitor(s) can include sodium butyrate.

The time of contacting or mixing HDAC inhibitor(s) with the selected population of cells can vary, for example, from about 2 days to about 50 days, or from 3 days to about 40 days, or from 4 days to about 35 days, or from 5 days to about 33 days, or from 6 days to about 30 days, or about 21-28 days.

The HDAC inhibitor(s) can be added to a selected cell population during induced pluripotency and while directing the cells into the endoderm lineage.

The HDAC inhibitor can be employed in the compositions and methods described herein in a variety of amounts and/or concentrations. For example, the HDAC inhibitor can be employed at a concentration of about 1 micromolar to about millimolar, or about 10 micromolar to about 15 millimolar, or about 25 micromolar to about 5 millimolar, or about 40 micromolar to about 1 millimolar, or about 60 micromolar to about 0.5 millimolar, or about 0.1 millimolar in a solution. In a dry formulation, the HDAC inhibitor can be present in amounts of about 0.01 mg to about 100 mg, or about 0.05 mg to about 50 mg, or about 0.1 mg to about 25 mg, or about 1 mg to about 8 mg. For example, entinostat (MS275) has been administered during clinical trials at dosages of about 4-5 mg/m$^2$ (Pili et al., *Br J Cancer* 106(1): 77-84 (2012)), where mg/m$^2$ is mg per body surface area of patient. The adult average body surface is about 2.2 m$^2$ and formulae are available converting height and weight into body surface area.

Histone Demethylase LSD1 Inhibitor

Lysine-specific demethylase 1 (LSD1, also called KDM1, AOF2, or BHC110) is a histone demethylase that suppresses gene expression by converting di-methylated lysines on histone H3 to monomethylated and unmethylated lysines. Histone methylation can influence epigenetic patterns of gene expression due to association with active promoters. As illustrated herein use of one or more inhibitors of lysine-specific demethylase 1 can facilitate conversion of differentiated cells into the hepatocyte lineage.

Exemplary inhibitors of lysine-specific demethylase 1 include, but are not limited to, parnate (also called tranylcypromine sulfate) or an equivalent salt of parnate, and phenelzine (Nardil, 2-phenylethylhydrazine). See, also, Huang et al., *Proc Natl Acad Sci USA.* 104(19): 8023-8028 (2007); Bi, X. et al., *Bioorg. Med. Chem. Lett.* 16:3229-3232 (2006); International Patent Application Nos. WO2007/021839 and WO2008/127734. MAO inhibitors can also serve as epigenetic modulators.

In some embodiments, the lysine-specific demethylase 1 inhibitor is parnate

The time of contacting or mixing lysine-specific demethylase 1 inhibitor(s) with the selected population of cells can vary, for example, from about 2 days to about 50 days, or from 3 days to about 40 days, or from 4 days to about 35 days, or from 5 days to about 33 days, or from 6 days to about 30 days, or about 21-28 days.

The lysine-specific demethylase 1 inhibitor(s) can be added to a selected cell population during induced pluripotency and while directing the cells into the endoderm lineage.

The lysine-specific demethylase 1 inhibitor can be employed in the compositions and methods described herein in a variety of amounts and/or concentrations. For example, the lysine-specific demethylase 1 inhibitor can be employed at a concentration of about 0.01 micromolar to about 20 micromolar, or about 0.05 micromolar to about 10 micromolar, or about 0.1 micromolar to about 5 micromolar, or about 0.5 micromolar to about 3 micromolar, or about 1 micromolar to about 3 micromolar, or about 1 micromolar in a solution. In a dry formulation, the lysine-specific demethylase 1 inhibitor can be present in amounts of about 0.01 mg to about 100 mg, or about 0.05 mg to about 50 mg, or about 0.1 mg to about 25 mg, or about 1 mg to about 8 mg.

DNA Methyltransferase (DNMT) Inhibitors DNA methyltransferases are enzymes that transfer methyl groups to DNA. Inhibitors of DNA methyltransferases can reactivate the expression of genes that have been repressed by DNA methylation.

Exemplary DNA methyltransferase (DNMT) inhibitors can include antibodies that bind to DNA methyltransferases, dominant negative variants of DNA methyltransferases, and siRNA and antisense nucleic acids that suppress expression of DNMT. DNA methyltransferase inhibitors include, but are not limited to, RG108 (available, e.g., from Sigma-Aldrich), 5-aza-C (5-azacitidine or azacitidine) (see, e.g., Schermelleh, et al., *Nature Methods* 2:751-6 (2005)), 5-aza-2'-deoxycytidine (5-aza-CdR) (see, e.g., Zhu, *Clinical Medicinal Chemistry* 3(3):187-199 (2003)), decitabine (see, e.g., Gore, *Nature Clinical Practice Oncology* 2:S30-S35 (2005)), doxorubicin (see, e.g., Levenson, *Molecular Pharmacology* 71:635-637 (2007)), EGCG ((−)-epigallocatechin-3-gallate) (see, e.g., Fang, et al., *Cancer Research* 63:7563-7570 (2003)), RG108 (see, e.g., Caminci, et al., WO2008/126932, incorporated herein by reference) and zebularine (see, Caminci, supra).

In some embodiments, the DNA methyltransferase inhibitor is RG108, which has the following structure.

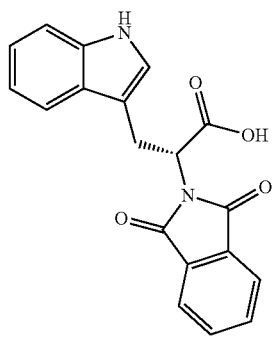 [SMILES: O=C(O)[C@@H](Cc1c[nH]c2ccccc12)N1C(=O)c2ccccc2C1=O]

The time of contacting or mixing DNA methyltransferase inhibitor(s) with the selected population of cells can vary, for example, from about 2 days to about 50 days, or from 3 days to about 40 days, or from 4 days to about 35 days, or from 5 days to about 33 days, or from 6 days to about 30 days, or about 21-28 days.

The DNA methyltransferase inhibitor(s) can be added to a selected cell population during induced pluripotency and while directing the cells into the endoderm lineage.

The DNA methyltransferase inhibitor can be employed in the compositions and methods described herein in a variety of amounts and/or concentrations. For example, the DNA methyltransferase inhibitor can be employed at a concentration of about 0.01 micromolar to about 20 micromolar, or about 0.03 micromolar to about 10 micromolar, or about 0.05 micromolar to about 5 micromolar, or about 0.1 micromolar to about 2 micromolar, or about 0.2 micromolar to about 1 micromolar, or about 0.5 micromolar in a solution. In a dry formulation, the DNA methyltransferase inhibitor can be present in amounts of about 0.01 mg to about 100 mg, or about 0.05 mg to about 50 mg, or about 0.1 mg to about 25 mg, or about 1 mg to about 8 mg.

Activin A

Activin A is a member of the TGFβ family. Activin A is highly conserved in evolution and throughout the animal kingdom. It regulates a variety of biologic processes including cell proliferation, hematopoiesis, wound healing, and fibrosis. Activin A signals through the Activin type I (Alk2, 4, or 7) and type II (ActRII or ActRIIB) receptors and shares with TGFβ the activation of the Smad cascade. See, Phillips et al., *Cytokine Growth Factor Rev.* 20(2): 153-64 (2009); Werner, *Cytokine Growth Factor Rev.* 17(3): 157-71 (2006).

As shown herein, addition of Activin A to a selected population of cells during expression of pluripotency factors can increase the proportion and yield of cells that express endoderm markers. In particular, addition of Activin A to cells induces those cells to express markers indicative of a endoderm phenotype such as Sox17, Foxa2, Cerberus 1 (Cer), C—X—C chemokine receptor type 4 (Cxcr4), or a combination thereof. For example, after treatment of a selected population of cells with Activin A at least about 1%, or at least about 2%, or at least about 3%, or at least about 4%, or at least about 5%, or at least about 6%, or at least about 7%, or at least about 8% of cells in the selected mammalian cell population express Sox17, Foxa2, Cerberus 1 (Cer), C—X—C chemokine receptor type 4 (Cxcr4), or a combination thereof.

To increase the proportion of cells that express markers indicative of an endoderm phenotype, a selected population of cells is contacted or mixed with Activin A for a time and at a concentration sufficient to differentiate or re-direct the cells to an endoderm lineage.

The time of contacting or mixing Activin A with the selected population of cells can vary, for example, from about 3 days to about 40 days, or from 5 days to about 35 days, or from 7 days to about 30 days, or from 10 days to about 28 days, or from 12 days to about 24 days, or from about 14 days to about 21 days.

Activin A can be added to a selected cell population during induced pluripotency and while directing the cells into the endoderm lineage. In some embodiments, Activin A is added to a selected cell population while directing the cells into the endoderm lineage.

Activin A can be used at a variety of concentrations, for example, at about ng/ml to about 1000 ng/ml, or from about 20 ng/ml to about 700 ng/ml, or from about 30 ng/ml to about 500 ng/ml, or from about 40 ng/ml to about 400 ng/ml, or from about 50 ng/ml to about 300 ng/ml, or from about 60 ng/ml to about 250 ng/ml, or from about 70 ng/ml to about 200 ng/ml, or from about 80 ng/ml to about 150 ng/ml, or about 100 ng/ml.

Activin A is available commercially from various suppliers, for example, from Invitrogen, PeproTech, StemRD, R&D Systems, and other vendors.

Nucleic acid and protein sequences for Activin A are available, for example, in the sequence database maintained by the National Center for Biotechnology Information (see worldwide web website at ncbi.nlm.nih.gov/). One example of a human Activin A amino acid sequence is available as accession number EAW94141.1 (GI:119614547) and provided below as SEQ ID NO:1.

```
  1 MPLLWLRGFL LASCWIIVRS SPTPGSEGHS AAPDCPSCAL
 41 AALPKDVPNS QPEMVEAVKK HILNMLHLKK RPDVTQPVPK
 61 AALLNAIRKL HVGKVGENGY VEIEDDIGRR AEMNELMEQT
121 SEIITFAESG TARKTLHFEI SKEGSDLSVV ERAEVWLFLK
161 VPKANRTRTK VTIRLFQQQK HPQGSLDTGE EAEEVGLKGE
201 RSELLLSEKV VDARKSTWHV FPVSSSIQRL LDQGKSSLDV
241 RIACEQCQES GASLVLLGKK KKKEEEGEGK KKGGGEGGAG
281 ADEEKEQSHR PFLNLQARQS EDHPHRRRRR GLECDGKVNI
321 CCKKQFFVSF KDIGWNDWII APSGYHANYC EGECPSHIAG
261 TSGSSLSFHS TVINHYRMRG HSPFANLKSC CVPTKLRPMS
401 MLYYDDGQNI IKKDIQNMIV EECGCS
```

Hence, the Activin A employed in the compositions and methods described herein can also be synthesized.

Expansion of Endodermal Cells

After incubation in the endodermal reprogramming composition, the endodermal cells can be expanded. Endodermal cell expansion can be performed in a variety of media. For example, the endodermal cells can be incubated in a composition (e.g., a medium) containing epidermal growth factor, basic fibroblast growth factor, a WNT signaling activator (e.g., a GSK3 inhibitor), a TGFβ receptor inhibitor, and combinations thereof. The composition for reprogramming cells into the endoderm lineage can include two or more, or three or more of an epidermal growth factor, a basic fibroblast growth factor, a WNT signaling activator (e.g., a GSK3 inhibitor), and/or a TGFβ receptor inhibitor.

The expansion of endodermal cells can be improved by growth of the endodermal cells for at least a few days in the presence of mammalian embryonic fibroblasts (e.g., human or mouse embryonic fibroblasts), or in media from cultured mammalian embryonic fibroblasts.

The epidermal growth factor, basic fibroblast growth factor, and/or WNT signaling activators (e.g., one or more GSK3 inhibitors) can, for example, be any of those described herein in the amounts described herein.

For example, the epidermal growth factor and basic fibroblast growth factor can be employed in compositions and media at concentrations of about 0.01 ng/ml to about 1 mg/ml, or about 0.1 ng/ml to about 300 ng/ml in a solution, or about 0.5 ng/ml to about 100 ng/ml in a solution, or about 1 ng/ml to about 50 ng/ml, or about ng/ml to about 30 ng/ml in a solution, or about 10 to 20 ng/ml in a solution. In a dry formulation, the epidermal growth factor and basic fibroblast growth factor can be present in amounts of about 0.01 mg to about 1000 mg, or about 0.1 mg to about 100 mg, or about 1 mg to about 10 mg.

The WNT signaling activator can also be any of those described herein for the endodermal reprogramming composition. In some embodiments, the WNT signaling activator is a GSK3 inhibitor such as CHIR99021, which can be used in the amounts specified herein. For example, the WNT signaling activator used in the expansion composition (e.g., in a culture medium) can be employed at a concentration of about 0.01 micromolar to about 1 millimolar in a solution, or about 0.1 micromolar to about 100 micromolar in a solution, or about 0.5 micromolar to about 10 micromolar in a solution, or about 1 micromolar to about 5 micromolar in a solution. In a dry formulation, the GSK3 inhibitor can be present in amounts of about 0.01 mg to about 1000 mg, or about 0.1 mg to about 100 mg, or about 1 mg to about 10 mg.

A variety of TGFβ receptor inhibitors can be employed in a cell expansion composition (e.g., in a cell culture medium). A TGF-beta inhibitor can directly or indirectly negatively regulate TGF-beta signaling. In some embodiments, one or more TGF-beta inhibitors binds to and reduces the activity of one or more serine/threonine protein kinases selected from the group consisting of ALK5, ALK4, TGF-beta receptor kinase 1 and ALK7, ALK4, ALK5 and ALK7 are all closely related receptors of the TGF-beta superfamily. In another embodiment, the TGF-beta receptor binds to and reduces the activity of a Smad protein, for example R-SMAD or SMAD1-5 (i.e. SMAD 1, SMAD) 2, SMAD 3, SMAD 4 or SMAD 5).

Examples of TGF-β inhibitors include, but are not limited to:

3-(6-Methyl-2-pyridinyl)-N-phenyl-4-(4-quinolinyl)-1H-pyrazole-1-carbothioamide (also known as A83-01, and available from Tocris Bioscience), which is a TGFβ kinase/Activin receptor like kinase (ALK5) inhibitor that blocks the phosphorylation of Smad2 and inhibits TGFβ-induced epithelial-to-mesenchymal transition;

SB431542 (also known as 4-[4-(1,3-benzodioxol-5-yl)-5-(2-pyridinyl)-1H-imidazol-2-yl]benzamide; available from Tocris Bioscience), which is a potent and selective inhibitor of the transforming growth factor-β (TGF-β) type I receptor Activin receptor-like kinase ALK5 ($IC_{50}$=94 nM), and its relatives ALK4 and ALK7;

4-[4-(1,3-benzodioxol-5-yl)-5-(2-pyridinyl)-1H-imidazol-2-yl]benzamide (also known as SB 431542 and available from Tocris Bioscience; a potent and selective inhibitor of TGF-β type I receptor Activin receptor-like kinase ALK5 (e.g., with $IC_{50}$-94 nM), and its relatives ALK4 and ALK7);

3-(6-Methyl-2-pyridinyl)-N-phenyl-4-(4-quinolinyl)-1H-pyrazole-1-carbothioamide (also known as A83-01 from Tocris Bioscience; a selective inhibitor of TGF-β type I receptor ALK5 kinase, type I Activin/nodal receptor ALK4 and type I nodal receptor ALK7 (IC50 values can, e.g., be 12, 45 and 7.5 nM respectively);

2-(3-(6-Methylpyridine-2-yl)-1H-pyrazol-4-yl)-1,5-naphthyridine (also known as SJN 2511 from Tocris Bioscience; selective inhibitor of the TGF-β type I receptor ALK5 (IC50 values can, e.g., be 0.004 and 0.023 μM for ALK5 autophosplorylation and ALK5 binding, respectively)

4-[4-(2,3-Dihydro-1,4-benzodioxin-6-yl)-5-(2-pyridinyl)-1H-imidazol-2-yl]benzamide (also known as D 4476 from Tocris Bioscience; a selective inhibitor of casein kinase 1 (CK1) and TGF-β type-1 receptor (ALK5) that displays greater than 20-fold selectivity over SAPK2/p38);

4-[3-(2-Pyridinyl)-1H-pyrazol-4-yl]-quinoline (also known as LY 364947 from Tocris Bioscience; a selective inhibitor of TGF-β type-I receptor (TGF-β R1, TGFR-I, TβR-1, ALK-5) (IC50 values can, e.g., be 59, 400 and 1400 nM for TGR-β RI, TGF-β RII and MLK-7K respectively);

2-(4-benzo[d][1,3]dioxol-5-yl)-2-tert-butyl-1H-imidazol-5-yl)-6-methylpyridine (also known as SB505124, and available from Selleckchem.com; a selective inhibitor of ALK4 and ALK5 (e.g., with IC50 of 129 nM and 47 nM, respectively);

6-[2-(1,1-Dimethylethyl)-5-(6-methyl-2-pyridinyl)-1H-imidazol-4-yl]quinoxaline (also known as SB 525334 from Sigma-Aldrich; a selective inhibitor of transforming growth factor-β receptor I (ALK5, TGF-βRI), with IC50=14.3 nM, for example);

2-(5-Chloro-2-fluorophenyl)-4-[(4-pyridyl)amino]pteridine (also known as SD 208 from Tocris Bioscience; a potent, orally active ATP-competitive transforming growth factor-β receptor 1 (TGF-βRI) inhibitor, e.g., with IC50=49 nanomolar);

4-(6-(4-(piperazin-1-yl)phenyl)pyrazolo[1,5-a]pyrimidin-3-yl)quinoline (also known as LDN-193189 from Miltenyi Biotec); and any combination thereof.

The inhibitor that directly or indirectly negatively regulates TGF-beta signaling can, for example, be selected from the group consisting of SB431542, A83-01, SB-431542, A83-01, SJN-2511, LY-36494, SB-505124, SB-525334, and SD-208. In some embodiments, an inhibitor that directly or indirectly negatively regulates TGF-beta signaling can inhibit ALK4, ALK5 and/or ALK7. For example, the inhibitor that directly or indirectly negatively regulates TGF-beta signaling can be A83-01, with the following structure.

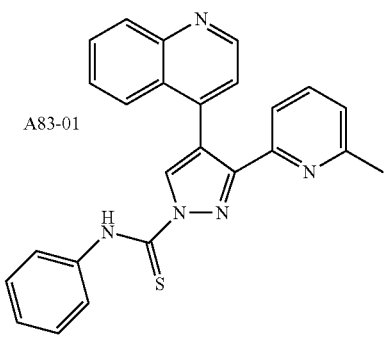 [SMILES: Cc1cccc(-c2nn(C(=S)Nc3ccccc3)cc2-c2ccnc3ccccc23)n1]

A83-01

The TGF-beta inhibitor can also be in the form of a salt or hydrate of any of the foregoing compounds.

The TGF-beta inhibitor can be employed in the compositions and methods described herein in a variety of amounts and/or concentrations. For example, the TGF-beta inhibitor can be employed at a concentration of about 0.001 micromolar to about 1 millimolar, or about 0.01 micromolar to about 100 micromolar, or about 0.05 micromolar to about 10 micromolar, or about 0.1 micromolar to about 5 micromolar, or about 0.3 micromolar to about 1 micromolar, or about 0.5 micromolar in a solution. In a dry formulation, the TGF-beta inhibitor can be present in amounts of about 0.01 mg to about 1000 mg, or about 0.1 mg to about 100 mg, or about 1 mg to about 10 mg.

Various methods for determining if a substance is a TGF-beta inhibitor are available. For example, a cell-based assay can be employed in which cells are stably transfected with a reporter construct comprising the human PAI-1 promoter or Smad binding sites, driving a luciferase reporter gene. Inhibition of luciferase activity relative to control groups can be used as a measure of compound activity (De Gouville et al., Br J Pharmacol. 2005 May; 145(2): 166-177). Another example is the ALPHASCREEN® phosphosensor assay for measurement of kinase activity (Drew A E et al., Comparison of 2 Cell-Based Phosphoprotein Assays to Support Screening and Development of an ALK Inhibitor, J Biomol Screen 16(2) 164-173, 2011).

The endodermal cells can be expanded for a number of days and through many passages. A single colony of endodermal cells, for example, can produce $10^{16}$ or more endodermal cells while maintaining the endodermal phenotype as shown by expression of SOX17 and FOXA2 but no detectable expression of NANOG in the cells. For example, the endodermal cells can be cultured for about 1 to 60 days, or about 2 to 50 days, or any number of days selected for generating enough endodermal cells for a selected therapeutic application.

Hepatocyte Differentiation

Endodermal cells can be differentiated into hepatocytes in a composition (e.g., a medium) containing a TGF-beta inhibitor, basic fibroblast growth factor (bFGF), bone morphogenetic protein 4 (BMP4), dexamethasone, hepatocyte growth factor (HGF), oncostatin M (OSM), a Notch inhibitor (e.g., compound E (C-E)), or any combination thereof. The composition for differentiating endodermal cells into the hepatocytes can include two or more, or three or more, or four or more, or five or more, or six or more, of a TGF-beta inhibitor, basic fibroblast growth factor (bFGF), bone morphogenetic protein 4 (BMP4), dexamethasone, hepatocyte growth factor (HGF), oncostatin M (OSM), and/or a Notch inhibitor (e.g., compound E (C-E)).

The endodermal progenitor cells can be incubated in a hepatocyte differentiation medium containing bFGF, BMP4, a TGF-beta inhibitor, and dexamethasone for a time before addition of HGF, OSM and a Notch inhibitor. For example, the endoderm progenitor cells (iMPC-EPCs) can be incubated in a composition containing bFGF, BMP4, a TGF-beta inhibitor, and dexamethasone for about 2 to 6 days, or about 3 to 5 days, or about 4 days.

The amounts and types of TGF-beta inhibitor, and the basic fibroblast growth factor (bFGF) employed can be as described above.

Bone morphogenetic protein 4 (BMP4) from various species including human is commercially available, for example, from R&D Systems. BMP4 can be employed in the compositions and methods described herein in a variety of amounts and/or concentrations. For example, BMP4 can be employed in compositions and media at concentrations of about 0.01 ng/ml to about 1 mg/ml in a solution, or about 0.1 ng/ml to about 300 ng/ml in a solution, or about 0.5 ng/ml to about 100 ng/ml in a solution, or about 1 ng/ml to about 50 ng/ml in a solution, or about 5 ng/ml to about 40 ng/ml in a solution, or about 10 ng/ml to about 30 ng/ml in a solution, or about 20 ng/ml in a solution. In a dry formulation, the BMP4 can be present in amounts of about 0.01 mg to about 1000 mg, or about 0.1 mg to about 100 mg, or about 1 mg to about 10 mg.

Dexamethasone is commercially available and can be used in various concentrations. For example, the dexamethasone can be employed at a concentration of about 0.001 micromolar to about 200 micromolar, or about 0.01 micromolar to about 100 micromolar, or about 0.05 micromolar to about 10 micromolar, or about 0.1 micromolar in a solution. In a dry formulation, dexamethasone can be present in amounts of about 0.01 mg to about 1000 mg, or about 0.1 mg to about 100 mg, or about 1 mg to about 10 mg.

After incubation of the endoderm progenitor cells (iMPC-EPCs) in a hepatocyte differentiation medium (containing bFGF, BMP4, a TGF-beta inhibitor, and dexamethasone), the cells can be incubated in a hepatocyte maturation medium. Such a hepatocyte maturation medium can contain a TGF-beta inhibitor, dexamethasone, hepatocyte growth factor (HGF), oncostatin M (OSM), a Notch inhibitor (e.g., compound E (C-E)), or any combination thereof.

The types and amounts of the TGF-beta inhibitor and the dexamethasone are as described above and in the Examples.

Hepatocyte growth factor (HGF) is a single inactive polypeptide and is cleaved by serine proteases into a 69-kDa alpha-chain and 34-kDa beta-chain. A disulfide bond between the alpha and beta chains produces the active, heterodimeric molecule. The protein belongs to the plasminogen subfamily of S1 peptidases but has no detectable protease activity. Human HGF is available commercially, for example, from ProSpec protein specialists (prospecbio.com). Murine and human HGF are also available commercially, for example, from PeproTech (peprotech.com)

HGF can be employed in the compositions and methods described herein in a variety of amounts and/or concentrations. For example, HGF can be employed in compositions and media at concentrations of about 0.01 ng/ml to about 1 mg/ml in a solution, or about 0.1 ng/ml to about 300 ng/ml in a solution, or about 0.5 ng/ml to about 100 ng/ml in a solution, or about 1 ng/ml to about 50 ng/ml in a solution, or about 5 ng/ml to about 40 ng/ml in a solution, or about 10 ng/ml to about 30 ng/ml in a solution, or about 20 ng/m in a solution. In a dry formulation, the HGF can be present in amounts of about 0.01 mg to about 1000 mg, or about 0.1 mg to about 100 mg, or about 1 mg to about 10 mg.

Oncostatin M is a protein that in humans is encoded by the OSM gene. OSM is a pleiotropic cytokine that belongs to the interleukin 6 group of cytokines, and resembles leukemia inhibitory factor (LIF) in structure and function. Oncostatin M from various species including human and is commercially available, for example, from Prospec Protein Specialists and R&D Systems. OSM can be employed in the compositions and methods described herein in a variety of amounts and/or concentrations. For example, OSM can be employed in compositions and media at concentrations of about 0.01 ng/ml to about 1 mg/ml in a solution, or about 0.1 ng/ml to about 300 ng/ml in a solution, or about 0.5 ng/ml to about 100 mg/ml in a solution, or about 1 ng/ml to about 50 ng/ml in a solution, or about 5 ng/ml to about 40 ng/ml in a solution, or about 10 ng/ml to about 30 ng/ml in a solution, or about 20 ng/ml in a solution. In a dry formulation, the OSM can be present in amounts of about 0.01 mg to about 1000 mg, or about 0.1 mg to about 100 mg, or about 1 mg to about 10 mg.

The Notch inhibitor can operate in any manner that inhibits Notch function. For example, the Notch inhibitor can inhibit Notch signaling, inhibit Notch transcription, inhibit Notch translation, or competitively inhibit Notch. Examples of Notch inhibitors include gamma secretase inhibitors, Notch interfering RNA, and dominant negative Notch proteins.

Notch signaling can be modulated by altering the activity of the gamma-secretase complex. This complex cleaves the Notch receptor releasing the Notch intracellular domain (reviewed in Fortini, *Nature Reviews Molecular and Cell Biology* 3: 673-684 (2002)). Gamma-secretase inhibitors reduce the level of Notch signaling and lead to effects that resemble or are identical to the phenotypes produced by loss of function mutations in Notch genes in a variety of organisms and experimental systems (Dovey et al., *Journal of Neurochemistry* 76:173-181 (2001); Hadland et al., *Proceedings of the National Academy of Sciences USA* 98: 7487-7491 (2001); Doerfler et al., *Proceedings of the National Academy of Sciences USA* 98: 9312-9317 (2001); Micchelli et al., *The FASEB Journal* 17: 79-81 (2002)).

A variety of Notch and/or gamma-secretase inhibitors can be employed, including any of the following:

Compound E (C-E) is a cell permeable, potent, selective, non-transition state and non-competitive inhibitor of γ-secretase ($IC_{50}$=0.3 nM for total β-amyloid) and Notch processing, which inhibits cell differentiation. At higher concentrations (20-400 μM), compound E only weakly affects the presenilase activity. Compound E is commercially available from a variety of sources, including Enzo Life Sciences (enzolifesciences.com/ALX-270-415/compound-e/). The structure of compound E is shown below.

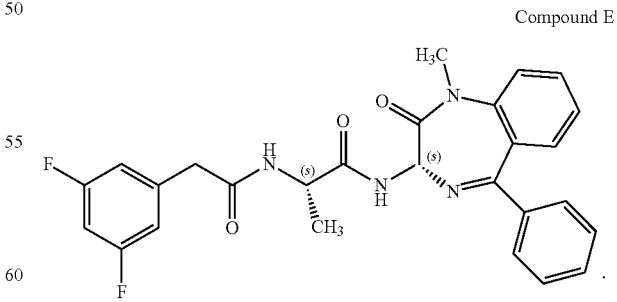

Compound E

RO4929097 is a γ secretase inhibitor (available from Selleckcehem.com) with IC50 of 4 nM, inhibiting cellular processing of Aβ40 and Notch with EC50 of 14 nM and 5 nM, respectively. RO4929097 has the following structure:

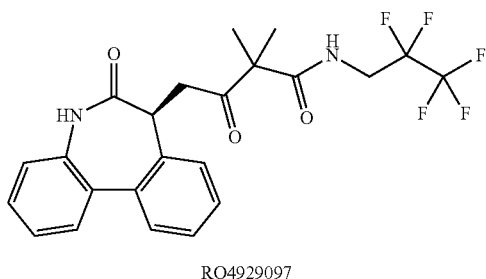

RO4929097

DAPT (GSI-IX) is a γ-secretase inhibitor (available from Sigma-Aldrich) that inhibits Aβ production. DAPT has the following structure:

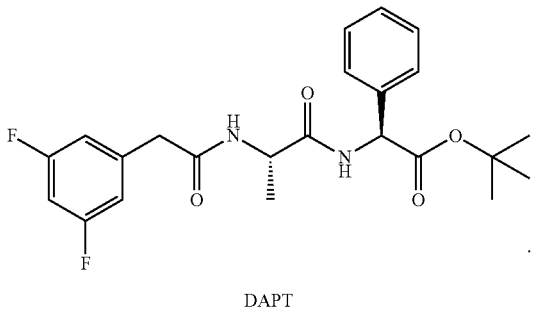 [SMILES: C[C@H](NC(=O)Cc1cc(F)cc(F)c1)C(=O)N[C@H](C(=O)OC(C)(C)C)c1ccccc1]

DAPT

Gamma-Secretase Inhibitor 1, which has the following structure: Z-Leu-Leu-Nle-CHO (Nle=Norleucine) (available from EMD Millipore (see, emdmillipore.com/life-science-research/gamma-secretase-inhibitor).

Gamma-Secretase Inhibitor II, which is a cell-permeable, reversible and selective peptidomimetic inhibitor of γ-secretase ($IC_{50}$=13 μM for Aβ). It displays only weak inhibitory activity against calpain II ($IC_{50}$=100 μM in a purified enzyme assay). Gamma-Secretase Inhibitor II has the following structure:

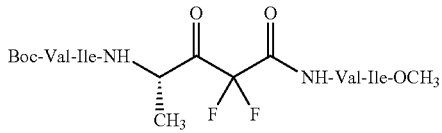

In some embodiments, the Notch inhibitor is compound E.

The Notch inhibitor can be used in various concentrations. For example, the Notch inhibitor can be employed at a concentration of about 0.001 micromolar to about 200 micromolar, or about 0.01 micromolar to about 100 micromolar, or about 0.05 micromolar to about 10 micromolar, or about 0.1 micromolar in a solution. In a dry formulation, Notch inhibitor can be present in amounts of about 0.01 mg to about 1000 mg, or about 0.1 mg to about 100 mg, or about 1 mg to about 10 mg.

Cells can be incubated in a hepatocyte maturation medium containing a TGF-beta inhibitor, dexamethasone, hepatocyte growth factor (HGF), oncostatin M (OSM), a Notch inhibitor (e.g., compound E (C-E)), or any combination thereof; for varying amounts of time. For example, the cells can be incubated in a hepatocyte maturation medium until at least some of the cells express hepatocyte markers such as albumin or α-1 Antitrypsin (AAT). The incubation time can vary, for example, from about 4 days to about 40 days, or from about 6 days to about 34 days, or from about 7 days to about 30 days, or from about 8 days to about 25 days, or from about 10 days to about 20 days, or from about 12 days to about 18 days, or about 16 days.

Pluripotency Factor Expression/Translation in Selected Cells

As described herein, differentiated cells can be reprogrammed to the endodermal/hepatocyte lineage by incubation of the differentiated cells with the reprogramming compositions described herein during or after expression of pluripotency factor polypeptides (e.g., OCT4, SOX2, KLF4, or any combination thereof) in selected differentiated cells.

In some embodiments, the transcription factor(s) employed to reprogram cells to the cardiac lineage can be introduced into a selected cell or a selected population of cells by a recombinant expression vector. Techniques in the field of recombinant genetics can be used for such transformation. Basic texts disclosing general methods of recombinant genetics include Sambrook et al., *Molecular Cloning, A Laboratory Manual* (3rd ed. 2001); Kriegler, *Gene Transfer and Expression: A Laboratory Manual* (1990); and Current Protocols in Molecular Biology (Ausubel et al., eds., 1994)).

In some embodiments, the species of cell and the species of the protein to be expressed are the same. For example, if a mouse cell is used, a mouse ortholog is introduced into the cell. If a human cell is used, a human ortholog is introduced into the cell.

It will be appreciated that where two or more proteins are to be expressed in a cell, one or multiple RNA molecules or expression cassettes can be used. For example, one expression cassette can express multiple polypeptides, and a polycistronic expression cassette can be used. In some embodiments, the vectors do not contain a mammalian origin of replication. In some embodiments, the expression vector is not integrated into the genome and/or is introduced via a vector that does not contain a mammalian origin of replication.

The selected cell for expression of the transcription factors (and contacting with the reprogramming compositions described herein) can be a mixture or population of cells. For example, the selected cell can be a differentiated, non-endodermal and non-hepatocyte cell (or a mixture of differentiated, non-endodermal and non-hepatocyte cells). The selected cell(s) can be mammalian cells that are not pluripotent cells. Mammalian cells can be from humans or non-human mammals. Exemplary non-human mammals include, but are not limited to, mice, rats, cats, dogs, rabbits, guinea pigs, hamsters, sheep, pigs, horses, bovines, and non-human primates (e.g., chimpanzees, macaques, and apes).

Examples of selected cells include differentiated cells as well as progenitor cells. Differentiated cells include terminally differentiated cells as well as partially differentiated cells (e.g., multipotent or unipotent stem cells). Examples of differentiated cells include, but are not limited to, cells from a tissue selected from fibroblasts, bone marrow, skin, skeletal muscle, fat tissue and peripheral blood cells. Exemplary cell types include, but are not limited to, fibroblasts, myoblasts, neurons, squamous cells, osteoblasts, osteoclasts, and T-cells.

The transcription factor(s) can be introduced, translated, and/or expressed within selected cells by a variety of procedures. In some embodiments, the transcription factor(s)

can be transiently expressed in the selected cells (e.g., for 2-12 days, or 3-10 days or 4-9 days, or about 7 days) either before or during exposure of the cells to the reprogramming composition.

Endogenous expression of the OCT4 transcription factor can be increased by introduction of microRNA-302 (miR-302), or by increased expression of miR-302. See, e.g., Hu et al., *Stem Cells* 31(2): 259-68 (2013), which is incorporated herein by reference in its entirety. Hence, miRNA-302 can be an inducer of endogenous Oct polypeptide expression, which is introduced alone or with a nucleic acid that encodes the Oct polypeptide.

Direct Translation from Introduced RNA

When the transcription factor(s) are expressed transiently in the selected cells, the transcription factor(s) can be introduced via an RNA molecule, which is translated to protein within the cell's cytoplasm. For example, the transcription factor(s) can be translated from introduced RNA molecules that have the open reading frame (ORF) for the transcription factor(s) flanked by a 5' untranslated region (UTR) containing a translational initiation signal (e.g., a strong Kozak translational initiation signal) and a 3' untranslated region terminating with an oligo(dT) sequence for templated addition of a polyA tail. Such RNA molecules do not have the promoter sequences employed in most expression vectors and expression cassettes. The RNA molecules can be introduced into the selected cells by a variety of techniques, including electroporation or by endocytosis of the RNA complexed with a cationic vehicle. See, e.g., Warren et al., *Cell Stem Cell* 7: 618-30 (2010), incorporated herein by reference in its entirety.

Protein translation can persist for several days, especially when the RNA molecules are stabilized by incorporation of modified ribonucleotides. For example, incorporation of 5-methylcytidine (5mC) for cytidine and/or pseudouridine (psi) for uridine can improve the half-life of the introduced RNA in vivo, and lead to increased protein translation. If high levels of expression are desired, or expression for more than a few days is desired, the RNA can be introduced repeatedly into the selected cells.

The RNA molecules encoding the transcription factor(s) can also include a 5' cap, a nuclear localization signal, or a combination thereof. See, e.g., Warren et al., *Cell Stem Cell* 7: 618-30 (2010).

Such RNA molecules can be made, for example, by in vitro transcription of a Oct4, Sox2, and/or Klf4 template using a ribonucleoside blend that includes a 3'-O-Me-m7G (5')ppp(5')G ARCA cap analog (New England Biolabs), adenosine triphosphate and guanosine triphosphate (USB, Cleveland, Ohio), 5-methylcytidine triphosphate and pseudouridine triphosphate (TriLink Biotechnologies, San Diego, Calif.). The RNA molecules can also be treated with phosphatase to reduce cytotoxicity.

The Oct4 transcription factor RNA molecules can be introduced alone or with miRNA-302, which can be an inducer of endogenous Oct polypeptide expression.

Promoters and Enhancers

An expression cassette, plasmid, or vector can also be used to transform a selected cell with a nucleic acid segment that encodes one or more of the transcription factor(s). Such an expression cassette, plasmid, or vector can have regulatory sequences operably linked to the coding region of a transcription factor to allow expression of the transcription factor mRNA and polypeptide. A variety of plasmids and/or vectors can be used to introduce nucleic acids encoding one or more transcription factor(s) into a selected cell (also referred to as a "starting cell" or a "host cell"). In some embodiments, the plasmid or vector does not integrate into the genome of the cells and does not contain a mammalian origin of replication.

A nucleic acid encoding the transcription factor(s) can be operably linked to a promoter and/or enhancer to facilitate expression of the transcription factor(s).

The promoter can be one naturally associated with a transcription factor gene or nucleic acid segment. Such a naturally associated promoter can be referred to as the "natural promoter" and may be obtained by isolating the 5' non-coding sequences located upstream of the coding segment and/or exon. Similarly, an enhancer may be one naturally associated with a nucleic acid sequence. However, the enhancer can be located either downstream or upstream of that sequence.

Alternatively, certain advantages will be gained by positioning the coding nucleic acid segment (e.g., for the transcription factor(s)) under the control of a recombinant or heterologous promoter, which refers to a promoter that is not normally associated with a nucleic acid in its natural environment. A recombinant or heterologous enhancer refers also to an enhancer not normally associated with a nucleic acid sequence in its natural environment. Such promoters or enhancers can include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, for example, via polymerase chain reaction, in connection with the compositions disclosed herein (see U.S. Pat. No. 4,683,202, U.S. Pat. No. 5,928,906, each incorporated herein by reference).

The promoters employed may be constitutive, inducible, developmentally-specific, tissue-specific, and/or useful under the appropriate conditions to direct high level expression of the nucleic acid segment. For example, the promoter can be a constitutive promoter such as, a CMV promoter, a CMV cytomegalovirus immediate early promoter, a CAG promoter, an EF-1α promoter, a HSV1-TK promoter, an SV40 promoter, a β-actin promoter, a PGK promoter, or a combination thereof. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tot promoter, the hsp70 promoter and a synthetic promoter regulated by CRE. In certain embodiments, cell type-specific promoters are used to drive expression of reprogramming factors in specific cell types. Examples of suitable cell type-specific promoters useful for the methods described herein include, but are not limited to, the synthetic macrophage-specific promoter described in He et at (2006), *Human Gene Therapy*, 17:949-959; the granulocyte and macrophage-specific lysozyme M promoter (see, e.g., Faust et al (2000), *Blood* 96(2):719-726); and the myeloid-specific CD11b promoter (see, e.g., Dziennis et at (1995) *Blood* 85(2):319-329). Other examples, of promoter that can be employed include a human EF1α elongation factor promoter, a CMV cytomegalovirus immediate early promoter, a CAG chicken albumin promoter, a viral promoter associated with any of the viral vectors described herein, a promoter that is homologous to any of the promoters described herein (e.g., from another species), or any combination thereof. Examples of prokaryotic promoters that can be used include, but are not limited to, SP6, T7, T5, tac, bla, trp, gal, lac, or maltose promoters.

In some embodiments, an internal ribosome entry site (IRES) element can be used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, *Nature* 334 (6180):320-325 (1988)), as well an IRES from a mammalian message (Macejak and Samow, *Nature* 353:90-94 (1991)). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

Plasmid Vectors

A plasmid vector can be used to introduce an expression cassette into a selected cell. In general, plasmid vectors contain control sequences (e.g., promoters, enhancers, etc.) are from species compatible with the host cell in which they are used. The vector can also contain a nucleic acid segment encoding a marker is capable of providing phenotypic selection in transformed cells. While a plasmid vector can contain a prokaryotic origin of replication, in some embodiments, the vectors do not contain a mammalian origin of replication.

Viral Vectors

The ability of certain viruses to infect cells or enter cells via receptor-mediated endocytosis, and express viral genes stably and efficiently have made them attractive candidates for the transfer of foreign nucleic acids into cells (e.g., mammalian cells). Viral vectors can include control sequences such as promoters for expression of the Oct polypeptide. Although many viral vectors integrate into host cell genomes, if desired, the segments that allow such integration can be removed or altered to prevent such integration. Moreover, in some embodiments, the vectors do not contain a mammalian origin of replication. Non-limiting examples of virus vectors are described below that can be used to deliver nucleic acids encoding a transcription factor into a selected cell.

i. Adenoviral Vectors

One method for delivery of the nucleic acid into selected cells involves the use of an adenovirus expression vector. Adenovirus vectors can have a low capacity for integration into genomic DNA. Adenoviruses also have a high efficiency of gene transfer afforded by these vectors. "Adenovirus expression vector" is meant to include those constructs containing adenovirus sequences sufficient to express a tissue or cell-specific construct that has been cloned therein. The genetic organization of adenovirus includes an approximate 36 kb, linear, double-stranded DNA virus, which allows substitution of large pieces of adenoviral DNA with foreign sequences up to 7 kb (Grunhaus et al., *Seminar in Virology,* 200(2):535-546, 1992)).

ii. AAV Vectors

The nucleic acid may be introduced into the cell using adenovirus assisted transfection. Increased transfection efficiencies have been reported in cell systems using adenovirus coupled systems (Kelleher and Vos, *BioTechniques,* 17(6): 1110-7, 1994; Cotten et al., *Proc Natl Acad Sci USA,* 89(13):6094-6098, 1992; Curiel, *Nat Immun,* 13(2-3):141-64, 1994.). Adeno-associated virus (AAV) is an attractive vector system as it has a high frequency of integration and it can infect non-dividing cells, thus making it useful for delivery of genes into mammalian cells, for example, in tissue culture (Muzyczka, *Curr Top Microbiol Immunol.* 158:97-129, 1992) or in vivo. Details concerning the generation and use of rAAV vectors are described in U.S. Pat. Nos. 5,139,941 and 4,797,368, each incorporated herein by reference in its entirety.

iii. Retroviral Vectors

Retroviruses can integrate their genes into the host genome, transfer a large amount of foreign genetic material, infect a broad spectrum of species and cell types, and can be packaged in special cell-lines (Miller et al., *Am. J. Clin. Oncol.,* 15(3):216-221, 1992). In some embodiments, a retroviral vector is altered so that it does not integrate into the host cell genome.

A retroviral vector can be constructed by inserting a nucleic acid (e.g., one encoding a transcription factor) into the viral genome in the place of some viral sequences to produce a virus that is replication-defective. To produce virions, a packaging cell line containing the gag, pol, and env genes, but without the LTR and packaging components, is constructed (Mann et al., *Cell,* 33:153-159, 1983). When a recombinant plasmid containing a cDNA, together with the retroviral LTR and packaging sequences is introduced into a special cell line (e.g., by calcium phosphate precipitation), the packaging sequence allows the RNA transcript of the recombinant plasmid to be packaged into viral particles, which are then secreted into the culture media (Nicolas and Rubinstein, In: *Vectors: A survey of molecular cloning vectors and their uses*, Rodriguez and Denhardt, eds., Stoneham: Butterworth, pp. 494-513, 1988; Temin, In: *Gene Transfer*, Kucherlapati (ed.), New York: Plenum Press, pp. 149-188, 1986; Mann et al., *Cell.* 33:153-159, 1983). The media containing the recombinant retroviruses is then collected, optionally concentrated, and used for gene transfer. Retroviral vectors are able to infect a broad variety of cell types. However, integration and stable expression typically involves the division of host cells (Paskind et al., *Virolog,* 67:242-248, 1975).

Lentiviruses are complex retroviruses, which, in addition to the common retroviral genes gag, pol, and env, contain other genes with regulatory or structural function. Information on lentiviral vectors is available, for example, in Naldini et al., *Science,* 272(5259):263-267, 1996; Zufferey et al., *Nat Biotechnol,* 15(9):871-875, 1997; Blomer et al., *J Virol.,* 71(9):6641-6649, 1997; U.S. Pat. Nos. 6,013,516 and 5,994, 136, each of which is incorporated herein by reference in its entirety. Some examples of lentivirus include the Human Immunodeficiency Viruses: HIV-1, HIV-2 and the Simian Immunodeficiency Virus: SW. Lentiviral vectors have been generated by multiply attenuating the HIV virulence genes, for example, the genes env, vif, vpr, vpu and nef are deleted to make the vector biologically safe. The lentivirus employed can also be replication and/or integration defective.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, which is incorporated herein by reference in its entirety. Those of skill in the art can target the recombinant virus by linkage of the envelope protein with an antibody or a particular ligand for targeting to a receptor of a particular cell-type. For example, a target specific vector can be generated by inserting a nucleic acid segment (including a regulatory region) of interest into the viral vector, along with another gene that encodes a ligand for a receptor on a specific target cell type.

iv. Delivery Using Modified Viruses

A nucleic acid to be delivered can be housed within an infective virus that has been engineered to express a specific binding ligand. The virus particle will thus bind with specificity to the cognate receptors of the target cell and deliver the contents to the cell.

Selected (Starting) Cells

Selected cells can be contacted or incubated with the compositions described herein. Such selected cells are also referred to as starting cells. A starting population of cells can be derived from essentially any source, and can be heterogeneous or homogeneous. In certain embodiments, the cells to be treated as described herein are adult cells, including essentially any accessible adult cell type(s). In other embodiments, the cells used according to the invention are adult stem cells, progenitor cells, or somatic cells. In still other embodiments, the cells treated with any of the compositions and/or methods described herein include any type of cell from a newborn, including, but not limited to newborn cord blood, newborn stem cells, progenitor cells, and tissue-derived cells (e.g., somatic cells). Accordingly, a starting population of cells that is reprogrammed by the compositions and/or methods described herein, can be essentially any live somatic cell type.

As illustrated herein, fibroblasts can be reprogrammed to cross lineage boundaries and to be directly converted to another cell type—an endodermal cell or a hepatocyte cell type.

Various cell types from all three germ layers have been shown to be suitable for somatic cell reprogramming by genetic manipulation, including, but not limited to liver and stomach (Aoi et al., *Science* 321(5889):699-702 (2008); pancreatic β cells (Stadtfeld et al., *Cell Stem Cell* 2: 230-40 (2008); mature B lymphocytes (Hanna et al., *Cell* 133: 250-264 (2008); human dermal fibroblasts (Takahashi et al., (ell 131, 861-72 (2007); Yu et al., *Science* 318(5854) (2007); Lowry et al., *Proc Natl Acad Sci USA* 105, 2883-2888 (2008); Aasen et al., *Nat Biotechnol* 26(11): 1276-84 (2008); meningiocytes (Qin et al., *J Biol Chem* 283(48):33730-5 (2008); neural stem cells (DiSteffano et al., *Stem Cells Devel.* 18(5): (2009); and neural progenitor cells (Eminli et al., *Stem Cells* 26(10): 2467-74 (2008). Any such cells can be reprogrammed and/or programmed by use of the compositions and methods described herein.

The mammalian cells for reprogramming can, for example, be selected from one or more of fibroblasts, endothelial cells, B cells, T cells, dendritic cells, keratinocytes, adipose cells, epithelial cells, epidermal cells, chondrocytes, cumulus cells, neural cells, glial cells, astrocytes, cardiac cells, esophageal cells, skeletal muscle cells, skeletal muscle satellite melanocytes, hematopoietic cells, osteocytes, macrophages, monocytes, mononuclear cells or stem cells including embryonic stem cells, embryonic germ cells, adult brain stem cells, epidermal stem cells, skin stem cells, pancreatic stem cells, kidney stem cells, liver stem cells, breast stem cells, lung stem cells, muscle stem cells, heart stem cells, eye stem cells, bone stem cells, spleen stem cells, immune system stem cells, cord blood stem cells, bone marrow stem cells and peripheral blood stem cells.

The cells can be autologous or allogeneic cells (relative to a subject to be treated or who may receive the cells).

Nucleic Acid Delivery

Suitable methods for nucleic acid delivery into cells, tissues, or an organism include a variety of procedures by which a nucleic acid (e.g., RNA or DNA) can be introduced into a cell, a tissue or an organism. Examples of procedures include, for example, those described by Stadtfeld and Hochedlinger, *Nature Method* 6(5):329-330 (2009); Yusa et al., *Nat. Methods* 6:363-369 (2009); Woltjen, et al., *Nature* 458, 766-770 (9 Apr. 2009)). Such methods include, but are not limited to, direct delivery of DNA such as by ex vive transfection (e.g., Wilson et al., *Science,* 244:1344-1346, 1989, Nabel and Baltimore, *Nature* 326:711-713, 1987), optionally with Fugene6 (Roche) or Lipofectamine (Invitrogen); by injection (e.g., U.S. Pat. Nos. 5,994,624, 5,981, 274, 5,945,100, 5,780,448, 5,736,524, 5,702,932, 5,656,610, 5,589,466 and 5,580,859, each incorporated herein by reference), including microinjection (e.g., Harland and Weintraub, *J. Cell Biol.,* 101:1094-1099, 1985; U.S. Pat. No. 5,789,215, incorporated herein by reference in its entirety); by electroporation (e.g., U.S. Pat. No. 5,384,253, incorporated herein by reference in its entirety, Tur-Kaspa et al., *Mol. Cell Biol.,* 6:716-718, 1986; Potter et al., *Proc. Natl Acad. Sci. USA,* 81:7161-7165, 1984); by calcium phosphate precipitation (e.g., Graham and Van Der Eb, *Virolog,* 52:456-467, 1973; Chen and Okayama, *Mol. Cell Biol.,* 7(8):2745-2752, 1987; Rippe et al., *Mol. Cell Biol.,* 10:689-695, 1990); by use of DEAE-dextran followed by polyethylene glycol (e.g., Gopal, *Mol. Cell Biol.,* 5:1188-1190, 1985); by direct sonic loading (e.g., Fechheimer et al., *Proc. Nat'l Acad. Sci. USA,* 84:8463-8467, 1987); by liposome mediated transfection (e.g., Nicolau and Sene, *Biochim. Biophys. Acta,* 721:185-190, 1982, Fraley et al., *Proc. Nat'l Acad. Sci. USA,* 76:3348-3352, 1979; Nicolau et al., *Methods Enzymol.,* 149:157-176, 1987, Wong et al., *Gene,* 10:87-94, 1980, Kaneda et al., *Science,* 243:375-378, 1989, Kato et al., *Biol. Chem.,* 266:3361-3364, 1991), receptor-mediated transfection (e.g., Wu and Wu, *Biochemistry,* 27:887-892, 1988; Wu and Wu, *J. Biol. Chem.,* 262:4429-4432, 1987); by endocytosis of the RNA complexed with a cationic vehicle (Warren et al., *Cell Stem Cell* 7; 618-30 (2010)); and any combination of such methods. Each of foregoing references is incorporated herein by reference in its entirety.

Reprogramming Methods

Selected starting cells are treated for a time and under conditions sufficient to convert the starting cells across lineage and/or differentiation boundaries to form endodermal progenitor cells and/or hepatocytes.

During and after expression of pluripotency factors (e.g., OCT4, KLF4, SOX2, or any combination thereof) cells can be replated for a few days (e.g., 1-5 days), and then reprogramming can be initiated for a period of time of about 2 days to about 14 days, or about 3 days to about 12 days, or about 4 days to about 10 days, or about 5 days to about 9 days, or about 6 days to about 8 days, or about 7 days. The reprogramming initiation medium can include a epidermal growth factor (EGF), basic fibroblast growth factor (bFGF), an activator of WNT signaling (e.g., a GSK3 inhibitor), a nuclear receptor liver receptor homolog 1 agonist (e.g., dilauroyl phosphatidylcholine (DLPC)), a histone deacetylase (HDAC) inhibitor (e.g., sodium butyrate), a histone demethylase LSD1 inhibitor (e.g., parnate), a DNA methyltransferase (DNMT) inhibitor (e.g., RG108), or any combination thereof.

Reprogramming can occur after initiation. The time for reprogramming of a population of cells can vary, for example, from about 2 days to about 50 days, or from about 3 days to about 40 days, or from about 4 days to about 35 days, or from about 5 days to about 33 days, or from about 6 days to about 30 days, or from about 12 to about 28 days, or from about 14 to about 21 days. Cells can be incubated in a reprogramming medium that includes an activator of WNT signaling (e.g., a GSK3 inhibitor), a nuclear receptor liver receptor homolog 1 agonist (e.g., dilauroyl phosphatidylcholine (DLPC)), a histone deacetylase (HDAC) inhibitor (e.g., sodium butyrate), a histone demethylase LSD1 inhibitor (e.g., parnate), a DNA methyltransferase (DNMT) inhibitor (e.g., RG108), Activin A, or any combination thereof.

After such reprogramming, the cell population contains induced endodermal progenitor cells. For example, at least about 1%, at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90% or greater than 90% of the cells in the reprogrammed population can be induced endoderm progenitor cells.

As described above, the endodermal progenitor cells can be expanded for a number of days and through many passages. A single colony of endodermal cells, for example, can produce $10^{16}$ or more endodermal cells while maintaining the endodermal phenotype as shown by expression of SOX17 and FOXA2 but no detectable expression of NANOG in the cells. For example, the endodermal cells can be cultured for about 1 to 60 days, or about 2 to 50 days, or any number of days selected for generating enough endodermal cells for a selected therapeutic application.

The induced endodermal progenitor cells can be reprogrammed to form hepatocytes by incubation in a medium containing bFGF, BMP4, a TGF-beta inhibitor, and dexamethasone for a time before addition of HGF, OSM and a Notch inhibitor. For example, the endoderm progenitor cells (iMPC-EPCs) can be incubated in a medium containing bFGF, BMP4, a TGF-beta inhibitor, and dexamethasone for about 2 to 7 days, or about 3 to 6 days, or about 4-5 days.

After such reprogramming, the cell population contains immature and mature hepatocytes. For example, at least about 1%, at least about 2%, at least about 5%, at least about 10%, at least about 15%, at least about 20%, at least about 25%, at least about 30%, at least about 35%, at least about 40%, at least about 45%, at least about 50%, at least about 55%, at least about 60/%, at least about 65%, at least about 70%, at least about 75%, at least about 80%, at least about 85%, at least about 90% or greater than 90% of the cells in the reprogrammed population can be immature and mature hepatocytes.

To facilitate maturation of the cell population containing immature and mature hepatocytes, the cell population can be incubated in a hepatocyte maturation medium containing a TGF-beta inhibitor (e.g., A83), dexamethasone, hepatocyte growth factor (HGF), oncostatin M (OSM), a Notch inhibitor (e.g., compound E (C-E)), or any combination thereof, for varying amounts of time. For example, the cells can be incubated in a hepatocyte maturation medium until at least some of the cells express hepatocyte markers such as albumin or α-1 Antitrypsin (AAT). The incubation time can vary, for example, from about 4 days to about 40 days, or from about 6 days to about 34 days, or from about 7 days to about 30 days, or from about 8 days to about 25 days, or from about 10 days to about 20 days, or from about 12 days to about 18 days, or about 16 days.

Therapy

Also described herein is a method for treating a patient suffering from, or at risk of developing, a liver condition or disease. The liver condition or disease can, for example, be chronic liver failure, acute liver failure, Alagille syndrome, alcohol-related liver disease, alcoholic hepatitis, enlarged liver, Gilbert's syndrome, liver cysts, liver hemangioma, non-alcoholic fatty liver disease, nonalcoholic steatohepatitis, primary sclerosing cholangitis, or a combination thereof. The methods involve obtaining (induced) multipotent cells, endodermal progenitor cells, immature hepatocytes, and/or mature hepatocytes as described herein, and administering or implanting one or more of these cell types into a mammalian subject. The cells can be expanded prior to administration. For example, as illustrated herein, the induced endodermal progenitor cells can be expanded to generate a sufficient number of cells for therapeutic purposes, without loss of the endodermal differentiation state.

The (induced) multipotent cells, endodermal progenitor cells, immature hepatocytes, and/or mature hepatocytes cells can be implanted as dispersed cells or formed into clusters. Alternatively, the (induced) multipotent cells, endodermal progenitor cells, immature hepatocytes, and/or mature hepatocytes can be infused into the subject, for example, via a hepatic portal vein. Alternatively, cells may be provided in biocompatible degradable polymeric supports, porous non-degradable devices or encapsulated to protect from host immune response. Cells may be implanted into an appropriate site in a subject. The implantation sites include, for example, the liver, natural pancreas, renal subcapsular space, omentum, peritoneum, subserosal space, intestine, stomach, or a subcutaneous pocket.

The amount of cells used in implantation depends on a number of various factors including the subject's condition and response to the therapy, and can be determined by one skilled in the art. For example, the number of cells administered can range from about 1000 to about $10^{12}$.

In one aspect, this invention provides a method for treating a patient suffering from, or at risk of developing a liver condition or disease. This method can involve administering any of the (induced) multipotent cells, endodermal progenitor cells, immature hepatocytes, and/or mature hepatocytes described herein. The method can also involve culturing a selected cell population (e.g., of non-hepatocytes), differentiating or redirecting the cultured cells in vitro into a endoderm lineage to generate a first cell population containing endodermal progenitor cells, differentiating the first cell population into a second cell population containing immature and/or mature hepatocytes, and administering the second population of cells to a subject. In some instances endodermal progenitor cells are expanded prior to further differentiation. In addition, the first population can be enriched by removing non-endodermal cells. Similarly, the second population can be enriched or purified to generate a third population of cells that is substantially free of non-endodermal or non-hepatocyte cells.

The cells to be administered can be incorporated into a three-dimensional support. The cells can be maintained in vitro on this support prior to implantation into the subject. Alternatively, the support containing the cells can be directly implanted in the subject without additional in vitro culturing. The support can optionally be incorporated with at least one pharmaceutical agent that facilitates the survival and function of the transplanted cells.

Support materials suitable for use include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods described herein. See, for example, the materials disclosed in U.S. Pat. No. 5,770,417, U.S. Pat. No. 6,022,743, U.S. Pat. No. 5,567,612, U.S. Pat. No. 5,759,830, U.S. Pat. No. 6,626,950, U.S. Pat. No. 6,534,084, U.S. Pat. No. 6,306,424, U.S. Pat. No. 6,365,149, U.S. Pat. No. 6,599,323, U.S. Pat. No. 6,656,488, U.S. Published Application 2004/0062753 A1, U.S. Pat. No. 4,557,264 and U.S. Pat. No. 6,333,029, each of which is specifically incorporated by reference herein in its entirety.

The mammalian subject can be a human patient, a domestic animal, or a laboratory animal.

Administration of Reprogrammed Cells

Reprogrammed cells generated as described herein can be employed for tissue reconstitution or regeneration in a human patient or other subjects in need of such treatment. The cells are administered in a manner that permits them to graft or migrate to a diseased or injured tissue site and to reconstitute or regenerate the functionally deficient area. Devices are available that can be adapted for administering cells, for example, intravascularly.

Reprogrammed cells can be administered to reconstitute the hepatocyte population in the liver. The cells may be administered to a recipient by local injection, or by systemic injection. For example, the cells can be administered intravascularly. In some embodiments, the cells can be administered parenterally by injection into a blood vessel leading to the liver, into a convenient cavity, or by intramuscular injection.

Many cell types are capable of migrating to an appropriate site for regeneration and differentiation within a subject. To determine the suitability of cell compositions for therapeutic administration, the cells can first be tested in a suitable animal model. At one level, cells are assessed for their ability to survive and maintain their phenotype in vivo. Cells can also be assessed to ascertain whether they migrate to diseased or injured sites in vivo, or to determine an appropriate number of cells to be administered. Cell compositions can be administered to immunodeficient animals (such as nude mice, or animals rendered immunodeficient chemically or by irradiation). Tissues can be harvested after a period of regrowth, and assessed as to whether the administered cells or progeny thereof are still present, are alive, and/or have migrated to desired or undesired locations.

Injected cells can be traced by a variety of methods. For example, cells containing or expressing a detectable label (such as green fluorescent protein, or beta-galactosidase) can readily be detected. The cells can be pre-labeled, for example, with BrdU or [$^3$H] thymidine, or by introduction of an expression cassette that can express green fluorescent protein, or beta-galactosidase. Alternatively, the reprogrammed cells can be detected by their expression of a cell marker that is not expressed by the animal employed for testing (for example, a human-specific antigen). The presence and phenotype of the administered population of reprogrammed cells can be assessed by fluorescence microscopy (e.g., for green fluorescent protein, or beta-galactosidase), by immunohistochemistry (e.g., using an antibody against a human antigen), by ELISA (using an antibody against a human antigen), or by RT-PCR analysis using primers and hybridization conditions that cause amplification to be specific for human polynucleotides.

A number of animal models for liver diseases are available for testing, for example, leptin receptor-deficient mice, hepatocyte-specific Pten-deficient mice, retinoic acid receptor a dominant-negative transgenic mice, animals to whom an N-acetyl-β-D-glucosaminidase inhibitor has been administered, and mice induced to have a liver condition by a special diet such as a methionine/choline-deficient diet, models available from Jackson laboratories.

A reprogrammed population of cells can be introduced by injection, catheter, implantable device, or the like. A population of reprogrammed cells can be administered in any physiologically acceptable excipient or carrier that does not adversely affect the cells.

A population of reprogrammed cells can be supplied in the form of a pharmaceutical composition. Such a composition can include an isotonic excipient prepared under sufficiently sterile conditions for human administration. For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. The choice of the cellular excipient and any accompanying constituents of the composition that includes a population of reprogrammed cells can be adapted to optimize administration by the route and/or device employed.

A composition that includes a population of reprogrammed cells can also include or be accompanied by one or more other ingredients that facilitate engraftment or functional mobilization of the reprogrammed cells. Suitable ingredients include matrix proteins that support or promote adhesion of the reprogrammed cells, or complementary cell types, such as glial and/or muscle cells. In another embodiment, the composition may include physiologically acceptable matrix scaffolds. Such physiologically acceptable matrix scaffolds can be resorbable and/or biodegradable.

The population of reprogrammed cells generated by the methods described herein can include low percentages of non-endodermal/hepatocyte cells (e.g., fibroblasts). For example, a population of reprogrammed cells for use in compositions and for administration to subjects can have less than about 90% non-endodermal/hepatocyte cells, less than about 85% non-endodermal/hepatocyte cells, less than about 80% non-endodermal/hepatocyte cells, less than about 75% non-endodermal/hepatocyte cells, less than about 70% non-endodermal/hepatocyte cells, less than about 65% non-endodermal/hepatocyte cells, less than about 60% non-endodermal/hepatocyte cells, less than about 55% non-endodermal/hepatocyte cells, less than about 50% non-endodermal/hepatocyte cells, less than about 45% non-endodermal/hepatocyte cells, less than about 40% non-endodermal/hepatocyte cells, less than about 35% non-endodermal/hepatocyte cells, less than about 30% non-endodermal/hepatocyte cells, less than about 25% non-endodermal/hepatocyte cells, less than about 20% non-endodermal/hepatocyte cells, less than about 15% non-endodermal/hepatocyte cells, less than about 12% non-endodermal/hepatocyte cells, less than about 10% non-endodermal/hepatocyte cells, less than about 8% non-endodermal/hepatocyte cells, less than about 6% non-endodermal/hepatocyte cells, less than about 5% non-endodermal/hepatocyte cells, less than about 4% non-endodermal/hepatocyte cells, less than about 3% non-endodermal/hepatocyte cells, less than about 2% non-endodermal/hepatocyte cells, or less than about 1% non-endodermal/hepatocyte cells of the total cells in the cell population.

Pharmaceutical Compositions

The invention also relates to compositions for inducing cells to the endodermal lineage that can contain one or more of the following chemical agents: an epidermal growth factor (EGF), basic fibroblast growth factor (bFGF), an activator of WNT signaling (e.g., a GSK3 inhibitor), a nuclear receptor liver receptor homolog 1 agonist, a histone deacetylase (HDAC) inhibitor, a histone demethylase LSD1 inhibitor, a DNA methyltransferase (DNMT) inhibitor, or a combination thereof. For example, the composition can contain at least two of the agents, or at least three of the agents, or at least four of the agents, or at least five of the agents, or at least six of the agents, or at least seven of the agents. The compositions can also contain reprogrammed cells, for example, induced multipotent cells, endodermal progenitor cells, endodermal cells, immature hepatocytes, or a combination thereof.

A composition useful for further differentiation of endodermal progenitor cells can include factors such as epidermal growth factor (EGF), basic fibroblast growth factor (bFGF), WNT signaling (e.g., a GSK3 inhibitor), a TGF-beta inhibitor, BMP4, hepatocyte growth factor (HGF), dexamethasone (Dex), oncostatin M (OSM), a Notch inhibitor (e.g., compound E (C-E)), or any combination thereof. For example, the composition can contain at least two of the agents, or at least three of the agents, or at least four of the agents, or at least five of the agents, or at least six of the agents, or at least seven of the agents, or at least eight of the agents, or at least nine of the agents. The compositions can also contain reprogrammed cells, for example, endodermal cells, immature hepatocytes, mature hepatocytes, or a combination thereof.

The compositions of the invention can be pharmaceutical compositions. In some embodiments, the compositions can include a pharmaceutically acceptable carrier. By "pharmaceutically acceptable" it is meant a carrier, diluent, excipient, and/or salt that is compatible with the other ingredients of the formulation, and not deleterious to the recipient thereof.

In some embodiments, the composition is a cell reprogramming composition.

The compositions can contain any of the agent(s) or compound(s) described herein in an amount sufficient to reprogram a cell into a multipotent cell type, an endodermal progenitor cell type, an endodermal cell type, an immature hepatocyte cell type, or a mature hepatocyte. For example, the compositions can contain any of the agent(s) or compound(s) described herein in an amount sufficient to induce expression of at least one endodermal progenitor cell marker such as SOX17, FOXA2, or a combination thereof. The compositions can contain any of the agent(s) or compound(s) described herein in an amount sufficient to induce expression of at least one hepatocyte marker such as α-fetoprotein (AFP), albumin (ALB), α-1 Antitrypsin (AAT), or a combination thereof. The cell contacted or treated by the compositions (whether in vitro or in vivo) can be any of the starting cells described herein. For example, the cell can be a non-endodermal cell, non-hepatocyte, and/or a differentiated cell.

In some embodiments, the therapeutic compositions are administered in a "therapeutically effective amount." Such a therapeutically effective amount is an amount sufficient to obtain the desired physiological effect, e.g., treatment of a condition, disorder, disease and the like or reduction in symptoms of the condition, disorder, disease and the like. For example, the therapeutic agents can be administered to treat a condition, disorder, or disease such as a liver disease or condition.

To achieve the desired effect(s), one or more compositions can be formulated in single or divided dosages. For example, an epidermal growth factor (EGF), basic fibroblast growth factor (bFGF), an activator of WNT signaling (e.g., a GSK3 inhibitor), a nuclear receptor liver receptor homolog 1 agonist, a histone deacetylase (HDAC) inhibitor, a histone demethylase LSD1 inhibitor, a DNA methyltransferase (DNMT) inhibitor, a TGF-beta inhibitor, BMP4, hepatocyte growth factor (HGF), dexamethasone (Dex), oncostatin M (OSM), and/or a Notch inhibitor (e.g., compound E (C-E)) can be present in the composition in the amounts specified above or in dosages of at least about 0.001 mg/kg to about 500 to 750 mg/kg, of at least about 0.01 mg/kg to about 300 to 500 mg/kg, of at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the combination of compounds chosen for administration, the disease, the weight, the physical condition, the health, the age of the mammal. Such factors can be readily determined by the clinician employing animal models or other test systems that are available in the art.

Reprogrammed cells can be included in the compositions in varying amounts depending upon the disease or injury to be treated. For example, the compositions can be prepared in liquid form for local or systemic administration containing about $10^3$ to about $10^{12}$ reprogrammed cells, or about $10^4$ to about $10^{10}$ reprogrammed cells, or about $10^5$ to about $10^8$ reprogrammed cells.

One or more of the following types of compounds can be present in a composition for inducing or reprogramming cells to an endodermal lineage: containing an epidermal growth factor (EGF), basic fibroblast growth factor (bFGF), an activator of WNT signaling (e.g., a GSK3 inhibitor), a nuclear receptor liver receptor homolog 1 agonist, a histone deacetylase (HDAC) inhibitor, a histone demethylase LSD1 inhibitor, a DNA methyltransferase (DNMT) inhibitor, or a combination thereof. Endodermal progenitor cells can be expanded in a composition that contains epidermal growth factor (EGF), basic fibroblast growth factor (bFGF), an activator of WNT signaling (e.g., a GSK3 inhibitor), and/or a TGF-beta inhibitor. A composition useful for further differentiation of cells into immature hepatocytes or more mature hepatocytes can include factors such as epidermal growth factor (EOF), basic fibroblast growth factor (bFGF), a TGF-beta inhibitor, BMP4, hepatocyte growth factor (HGF), dexamethasone (Dex), oncostatin M (OSM), a Notch inhibitor (e.g., compound E (C-E)), or a combination.

Administration of the composition may be in a single dose, in multiple doses, in a continuous or intermittent manner, depending, for example, upon the recipient's physiological condition, whether the purpose of the administration is administered in response to traumatic injury or for more sustained therapeutic purposes, and other factors known to skilled practitioners. Both local and systemic administration is contemplated.

The administration or contacting cells with the compounds and compositions of the invention may be essentially continuous over a preselected period of time or may be in a series of spaced doses.

To prepare the composition, the compounds are synthesized and/or the cells are generated, and the components are purified as necessary or desired. The compounds, cells, and/or other agents can be suspended in a pharmaceutically acceptable carrier. If the composition contains only compounds, without cells, the composition can be lyophilized. These compounds and cells can be adjusted to an appropriate concentration, and optionally combined with other agents. The absolute weight of a given compound and/or other agent included in a unit dose can vary widely. For example, about 0.01 to about 2 g, or about 0.1 to about 500 mg, of at least one compound can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the compounds can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

It will be appreciated that the amount of compounds and cells for use in treatment will vary not only with the particular carrier selected but also with the route of administration, the nature of the condition being treated and the age and condition of the patient, Ultimately, the attendant health care provider may determine proper dosage. A pharmaceutical composition may be formulated with the appropriate ratio of each compound in a single unit dosage form for administration with or without cells. Cells can be separately provided and either mixed with a liquid solution of the compound composition, or administered separately.

The compounds can also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof and then, if necessary, introducing or shaping the product into the desired delivery system.

One or more suitable unit dosage forms containing the compounds and/or the reprogrammed cells can be administered by a variety of routes including parenteral (including subcutaneous, intravenous, intramuscular and intraperitoneal), intracranial, intraspinal, oral, rectal, dermal, transdermal, intrathoracic, intrapulmonary and intranasal (respiratory) routes.

The compositions of the invention may be prepared in many forms that include aqueous solutions, suspensions, tablets, hard or soft gelatin capsules, and liposomes and other slow-release formulations, such as shaped polymeric gels. However, administration of cells often involves parenteral or local administration in an aqueous solution. Similarly, compositions containing cells and/or compounds can be administered in a device, scaffold, or as a sustained release formulation.

Thus while compositions containing only compounds can be administered in an oral dosage form, compositions containing cells are administered locally or systemically as non-oral formulations. When compositions contain only compounds, those compositions can be formulated as oral dosage form so that the compounds are released into the stomach for quick absorption or in the intestine after passing through the stomach. Different types of formulating procedures are described in U.S. Pat. No. 6,306,434 and in the references contained therein.

Liquid pharmaceutical compositions may be in the form of, for example, aqueous or oily suspensions, solutions, emulsions, syrups or elixirs, dry powders for constitution with water or other suitable vehicles before use. Such liquid pharmaceutical compositions may contain conventional additives such as suspending agents, emulsifying agents, non-aqueous vehicles (which may include edible oils), or preservatives.

Compounds and/or cells can be formulated for parenteral administration (e.g., by injection, for example, bolus injection or continuous infusion) and may be presented in unit dosage form in ampoules, prefilled syringes, small volume infusion containers or multi-dose containers with an added preservative. The pharmaceutical compositions can take the form of suspensions, solutions, or emulsions in oily or aqueous vehicles, and can contain formulatory agents such as suspending, stabilizing and/or dispersing agents. Suitable carriers include saline solution, phosphate buffered saline, and other materials commonly used in the art.

The compositions can also contain other ingredients such as agents useful for treatment of liver conditions, diseases and injuries, such as, for example, interferon, corticosteroids, pentoxifylline, antibiotics, vitamins, amino acids (e.g., valine), nucleoside analogs, nucleotide analogs, S-adenosylmethionine, selenium, betaine, ursodeoxycholic acid, carnosine, carnosine salt (e.g., carnosine zinc salt), milk thistle, cholestyramine (Questran, Prevalite), rifampin (Rifadin), naltrexone (ReVia, Depade), antihistamines, 4-β-chloro-4-(cyclopropylaminocarbonyl)aminophenoxy)-7-methoxy-6-quinolinecarboxamide, erythropoietin, and combinations thereof. Additional agents can also be included such as antibacterial agents, antimicrobial agents, anti-viral, biological response modifiers, growth factors; immune modulators, monoclonal antibodies and/or preservatives. The compositions of the invention may also be used in conjunction with other forms of therapy.

Supplementary factors can be included in the compositions and/or in a cell culture media containing any of the compositions, compounds or agents described herein. Examples of such supplementary factors include bone morphogenic protein (BMP)-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, brain derived neurotrophic factor, ciliary neurotrophic factor, cytokine-induced neutrophil chemotactic factor 1, cytokine-induced neutrophil chemotactic factor 2a, cytokine-induced neutrophil chemtotactic factor 2β, β endothelial cell growth factor, endothelin 1, epidermal growth factor, epithelial-derived neutrophil attractant, fibroblast growth factor (FGF) 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor (acidic), fibroblast growth factor (basic) growth related protein, growth related protein α, growth related protein β, growth related protein γ, heparin binding epidermal growth factor, hepatocyte growth factor, insulin-like growth factor I, insulin-like growth factor II, insulin-like growth factor binding protein, keratinocyte growth factor, leukemia inhibitory factor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, pre-B cell growth stimulating factor, stem cell factor, transforming growth factor a, transforming growth factor β, transforming growth factor β1, transforming growth factor 01.2, transforming growth factor 132, transforming growth factor β3, latent transforming growth factor β1, transforming growth factor 1 binding protein I, transforming growth factor β binding protein II, transforming growth factor β binding protein II, and vascular endothelial growth factor.

Exemplary cytokines can be included such as interleukin (IL)-1, IL-2, IL-3, IL-4, L-5, IL-6, IL-7, IL-6, IL-7, IL-8, IL-9, IL-10, IL-11, L-12, IL-13, IL-14, IL-15, IL-16, IL-17, IL-18, interferon (IFN), IFN-γ, tumor necrosis factor (TNF), TNF1, TNF2, TNF-α, macrophage colony stimulating factor (M-CSF), granulocyte-monocyte colony stimulating factor (GM-CSF), granulocyte colony stimulating factor (G-CSF), megakaryocyte colony stimulating factor (Meg-CSF)-thrombopoietin, stem cell factor, and erythropoietin. Chemokines can also be included such as IP-10 and Stromal Cell-Derived Factor 1α.

Exemplary hormones contemplated for inclusion in the compositions and/or cell culture media described herein can include, but are not limited to, steroid hormones and peptide hormones, such as insulin, somatostatin, growth hormone, hydrocortisone, dexamethasone, 3,3',5-Triiodo-L-thyronine, and L-Thyroxine.

Kits

A variety of kits are described herein that include any of the compositions, compounds and/or agents described herein. The compounds and/or agents described herein can be packaged separately into discrete vials, bottles or other containers. Alternatively, any of the compounds and/or agents described herein can be packaged together as a single composition, or as two or more compositions that can be used together or separately. The compounds and/or agents described herein can be packaged in appropriate ratios and/or amounts to facilitate conversion of selected cells across differentiation boundaries to form multipotent cells, endodermal cells, immature hepatocytes, and/or mature hepatocytes.

A kit is described herein for culture of cells in vitro that can include any of the compositions, compounds and/or agents described herein, as well as instructions for using those compositions, compounds and/or agents. Some kits can include a cell culture or cell media that includes any of the compositions, compounds and/or agents described herein. The kits can include one or more sterile cell collection devices such as a swab, skin scrapping device, a needle, a syringe, and/or a scalpel. The kits can also include antibodies for detection of multipotent cell markers, and/or antibodies for detection of endodermal cell markers such as SOX17, FOXA2, or a combination thereof. The kits can further include antibodies for detection of hepatocyte markers such as α-fetoprotein (AFP), albumin (ALB), α-1 Antitrypsin (AAT), or a combination thereof. The antibodies can be labeled so that a detectable signal can be observed when the antibodies form a complex with such cell marker(s).

The instructions can include guidance for culturing cells for a time and under conditions sufficient to convert a selected cell across differentiation boundaries and into an endodermal cell, an immature hepatocyte, and/or a hepatocyte. For example, the instructions can describe amounts of the compositions, compounds and/or agents described herein to add to cell culture media, and times sufficient to convert cells to endodermal cells, immature hepatocytes, and/or hepatocytes. The instructions can describe amounts of the compositions, compounds and/or agents described herein to add to cell culture media, times sufficient to maintain appropriate cell densities for optimal conversion, and the like. For example, the instructions can describe procedures for rehydration or dilution of the compositions, compounds and/or agents described herein. When a kit provides a cell culture medium containing some of the compositions, compounds and/or agents described herein, the instructions can describe how to add other compounds and/agents, if any to the medium. The instructions can also describe how to expand multipotent cells, endodermal cells and/or immature hepatocytes into a larger population of multipotent cells, endodermal cells and/or immature hepatocytes.

The instructions can also describe procedures for detecting multipotent cell markers, endodermal cell markers, and/or hepatocyte markers by use of the antibodies against those markers so that the extent of conversion and/or differentiation can be assessed.

Another kit is also described herein that includes any of the compositions, compounds and/or agents described herein for therapeutic treatment of a subject. The kit can include any of the compositions, compounds and/or agents described herein, as well as instructions for administering those compositions, compounds and/or agents. Such instructions can provide the information described throughout this application. The kit can also include cells. For example, the kit can include induced multipotent cells, endodermal cells, or hepatocytes that have been treated by the methods described herein and that are ready for administration.

The cells, compositions and/or compounds can be provided within any of the kits in a delivery device. Alternatively a delivery device can be separately included in the kit(s), and the instructions can describe how to assemble the delivery device prior to administration to a subject. The delivery device can provide a scaffold for cell growth and/or a matrix for controlled release of any of the compositions, compounds or agents described herein.

Any of the kits can also include syringes, catheters, scalpels, sterile containers for sample or cell collection, diluents, pharmaceutically acceptable carriers, and the like.

The kits can provide other factors such as any of the supplementary factors described herein for the compositions in the preceding section.

Definitions

As used herein, the term "treating" and "treatment" refers to administering to a subject an effective amount of a composition so that the recipient has a reduction in at least one symptom of the disease or an improvement in the disease, for example, beneficial or desired therapeutic or clinical results. For purposes of this invention, beneficial or desired therapeutic or clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether empirically detectable or undetectable. Treating can refer to prolonging survival as compared to expected survival if not receiving treatment. Thus, one of skill in the art realizes that a treatment may improve the disease condition, but may not be a complete cure for the disease. The term "treatment" includes prophylaxis. Treatment is "effective" if the progression of a disease is reduced or halted. "Treatment" can also mean prolonging survival as compared to expected survival if not receiving treatment. Those in need of treatment include those already diagnosed with a condition (e.g., a liver condition such as chronic liver failure), as well as those likely to develop a condition due to genetic susceptibility or other factors such as alcohol consumption, diet, toxic exposure, and health.

An "Oct polypeptide" refers to any of the naturally-occurring members of Octamer family of transcription factors, or variants thereof that maintain transcription factor activity, similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Oct polypeptides include Oct-1, Oct-2, Oct-3/4, Oct-6, Oct-7, Oct-8, Oct-9, and Oct-11, Oct3/4 (referred to herein as "Oct4") contains the POU domain, a 150 amino acid sequence conserved among Pit-1, Oct-1, Oct-2, and uric-86. See, Ryan, A. K. & Rosenfeld, M. G., *Genes Dev.* 11, 1207-1225 (1997). In some embodiments, variants have at least 85%, 90%, or 95% amino acid sequence identity across their whole sequence compared to a naturally occurring Oct polypeptide family member such as to those listed above or such as listed in Genbank accession number NP-002692.2 (human Oct4) or NP-038661.1 (mouse Oct4). Oct polypeptides (e.g., Oct3/4 or Oct 4) can be from human, mouse, rat, bovine, porcine, or other animals. Generally, the same species of protein will be used with the species of cells being manipulated. The Oct polypeptide(s) can be a pluripotency factor that can help induce multipotency in non-pluripotent cells.

A "Klf polypeptide" refers to any of the naturally-occurring members of the family of Krüppel-like factors (Klfs), zinc-finger proteins that contain amino acid sequences similar to those of the *Drosophila* embryonic pattern regulator Krüppel, or variants of the naturally-occurring members that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. See, Dang, D. T., Pevsner, J. & Yang, V. W., *Cell Biol.* 32, 11.03-1121 (2000). Exemplary Klf family members include, Klf1, Klf2, Klf3, Klf-4, Klf5S, Klf6, Klf7, Klf8, Klf9, Klf10, Klf11, Klf12, Klf13, Klf14, Klf15, Klf16, and Klf17, Klf2 and Klf-4 were found to be factors capable of generating iPS cells in mice, and related genes Klf1 and Klf5 did as well, although with reduced efficiency. See, Nakagawa, et al., *Nature Bioteehnology* 26:101-106 (2007). In some embodiments, variants have at least 85%, 90%, or 95% amino acid sequence identity across their whole sequence compared to a naturally occurring Klf polypeptide family member such as to those listed above or such as listed in Genbank accession number CAX16088 (mouse Klf4) or CAX14962 (human Klf4). Klf polypeptides (e.g., Klf1, Klf4, and Klf5) can be from human, mouse, rat, bovine, porcine, or other animals. Generally, the same species of protein will be used with the species of cells being manipulated. The Klf polypeptide(s) can be a pluripotency factor. The expression of the Klf4 gene or polypeptide can help induce multipotency in a starting cell or a population of starting cells.

A "Myc polypeptide" refers to any of the naturally-occurring members of the Myc family (see, e.g., Adhikary, S. & Eilers, M., *Nat. Rev. Mol. Cell Biol.* 6:635-645 (2005)), or variants thereof that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. Exemplary Myc polypeptides include, e.g., c-Myc, N-Myc and L-Myc. In some embodiments, variants have at least 85%, 90%, or 95% amino acid sequence identity across their whole sequence compared to a naturally occurring Myc polypeptide family member, such as to those listed above or such as listed in Genbank accession number CAA25015 (human Myc). Myc polypeptides (e.g., c-Myc) can be from human, mouse, rat, bovine, porcine, or other animals. Generally, the same species of protein will be used with the species of cells being manipulated. The Myc polypeptide(s) can be a pluripotency factor. However, as illustrated herein, Myc expression need not be present and need not be induced to induce multipotency in a starting cell.

A "Sox polypeptide" refers to any of the naturally-occurring members of the SRY-related HMG-box (Sox) transcription factors, characterized by the presence of the high-mobility group (HMG) domain, or variants thereof that maintain transcription factor activity similar (within at least 50%, 80%, or 90% activity) compared to the closest related naturally occurring family member, or polypeptides comprising at least the DNA-binding domain of the naturally occurring family member, and can further comprise a transcriptional activation domain. See, e.g., Dang, D. T. et al., *Int. J. Biochem, Cell Biol.* 32:1103-1121 (2000). Exemplary Sox polypeptides include, e.g., Sox1, Sox-2, Sox3, Sox4, Sox5, Sox6, Sox7, Sox8, Sox9, Sox10, Sox11, Sox12, Sox13, Sox14, Sox15, Sox17, Sox18, Sox-21, and Sox30, Sox1 has been shown to yield iPS cells with a similar efficiency as Sox2, and genes Sox3, Sox115, and Sox18 have also been shown to generate iPS cells, although with somewhat less efficiency than Sox2. See, Nakagawa, et al., *Nature Biotechnology* 26:101-106 (2007). In some embodiments, variants have at least 85%, 90%, or 95% amino acid sequence identity across their whole sequence compared to a naturally occurring Sox polypeptide family member such as to those listed above or such as listed in Genbank accession number CAA83435 (human Sox2). Sox polypeptides (e.g., Sox1, Sox2, Sox3, Sox15, or Sox18) can be from human, mouse, rat, bovine, porcine, or other animals. Generally, the same species of protein will be used with the species of cells being manipulated. The Sox polypeptide(s) can be a pluripotency factor. The expression of the Klf4 gene or polypeptide can help induce multipotency in a starting cell or a population of starting cells.

The term "pluripotent" or "pluripotency" refers to cells with the ability to give rise to progeny cells that can undergo differentiation, under the appropriate conditions, into cell types that collectively demonstrate characteristics associated with cell lineages from all of the three germinal layers (endoderm, mesoderm, and ectoderm). Pluripotent stem cells can contribute to all embryonic derived tissues of a prenatal, postnatal or adult animal. A standard art-accepted test, such as the ability to form a teratoma in 8-12 week old SCID mice, can be used to establish the pluripotency of a cell population. However, identification of various pluripotent stem cell characteristics can also be used to detect pluripotent cells.

"Pluripotent stem cell characteristics" refer to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Expression or non-expression of certain combinations of molecular markers are also pluripotent stem cell characteristics. For example, human pluripotent stem cells express at least several, and in some embodiments, all of the markers from the following non-limiting list: SSEA-3, SSEA-4, TRA-1-60, TRA-1-81, TRA-2-49/6E, ALP, Sox2, E-cadherin, UTF-1, Oct4, Rex1, and Nanog. Cell morphologies associated with pluripotent stem cells are also pluripotent stem cell characteristics. As described herein, cells do not need to pass through pluripotency to be reprogrammed into endodermal progenitor cells and/or hepatocytes. The induced multipotent cells generated by the methods described herein do not exhibit pluripotent stem cell characteristics.

As used herein, "multipotent" or "multipotent cell" refers to a cell type that can give rise to a limited number of other particular cell types. For example, induced multipotent cells are capable of forming endodermal cells.

As used herein, the term "oligopotent" refers to the ability of an adult stem cell to differentiate into only a few different cell types. For example, lymphoid or myeloid stem cells are capable of forming cells of either the lymphoid or myeloid lineages, respectively.

As used herein, the term "unipotent" means the ability of a cell to form a single cell type. For example, spermatogonial stem cells are only capable of forming sperm cells.

As used herein, the term "totipotent" means the ability of a cell to form all cell lineages of an organism. For example, in mammals, only the zygote and the first cleavage stage blastomeres are totipotent.

As used herein, "non-pluripotent cells" refer to mammalian cells that are not pluripotent cells. Examples of such cells include differentiated cells as well as progenitor cells. Examples of differentiated cells include, but are not limited to, cells from a tissue selected from bone marrow, skin, skeletal muscle, fat tissue and peripheral blood. Exemplary cell types include, but are not limited to, fibroblasts, hepatocytes, myoblasts, neurons, osteoblasts, osteoclasts, and T-cells. The starting cells employed for generating the induced multipotent cells, the endodermal progenitor cells, and the hepatocytes can be non-pluripotent cells.

Where an individual is to be treated with induced endoderm cells, and/or hepatocytes, the individual's own non-pluripotent cells can be used to generate induced endoderm cells, and/or hepatocytes according to the methods of the invention.

Mammalian cells can be from humans or non-human mammals. Exemplary non-human mammals include, but are not limited to, mice, rats, cats, dogs, rabbits, guinea pigs, hamsters, sheep, pigs, horses, bovines, and non-human primates (e.g., chimpanzees, macaques, and apes).

"Inhibitors," "activators," and "modulators" of expression or of activity are used to refer to inhibitory, activating, or modulating molecules, respectively, identified using in vitro and in vivo) assays for expression or activity of a described target protein (or encoding polynucleotide), e.g., ligands, agonists, antagonists, and their homologs and mimetics. The term "modulator" includes inhibitors and activators. Inhibitors are agents that, e.g., inhibit expression or bind to, partially or totally block stimulation or protease inhibitor activity, reduce, decrease, prevent, delay activation, inactivate, desensitize, or down regulate the activity of the described target protein, e.g., antagonists. Activators are agents that, e.g., induce or activate the expression of a described target protein or bind to, stimulate, increase, open, activate, facilitate, enhance activation or protease inhibitor activity, sensitize or up regulate the activity of described target protein (or encoding polynucleotide), e.g., agonists. Modulators include naturally occurring and synthetic ligands, antagonists and agonists (e.g., small chemical molecules, antibodies and the like that function as either agonists or antagonists). Such assays for inhibitors and activators include, e.g., applying putative modulator compounds to cells expressing the described target protein and then determining the functional effects on the described target protein activity, as described above. Samples or assays comprising described target protein that are treated with a potential activator, inhibitor, or modulator are compared to control samples without the inhibitor, activator, or modulator to examine the extent of effect. Control samples (untreated with modulators) are assigned a relative activity value of 100%. Inhibition of a described target protein is achieved when the activity value relative to the control is about 80%, optionally 50% or 25%, 10%, 5% or 1%. Activation of the described target protein is achieved when the activity value relative to the control is 110%, optionally 150%, optionally 200%, 300%, 400%, 500%, or 1000-3000% or more higher.

As used herein, a "differentiated non-hepatic cell" may refer to a cell that is not able to differentiate into all cell types of an adult organism (i.e., is not a pluripotent cell), and which is of a cellular lineage other than a hepatocyte lineage (e.g., a hematopoietic lineage or a connective tissue lineage).

Differentiated cells include, but are not limited to, multipotent cells, oligopotent cells, unipotent cells, progenitor cells, and terminally differentiated cells. In particular embodiments, a less potent cell is considered "differentiated" in reference to a more potent cell.

As used herein, a cell that differentiates into a mesodermal, ectodermal or endodermal lineage defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoietic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to pleurigenic cells, and hepatogenic cells, that give rise to the lining of the intestine, and cells that give rise to pancreogenic and splanchogenic cells.

A "somatic cell" is a cell forming the body of an organism. Somatic cells include cells making up organs, skin, blood, bones and connective tissue in an organism, but not germ cells.

Cells can be from, for example, human or non-human mammals. Exemplary non-human mammals include, but are not limited to, mice, rats, cats, dogs, rabbits, guinea pigs, hamsters, sheep, pigs, horses, bovines, and non-human primates. In some embodiments, a cell is from an adult human or non-human mammal. In some embodiments, a cell is from a neonatal human, an adult human, or non-human mammal.

As used herein, the term "direct reprogramming" or "transdifferentiation" refers to the generation of a cell of a certain lineage (e.g., an endodermal cell) from a different type of cell (e.g., a fibroblast cell) without an intermediate process of de-differentiating the cell into a cell exhibiting pluripotent stem cell characteristics.

As used herein, the terms "subject" or "patient" refers to any animal, such as a domesticated animal, a zoo animal, or a human. The "subject" or "patient" can be a mammal like a dog, cat, bird, livestock, or a human. Specific examples of "subjects" and "patients" include, but are not limited to, individuals with a liver disease, condition, or disorder, and individuals with liver disorder-related characteristics or symptoms.

The following non-limiting Examples illustrate some of the experimental work involved in developing the invention.

Example 1: Materials and Methods

This Example describes some of the materials and methods employed in development of the invention.

Cell Culture Media

Reprogramming Initiation Medium (RIM): DMEM/F12, 10% Knockout Serum Replacement (KSR), 5% ES-FBS, 1% Glutamax, 1% Non-Essential Amino Acids (NEAA), 1% Penicillin/Streptomycin (P/S), 0.1 mM β-mercaptoethanol (β-ME), 10 ng/mL bFGF, and 10 ng/mL EGF.

Endoderm Differentiation Medium (EDM): Advanced RPM, 2% ES-FBS, 1% Glutamax, 1% NEAA, 1% Penicillin/Streptomycin, and 0.1 mM β-mercaptoethanol.

Endoderm Expansion Medium (EEM): DMEM, 1% Glutamax, 0.5×N2, 0.54×B27 (without vitamin A), 5 μg/mL BSA, 1% P/S, 3 μM CHIR, 10 ng/mL bFGF, 10 ng/mL EGF, and 0.5 μM A83.

All cell culture reagents were from Invitrogen and all chemicals and all growth factors were from Stemgent except where otherwise specified.

Generation of iMPC-EPCs from Fibs

Human newborn fibroblasts (CRL-2097, ATCC) were cultured in a 10-cm tissue culture dish coated with 0.1 gelatin, and transduced twice with freshly produced retrovirus supernatants capable of expressing OCT4, SOX2, and KLF4 as described by Takahashi et al., *Cell* 131, 861-872, (2007) and Lin et al., *Nat Methods* 6, 805-808, (2009).

For reprogramming, $1\times10^4$ transduced cells were seeded in a 10-cm tissue culture dish coated with 0.1 gelatin, and cultured in the reprogramming initiation medium (RIM) supplemented with 3 μM CHIR99021 (CHIR), 100 μM dilauroyl phosphatidyl-choline (DLPC; Tocris), 0.1 mM Na Butyrate (NaB), 2 μM Parnate (Par), and 0.5 μM RG108 (RG) for 1 week, followed by treatment with endoderm differentiation medium (EDM) supplemented with 3 μM CHIR, 100 μM DLPC, 0.1 mM NaB, 2 μM Par, 0.5 μM RG, and 100 ng/mL Activin A for 2-3 weeks. Reprogrammed colonies were picked at day 21-28 for expansion on passage 4 irradiated CF1 mouse embryonic fibroblasts (MEFs) in endoderm expansion medium (EEM), and were passaged at a ratio of 1:4-1:6 after Accutase dissociation. To prevent cell death, 0.5 μM thiazovivin was added to the medium in the first 12-24 hours after each passage.

Generation of iMPC-Heps from iMPC-EPCs iMPCs were cultured in EEM for 4-5 days, then in hepatocyte differentiation medium (HDM) supplemented with 20 ng/mL BMP4, 20 ng/mL bFGF, 0.1 μM Dex, and 0.5 μM A83 for 4 days, and then in hepatocyte maturation medium (HMM), consisting of HCM (Hepatocyte Culture Medium, Lonza) supplemented with 20 ng/mL HGF, 20 ng/mL OSM, 0.1 μM Dex, 0.5 μM A83, and 0.1 μM C-E, for another 7-10 days. iMPC-Heps were passaged at a ratio of 1:4 using Accutase, and cultured in HCM until use for analysis or transplantation. HDM: DMEM, 1% Glutamax, 1×B27, and 1% P/S.

Generation of DECs and GECs from ESCs

H9 ESCs were cultured on matrigel (1:50 dilution) coated 6-well plates with Essential 8 Medium (Invitrogen) for 3 days. For endoderm differentiation, cells were cultured in RPMI 1640, 1% Glutamax, 1% P/S, 100 ng/mL Activin A, and 3 μM CHIR for 1 day. RPMI 1640, 1% Glutamax, 0.2% ES-FBS, 1% P/S, and 100 ng/mL Activin A for 2 days, followed by DMEM/FI 2, 1% Glutamax, 2% ES-FBS, 1% P/S, 25 ng/mL FGF7, and 25 ng/mL FGF10 for 3 days. Cell populations at day 3 and day 6 of differentiation were considered ESC-DECs and ESC-GECs, respectively.

Generation of iPSC-Heps

Normal donor iPSCs grown on passage 3 irradiated CF1 MEFs were differentiated into DECs as described by Ma et al. (*Stem Cells Transl Med* 2, 409-419, (2013)) for 5-7 days with the substitution of insulin-free 827 medium (Invitrogen) instead of FBS. DECs were differentiated directly (without splitting) into iPSC-Heps by culturing in Iscove's modified Dulbecco's medium (Invitrogen) containing B27 with insulin (Invitrogen), 1% Glutamax (Invitrogen), 0.3 mM monothioglycerol (Sigma-Aldrich), 1% Antibiotic-Antimycotic (Invitrogen), 0.126 U/mL human insulin (Sigma-Aldrich), 100 nM Dex (Sigma-Aldrich), and supplemented with BMP4 (20 ng/mL) and bFGF (10 ng/mL), for 5 days.

Maturation was continued in the same medium and growth factors with the addition of HGF (20 ng/mL) for 15-20 days before switching to HCM (Lonza) supplemented with OSM (20 ng/mL) and HGF (20 ng/mL) for 5 to 7 days using procedures similar to those reported by Si-Tayeb et al. (*Hepatology* 51, 297-305, (2010)) and Ma et al. (*Stem Cells Transl Med* 2, 409-419, (2013)). All growth factors were purchased from R&D. Differentiation was performed entirely at 37° C. in 5% $O_2$/5% $CO_2$ with daily media changes.

Reprogramming Using Temporally Controlled Transcription Factor Overexpression

Dox-inducible lentiviruses carrying the reprogramming factors OCT4, SOX2, and KLF4 (Maherali et al., *Cell Stem Cell* 3, 340-345, (2008)) were employed. CRL-2097 fibroblasts were cultured in a 10-cm tissue culture dish coated with 0.1% gelatin, and transduced twice with freshly produced Dox-inducible lentivirus supernatants carrying the reprogramming factors OCT4, SOX2, and KLF4 (Maherali et al., *Cell Stem Cell* 3, 340-345, (2008)) using procedures as described by Zhu et al. (*Cell Stem Cell* 7: 651-655, (2010)).

For iMPC-EPC reprogramming, $1\times10^4$ transduced cells were seeded in a 10-cm tissue culture dish coated with 0.1% gelatin, and cultured in RIM supplemented with 4 μg/ml Dox, 3 μM CHIR, 100 μM DLPC, 0.1 μM NaB, 2 μM Par, and 0.5 μM RG for 7 days, 10 days, or 14 days, followed by treatment with EDM supplemented with 3 μM CHIR, 100 μM DLPC, 0.1 mM NaB, 2 μM Par, 0.5 μM RG, and 100 ng/mL Activin A for 14 days, 11 days, or 7 days, respectively.

For iPSC reprogramming, $1\times10^4$ transduced cells were seeded in a 10-cm tissue culture dish, and cultured in RIM supplemented with 4 μg/ml Dox, 3 μM CHIR, 100 μM DLPC, 0.1 mM NaB, 2 μM Par, and 0.5 μM RG for 7 days, 10 days, or 14 days, followed by treatment with iPSC medium (iPSCM) for 23 days, 20 days, or 16 days, respectively. iPSCM: DMEM/F12, 1% Glutamax, 20% KSR, 1% NEAA, 1% P/S, 0.1 mM β-ME, and 10 ng/mL bFGF.

Generation of iPSC-Heps with the iMPC-EPC/Hep Generation Protocol

Normal donor iPSCs were grown on passage 4 irradiated CF1 MEFs in iPSC medium for 3 days, and then treated with EDM supplemented with 3 μM CHIR, 100 μM DLPC, 0.1 mM NaB, 2 μM Par, and 0.5 μM RG, and 100 ng/mL Activin A for 2 weeks. After Accutase dissociation, the resulting cells were passaged at a ratio of 1:4 onto irradiated CF1 MEFs and cultured in EEM for 4 days. Next, the cells were cultured in HDM supplemented with 20 ng/mL BMP4, 20 ng/mL bFGF, 0.1 μM Dex, and 0.5 μM A83 for 4 days, and finally in HMM, consisting of HCM supplemented with 20 ng/mL HGF, 20 ng/mL OSM, 0.1 μM Dex, 0.5 μM A83, and 0.1 μM C-E, for another 10 days.

Cell Immunostaining

Standard immunostaining was carried out as previously reported. Secondary antibodies were Alexa Fluor 488/555 donkey anti-mouse or anti-rabbit or anti-goat IgG (1:1,000) (Invitrogen). Nuclei were visualized by Hoechst (Sigma-Aldrich) staining. Images were captured using a Nikon Eclipse TE2000-U microscope.

Flow Cytometry

Cells were harvested by Accutase dissociation at 37° C. for 2-5 minutes, and fixed with 4% formaldehyde in D-PBS (Sigma-Aldrich) on ice for 10 minutes. Afterwards, cells were washed 5 times with ice-cold Perm/Wash buffer (BD). To remove undissociated cell clusters, cells were passed twice through 70 μm-cell strainers (BD). For TRA-1-60 immunostaining, cells were aliquoted and incubated with PE-conjugated anti-TRA-1-60 antibody (Biolegend) diluted 1:50 on ice for 2 hours. For other immunostainings, cells were aliquoted and incubated individually with anti-HNF4α antibody (Perseus Proteomics) diluted 1:100, anti-ALB antibody (Bethyl) diluted 1:100, and anti-CK18 antibody (Abcam) diluted 1:100 on ice fir 2 hours. To determine background levels of each immunostaining, cell aliquots were incubated with the respective isotype control antibodies. After immunostaining, cells were washed 5 times with Perm/Wash buffer. Cells were then incubated individually with Alexa Fluor 488-conjugated or Alexa Fluor 555-conjugated antibodies (Invitrogen) diluted 1:500 on ice for 1 hour. Afterwards cells were washed 5 times with Perm/Wash buffer. Finally, cells were resuspended in 0.5 mL ice-cold D-PBS supplemented with 2% FBS, and flow cytometry was performed on a FACSCalibur system using CellQuest software (BD). FlowJo software (Tree Star) was used to analyze the data.

qRT-PCR

For qRT-PCR analysis, total RNA was extracted using the miRNeasy Mini Kit (Qiagen) or RNeasy Plus Mini Kit in combination with QIAshredder (Qiagen). First-strand reverse transcription was performed with 0.5-1 μg RNA using the iScript cDNA Synthesis Kit (BioRad) or qScript cDNA Supermix (Quanta Biosciences). qRT-PCR was performed using PerfeCTa SYBR Green SuperMix (Quanta) or iQ SYBR Green Supermix (Bio-Rad) on an Applied Biosciences ViiA 7 Real-Time PCR System (Invitrogen). aHeps purchased from Yecuris or the Liver Tissue Cell Distribution System (LTCDS) were shipped overnight in suspension, centrifuged for 5 minutes at 300×g immediately after arrival, and stored as cell pellets at −80° C. prior to RNA extraction. Mouse aHeps and fHeps were isolated at 12 weeks of age and embryonic day 13.5, respectively, Primer sequences are shown below. Human gene-specific primers were derived from publicly available information and are labeled "hs".

| Gene name | Forward primer (5'-3') | Reverse primer (5'-3') |
|---|---|---|
| AFP | GCGAGGGAGCGGCTG ACATT SEQ ID NO: 2 | AGCACTGGCCAACACC AGGG SEQ ID NO: 3 |
| hsAFP | GGCCTCTTCCAGAAA CTAGG SEQ ID NO: 4 | CCACAGGCCAATAGTT TGTC SEQ ID NO: 5 |
| ALB | AAGCTGCCTGCCTGTT GCCAA SEQ ID NO: 6 | GGCGAGCTACTGCCCA TGCTT SEQ ID NO: 7 |
| hsALB | ATGGATGATTTCGCA GCTTT SEQ ID NO: 8 | TGGCTTTACACCAACG AAAA SEQ ID NO: 9 |
| hsB2M | ACTGAATTCACCCCC ACTGA SEQ ID NO: 10 | CCTCCATGATGCTGCTT ACA SEQ ID NO: 11 |
| BRY | AATTGGTCCAGCCTT GGAAT SEQ ID NO: 12 | CGTTGCTCACAGACCA CA SEQ ID NO: 13 |
| CEBPA | CTCGAGGCTTGCCAG CCGT SEQ ID NO: 14A | GCGGGCTTGTCGGGAT CTCAG SEQ ID NO: 15 |
| CEBPB | GCCCTCGCAGGTCAA GAGCA SEQ ID NO: 16 | TTGAACAAGTTCCGCA GGGTG SEQ ID NO: 17 |
| CYP1A1 | TGGATGAGAACGCCA ATGTC SEQ ID NO: 18 | TGGGTTGACCCATAGC TTCT SEQ ID NO: 19 |
| hsCYP1A1 | AAACCAGTGGCAGAT CAACC SEQ ID NO: 20 | GCCCATGCCAAAGATA ATCACC SEQ ID NO: 21 |
| CYP1A2 | CAATCAGGTGGTGGT GTCAG SEQ ID NO: 22 | GCTCCTGGACTGTTTTC TGC SEQ ID NO: 23 |
| hsCYP1A2 | TGGAGACCTTCCGAC ACTCCT SEQ ID NO: 24 | CGTTGTGTCCCTTGTTG TGC SEQ ID NO: 25 |
| CYP2B6 | GGCACACAGGCAAGT TTACA SEQ ID NO: 26 | CCAGCAAAGAAGAGCG AGAG SEQ ID NO: 27 |
| hsCYP2B6 | TTCCTACTGCTTCCGT CTATCAAA SEQ ID NO: 28 | GTGCAGAATCCCACAG CTCA SEQ ID NO: 29 |
| CYP2C9 | GGACAGAGACGACAA GCACA SEQ ID NO: 30 | TGGTGGGAGAAGGTC AAT SEQ ID NO: 31 |
| CYP2C19 | ACTTGGAGCTGGGAC AGAGA SEQ ID NO: 32 | CATCTGTGTAGGGCAT GTGG SEQ ID NO: 33 |
| CYP2D6 | CGCATCCCTAAGGGA ACGA SEQ ID NO: 34 | TTCCAGACGGCCTCATC CT SEQ ID NO: 35 |
| CYP3A4 | TGTGCCTGAGAACAC CAGAG SEQ ID NO: 36 | GCAGAGGAGCCAAATC TACC SEQ ID NO: 37 |
| hsCYP3A4 | CTTCATCCAATGGACT GCATAAAT SEQ ID NO: 38 | TCCCAAGTATAACACT CTACACAGACAA SEQ ID NO: 39 |

-continued

| Gene name | Forward primer (5'-3') | Reverse primer (5'-3') |
|---|---|---|
| CYP3A7 | CCTTACCCCAATTCTT GAAGCA SEQ ID NO: 40 | TCCAGATCAGACAGAG CTTTGTG SEQ ID NO: 41 |
| hsCYP3A7 | GATCTCATCCCAAAC TTGGCCG SEQ ID NO: 42 | CATAGGCTGTTGACAG TCATAAATA SEQ ID NO: 43 |
| CYP7A1 | CACTTTGTCCACCTTT GATG SEQ ID NO: 44 | GCTGCTTTCATTGCTTC TG SEQ ID NO: 45 |
| FAH | CTGACCATTCCCCAG GTCTA SEQ ID NO: 46 | ATGGCTTCTCATCGTCT GCT SEQ ID NO: 47 |
| FOXA2 | GACAAGTGAGAGAGC AAGTG SEQ ID NO: 48 | ACAGTAGTGGAAACCG GAG SEQ ID NO: 49 |
| GAPDH | GAAGATGGTGATGGG ATTTC SEQ ID NO: 50 | GAAGGTGAAGGTCGGA GTC SEQ ID NO: 51 |
| GATA4 | CGACTTCTCAGAAGG CAGAGAGTG SEQ ID NO: 52 | CTTCATGTAGAGGCCG CAGGCATT SEQ ID NO: 53 |
| HNF1B | CCAAGCCGGTCTTCC ATACTC SEQ ID NO: 54 | TGGGAGGTGTGTCATA GTCGT SEQ ID NO: 55 |
| HNF4A | CTTCCTTCTTCATGCC AG SEQ ID NO: 56 | ACACGTCCCCATCTGA AG SEQ ID NO: 57 |
| endoNANOG | TTTGGAAGCTGCTGG GGAAG SEQ ID NO: 58 | GATGGGAGGAGGGGAG AGGA SEQ ID NO: 59 |
| endoOCT4 | AGTTTGTGCCAGGGT TTTTG SEQ ID NO: 60 | ACTTCACCTTCCCTCCA ACC SEQ ID NO: 61 |
| PAX6 | GTCCATCTTTGCTTCT GGAAA SEQ ID NO: 62 | TAGCCAGGTTGCGAAG AACT SEQ ID NO: 63 |
| SERPINA1 | TCGCTACAGCCTTTGC AATG SEQ ID NO: 64 | TTGAGGGTACGGAGGA GTTCC SEQ ID NO: 65 |
| SOX17 | GGCGCAGCAGAATCC AGA SEQ ID NO: 66 | CCACGACTTGCCCAGC AT SEQ ID NO: 67 |
| TAT | GCCTCCCAGCAACGT GCTTTG SEQ ID NO: 68 | CTCCTGGATCCGGCTGC ACG SEQ ID NO: 69 |
| TF | TCCGGGTGCGGCGCT GAG SEQ ID NO: 70 | GGCGAGCCTCATCCTC CGGG SEQ ID NO: 71 |

Luminescence-based P450-Glo Assays (Promega) were used to measure the activities of the CYP3A family (Luciferin-PFBE, V8901), CYP3A4 (Luciferin-IPA, V9001), and CYP2C19 (Luciferin-H EGE, V8881) following the manufacturer's instructions. Results are shown as Luminescent Counting Units (LCU)/minute normalized to a million viable cells. Metabolically well-characterized aHeps (Life Technologies HMCPMS Lot#Hu8138) were used as positive controls.

PAS Staining

PAS (Sigma-Aldrich) staining was performed following the manufacturer's instructions.

Lipid Staining

BODIPY 493/503 (Life Technologies) solution (1 mg/mL) was added to the medium (2 μL per well of a 12-well plate); 1 hour later, the cells were washed with medium, and imaged using fluorescence microscopy. For ORO staining, cells were fixed in 10% formalin, incubated with ORO staining solution (Sigma-Aldrich) for 1 hour at room temperature, washed with water, and imaged using light microscopy.

LDL Uptake Assay

DiI-ac-LDL (Invitrogen) was added to the medium (5 μL per well of a 12-well plate); 2 hours later, the cells were washed with medium, and imaged using fluorescence microscopy.

Urea Production

Cell culture supernatant was collected and analyzed using the QuantiChrom Urea Assay Kit (BioAssay Systems) following the manufacturer's instructions.

ALB ELISA of Cell Culture Supernatants

The amount of ALB in cell culture supernatants was determined using a human-specific albumin ELISA kit (Assaypro) following the manufacturer's instructions. Cells were cultured in HMM for 24 hours, and the supernatant was collected for analysis. Control aHeps (Life Technologies HMCPMS Lot #Hu8138) were analyzed 24 hours after plating.

Mice and Transplantation

Procedures involving mice were approved by the Institutional Animal Care Committee at the University of California San Francisco. Immune-deficient, fumarylacetoacetate hydrolase (Fah)-deficient mice lacking B, T, and natural killer cells due to disruption of Rag2 and Il2rg-so-called FRG mice-were used as recipients (Azuma et al., Nat Biotechnol 25, 903-910, (2007)). Mice were maintained on NTBC in the drinking water at 16 mg/L 1 day before transplantation, mice were taken off NTBC. An adenovirus expressing urokinase plasminogen activator (Ad-uPA) was used for liver preconditioning (Lieber et al., Proc Natl Acad Sci USA 92, 6210-6214, (1995)). Ad-uPA was delivered by retroorbital injection 24 hours before transplantation at a dose of $5 \times 10^7$ PFU/g body weight. Transplantation was performed by intrasplenic injection through a left flank incision under isoflurane anesthesia and buprenorphine analgesia. After transplantation, mice received NTBC in the drinking water in cycles consisting of 7-10 days off NTBC and 2-3 days on NTBC at 4 mg/L. For surgical prophylaxis, 5 mg Naxcel (Pfizer) were given by intraperitoneal injection immediately before transplantation, and daily for 7 days. Due to the immune deficiency of the mice, all mice received prophylactic antibiotic treatment with Cipro (Hospira) at 0.25 mg/mL in the drinking water for 7 days, then trimethoprim/sulfamethoxazole (TMP/SMX, Sigma-Aldrich) in the drinking water at 0.2 g/L TMP and 1 g/L SMX continuously. aHeps for transplantation were purchased from Yecuris, shipped overnight in suspension, and transplanted into recipient mice immediately after arrival.

iMPC-Hep Transplantation and Analysis iMPC-Heps were injected intrasplenically into FRG mice preconditioned by withdrawal of the drug 2-(2-nitro-4-fluoromethylbenzyl)-1,3-cyclohexanedione (NTBC) and retroorbital injection of $5 \times 10^7$ PFU/g body weight adenovirus expressing urokinase plasminogen activator. Mice underwent repeated cycles of NTBC off for 10 days and on for 2-3 days. For analysis of human CYP2D6 activity, the drug DB was administered by gavage and plasma levels of DB and its metabolite 4-OH-DB were measured by LC/MS/MS.

HSA ELISA

Blood (3 μL) was drawn by tail clipping and immediately diluted 1:100 in ELISA sample diluent (Bethyl). HSA concentration was determined by ELISA using an antibody specific for human albumin (Bethyl).

Tissue Immunostaining

Liver tissue harvested from recipient mice was frozen immediately in optimum cutting temperature (OCT) compound (Tissue-Tek, Sakura Finetek), or fixed in 4% paraformaldehyde (Sigma-Aldrich) or 10% formalin (Sigma-Aldrich) at 4° C. overnight. Tissues for frozen sections were cryoprotected in 30% sucrose (Sigma-Aldrich) before embedding and freezing in OCT. Paraffin-embedded tissues were preserved in 70% ethanol prior to tissue processing and paraffin embedding. Frozen tissues were cut using a Leica 3050S Cryostat into 5 μm sections, air dried, and stored at −20° C. prior to staining. Tissue sections were stained with rabbit anti-FAH antibody (Espejel et al., *J Clin Invest* 120, 3120-3126, (2010); gift from Robert Tanguay, Université Laval) diluted 1:15,000, mouse anti-Ki67 antibody (BD Pharmingen, Cat #550609) diluted 1:25, FITC-conjugated goat anti-mouse albumin diluted 1:100 (Bethyl, Cat # A90-234F), goat anti-human albumin (Bethyl, Cat #A80-229A) diluted 1:100, rabbit anti-CYP2D6 diluted 1:200 (Sigma-Aldrich, Cat #AV41675), rabbit anti-CYP3A4 diluted 1:50 (Abcam, Cat #ab135813), or FITC-conjugated mouse anti-human 12-microglobulin (BioLegend, Cat #316304) diluted 1:200, Antigen retrieval using Citra solution (Biogenex) was done before immunostaining for Ki67 and mouse albumin. For fluorescence microscopy, primary antibodies were detected with donkey anti-rabbit conjugated with Cy3 (Jackson immunoResearch), donkey anti-goat conjugated with Alexa Fluor 488 (Jackson ImmunoResearch), donkey anti-goat conjugated with Alexa Fluor 594 (Jackson ImmunoResearch), donkey anti-rabbit conjugated with Alexa Fluor 488 (Invitrogen), or the M.O.M. Fluorescein kit (Vector). Nuclear DNA was stained with 2 μg/mL DAPI (Invitrogen).

Quantification of Liver Repopulation

Overall liver repopulation with transplanted iMPC-Heps was determined by measuring the area of recipient mouse liver sections composed of iMPC-Heps by ALB and FAH immunostaining relative to the total area of liver tissue. Sections were taken from 6 separate pieces of liver tissue from different parts of the recipient's liver. Areas were calculated using ImageJ software (NIH). The number of iMPC-Heps per nodule was estimated using a previously described method (Espejel et al., *J Clin Invest* 120, 3120-3126, (2010); Wang et al., *Am J Pathol* 161, 565-574, (2002)). Briefly, the number of iMPC-Heps present in the 2-dimensional section showing the widest diameter of a repopulating nodule was multiplied by a previously determined correction factor to estimate the total number of hepatocytes comprising the 3-dimensional nodule.

LCM and Microarray Analysis

Repopulating nodules were isolated using a PALM MicroBeam IV system (Zeiss). PALM RoboSoftware 4.3 SPI was used to create LCM matrices based on ALB immunostaining of cryosections flanking a 7 μm unfixed cryosection from which nodules were isolated. Multiple nodules from a mouse were pooled to generate a sample. RNA was extracted and purified using the Arcturus Pico Pure RNA Isolation Kit (AB Biosystems). RNA quality was analyzed using chip-based capillary electrophoresis (Bioanalyzer, Agilent), and quantity and purity were determined with a NanoDrop spectrometer. The NuGEN Pico V2 kit was used for amplification, fragmentation, and biotin labeling. Labeled cDNA was hybridized to GeneChip Human Gene 1.0 ST Arrays (Affymetrix). Signal intensity fluorescent images produced during Affymetrix GeneChip hybridizations were read using the Affymetrix Model 3000 Scanner and converted into GeneChip probe results files (CEL) using Command and Expression Console software (Affymetrix). Arrays were normalized for array-specific effects using Affymetrix Robust Multi-Array (RMA) normalization. Normalized array values were reported on a log 2 scale. For statistical analyses, background noise was eliminated by removing probesets for which no experimental group had an average log 2 intensity: 3. Linear models were fitted for each gene using Bioconductor limma in R. Moderated t statistics, fold change, and the associated P values were calculated for each gene. Heatmaps were created using heatmap.2 in R v2.11.0. Gene sets of hepatocyte function-related GO terms were obtained from MSigDB (broadinstitute.org/gsea/msigdb).

In Vivo CYP2D6 Activity Analysis

Plasma samples (40 μL) were obtained by retroorbital blood draw at 0, 1 and 2 hours after administering 2 mg/kg body weight debrisoquine (DB; Enzo Life Sciences) in water by gavage. A standard curve was created by serial dilution of a solution with equal amounts of DB and 4-hydroxy-DB (Santa Cruz Biotechnology), using a 1:1 acetonitrile:$H_2O$ solvent mixture. Aliquots of standard solutions not exceeding 5 μL in size were added to 100 μL of Swiss Webster $K_2$EDTA mouse plasma (Bioreclamation) to create plasma standards with concentrations from 0.01 μM to 50 μM. All plasma samples were precipitated with 4 volumes of cold acetonitrile, vortexed for 1 minute, and after standing for 30 minutes at −20° C., centrifuged for 5 minutes at 13,000×g. The supernatants separated into upper and lower phases; the smaller lower phases were used in the analyses. DB and 4-OH-DB were measured by LC/MS/MS with an API4000 MS/MS mass spectrometer (AB Sciex) with ESI in the positive ion mode. They were detected using the transitions 176.1→134.1 and 192.1→132.1 m/z. Instrumental settings were 46 and 41 v for DP, and 25 and 27 v for CE, respectively. Settings in common for both analytes were CXP=8 v, EP=10 v, CAD=12 v, IS=5500 v, temp.=600° C., CUR=35 and GS1=GS2=50. The LC method employed a 50×4.6 Inn C18, 5 μm, 100 Å, Kinetex column (Phenomenex) and a binary mobile phase with A=15% methanol:$H_2O$ (with 160 mg/L $NH_4CH_3CO_2$, 0.1% formic acid, and 0.1% acetonitrile) and B=100% methanol (with the same additions). Flow rate was 0.5 mL/minute. The gradient used was as follows: 0-1 minute, 0% B; 1-4 minutes, linear ramp to 100% B; 4-5 minutes, 100% B; 5 to 5.5 minutes, linear ramp to 0% B; 5.5 to 8.0 minutes, 0% B. Injection size was 3 μL, and retentions were 2.94 minutes for 4-OH-DB and 3.85 minutes for DB.

Survival Studies

To model acute liver failure, FRG mice were taken off NTBC and injected with $5×10^7$ PFU/g body weight Ad-uPA 1 day before transplantation. Mice were kept off NTBC and survival was recorded daily. To model chronic liver failure, mice were also taken off NTBC and injected with $5×10^7$ PFU/g body weight Ad-uPA 1 day before transplantation, but NTBC was reinstated at a dose of 4 mg/L 7 days after transplantation. From there on, mice were subjected to repeated cycles of NTBC off for 10 days and NTBC on for 3 days. Survival was recorded twice a week.

Example 2: Generating Endodermal Progenitor Cells (EPCs)

This Example describes generation of hepatocytes (iMPC-Heps) that were not compromised by the growth arrest inherent to current iPSC/ESC-Hepatocytes.

As described in Example 1, newborn fibroblasts ($1\times10^4$) that retrovirally express OCT4, SOX2, and KLF4 (Takahashi et al., *Cell* 131, 861-872, (2007)) were replated for induction of endoderm reprogramming in medium containing epidermal growth factor (EGF), basic fibroblast growth factor (bFGF), and CHIR99021 (CHIR; a small molecule that activates WNT signaling by way of inhibiting glycogen synthase kinase 3β). FIG. 1A shows a schematic diagram of the timing and factors that were used.

Figure 1B:
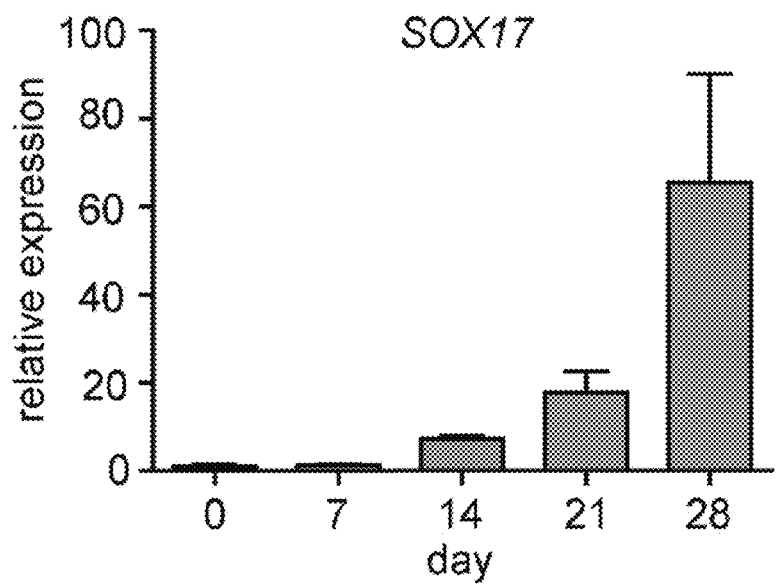
Figure 1C:
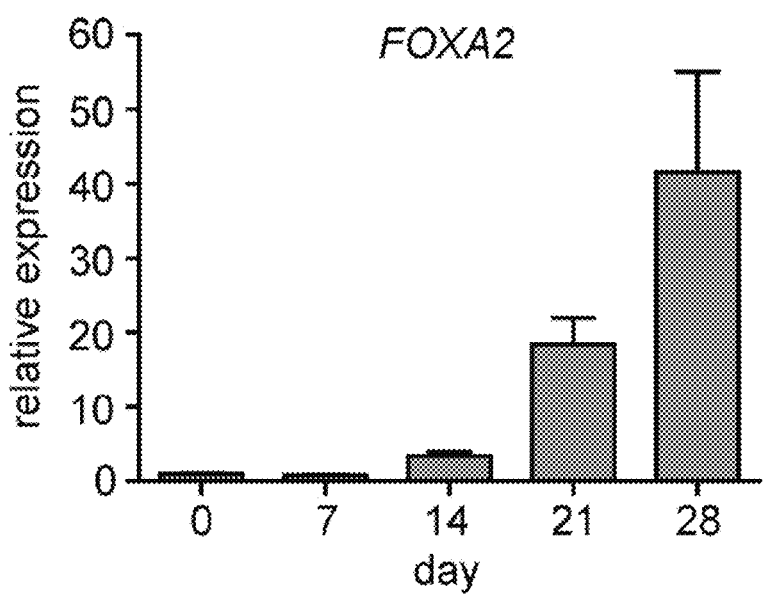
Figure 1D:
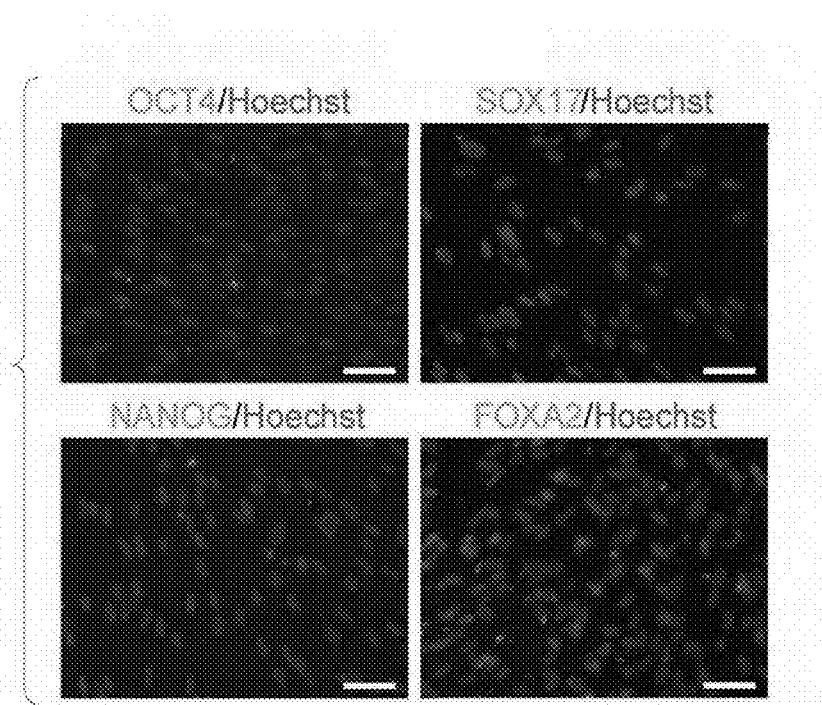
Figure 1E:
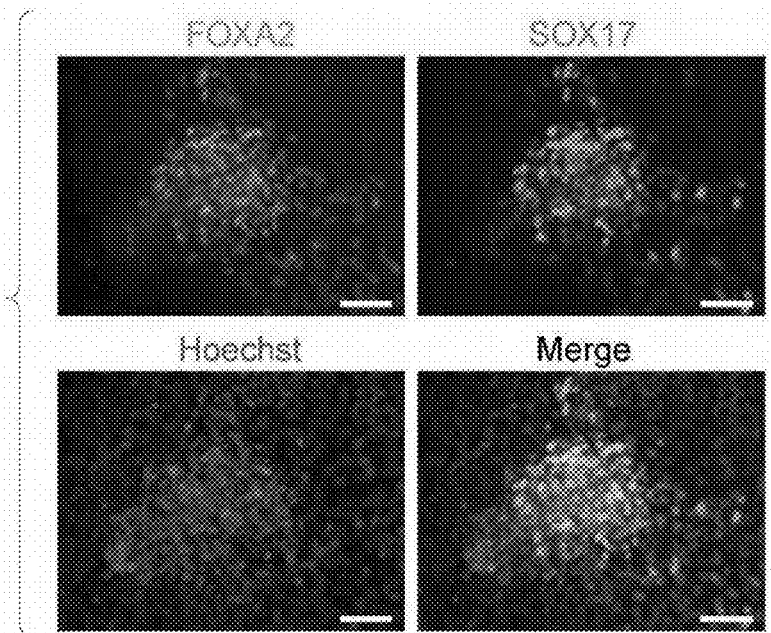
Figure 2A:
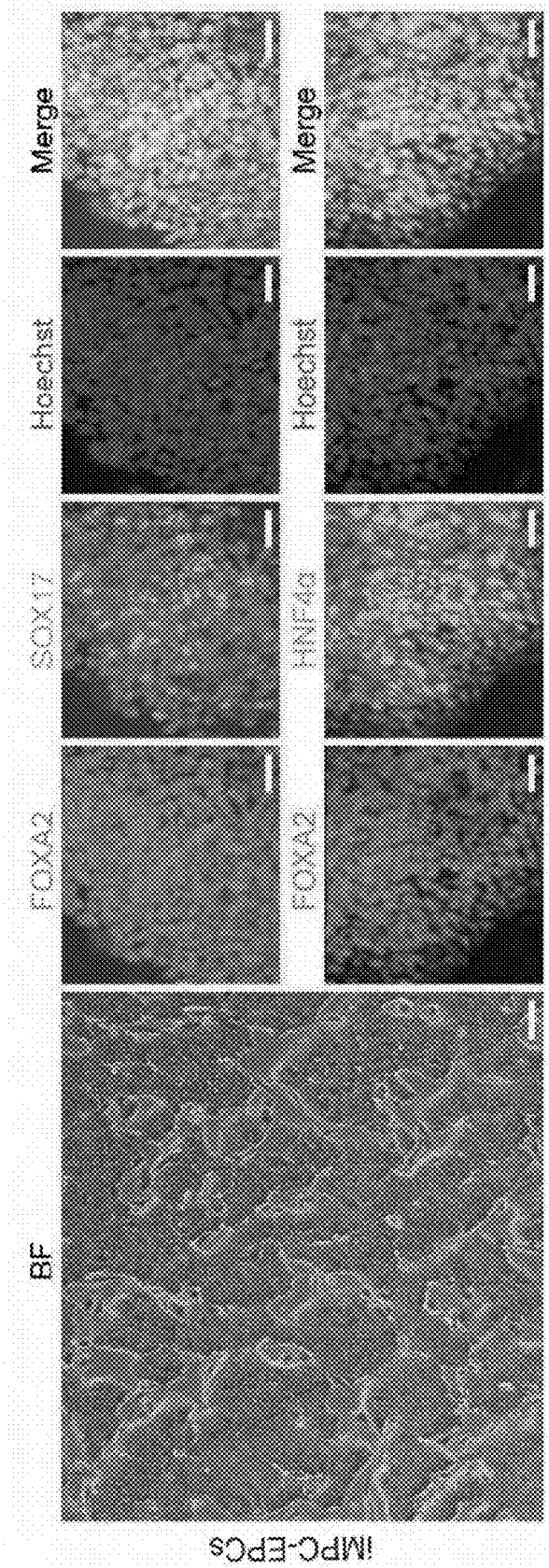
Figure 2B:
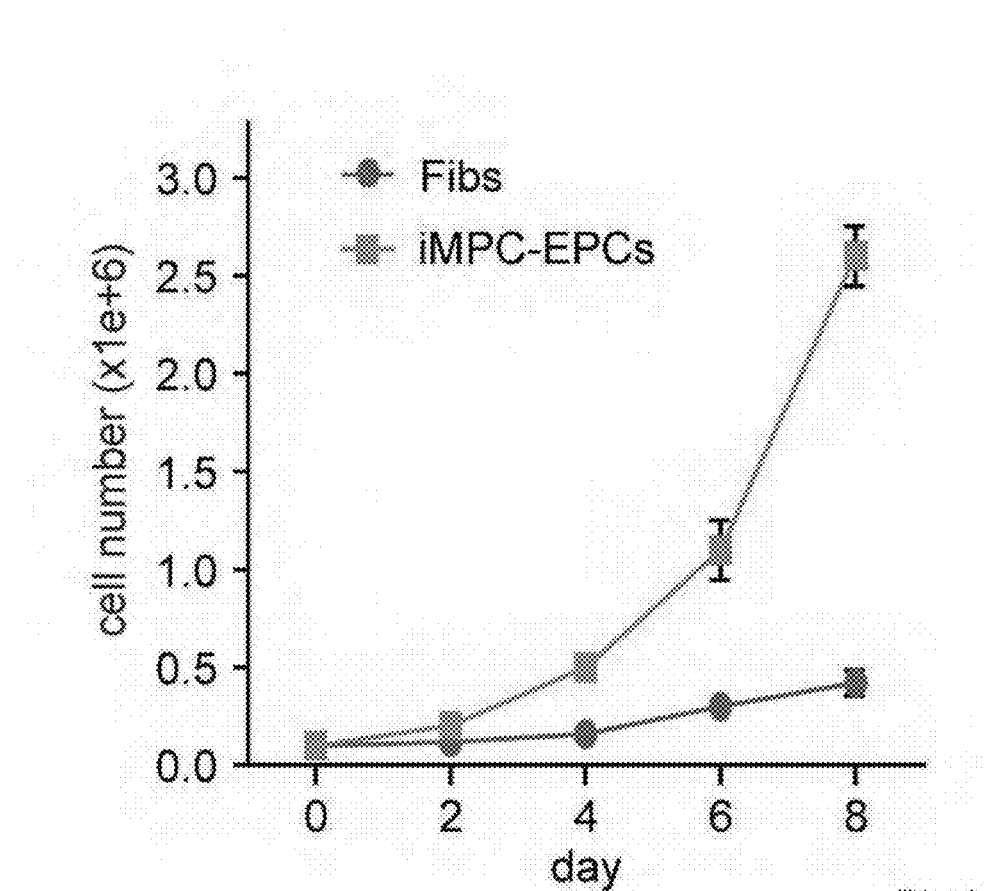
Figure 2D:
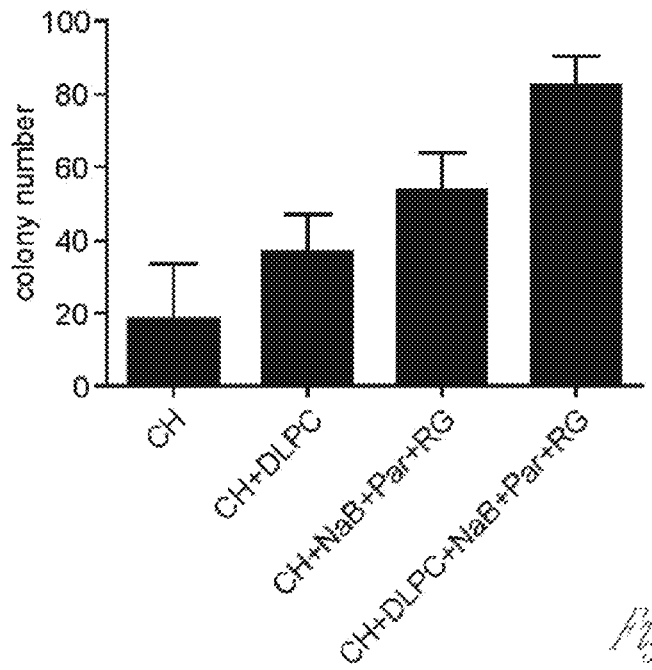

Next, EGF and bFGF were replaced with Activin A to induce Nodal signaling and promote endoderm fate (see FIG. 1A). When these cultures were analyzed by quantitative reverse-transcription PCR (qRT-PCR) expression of the endoderm-specific genes SOX17 and FOXA2 was observed as early as 14 days after starting the reprogramming process (FIG. 1B). However, only 20 colonies were positive for SOX17 and FOXA2 as detected by immunostainings, even when the reprogramming process was extended to 28 days (FIG. 1C-E and FIG. 2). To improve the efficiency of endoderm differentiation, the cells were exposed to several small molecules. Dilauroyl phosphatidylcholine (DLPC), which is an agonist of the nuclear receptor liver receptor homolog 1, caused a 2-fold increase in the number of FOXA2-positive colonies (FIG. 2D). Adding the epigenetic modifiers sodium butyrate (NaB; HDAC inhibitor), Parnate (Par; LSD1 inhibitor), and RG108 (RG; DNMT inhibitor) further increased the number of FOXA2-positive colonies that could be generated from $1\times10^4$ fibroblasts to over 80 (FIG. 2D).

Example 3: Reprogrammed EPCs do not Pass Through Pluripotency

Figure 3A:
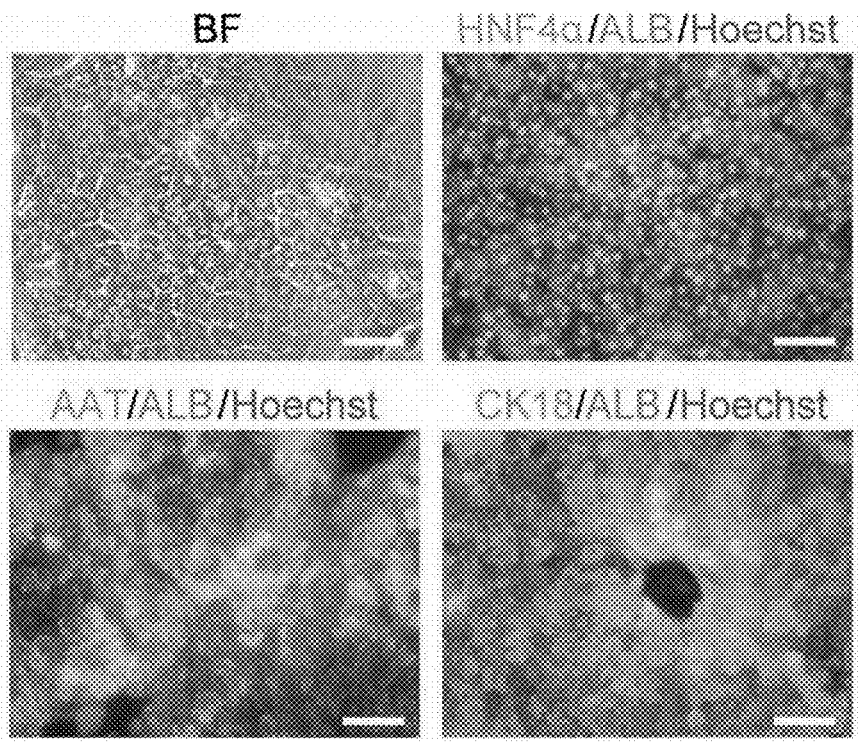
Figure 3B:
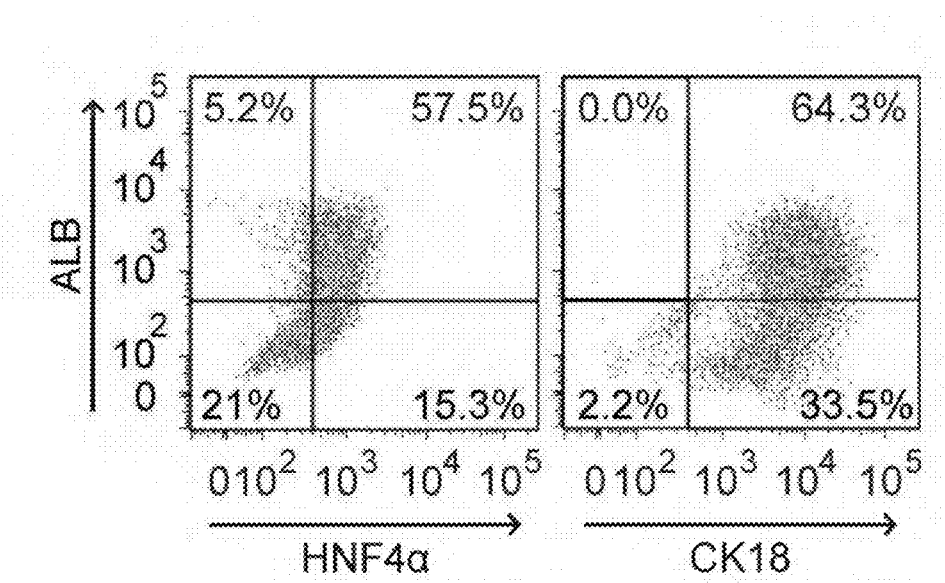
Figure 3C:
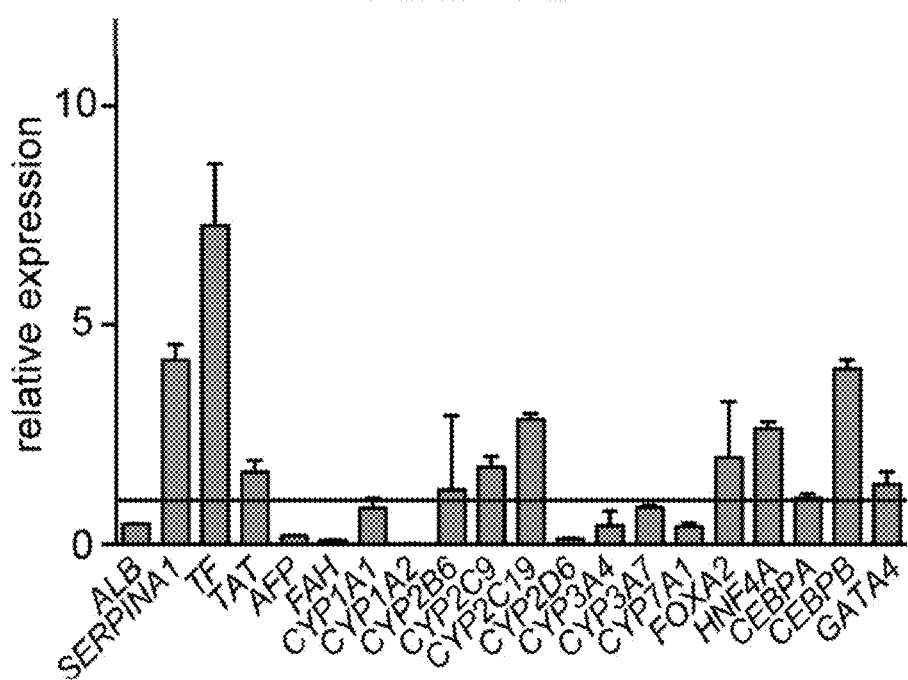
Figure 3D:
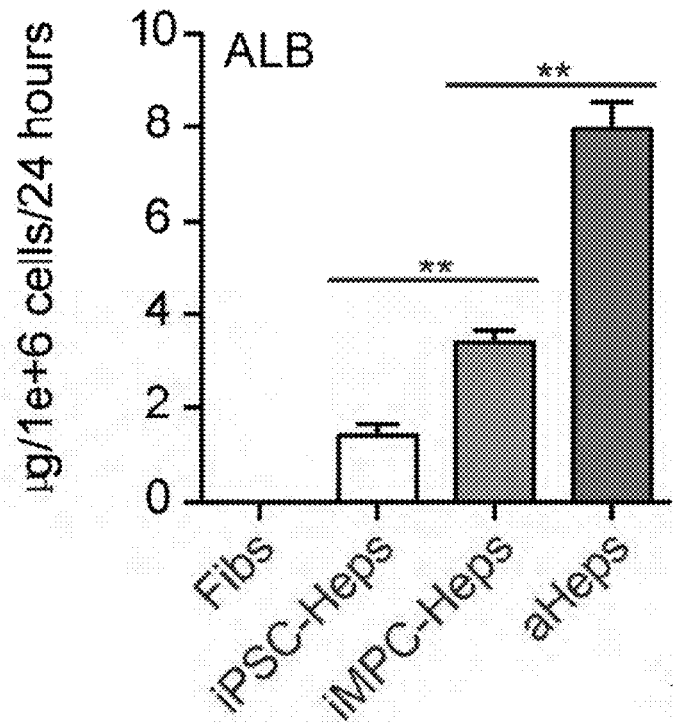
Figure 3E:
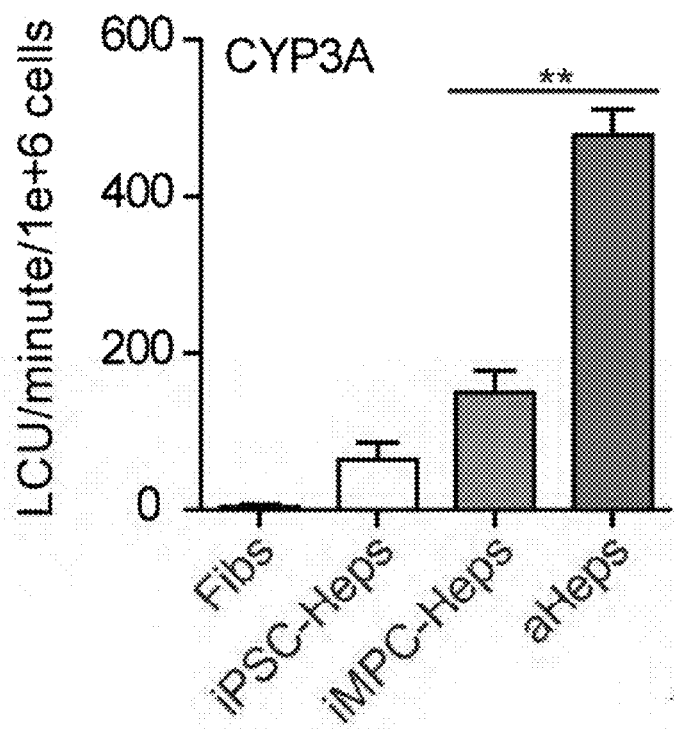
Figure 3H:
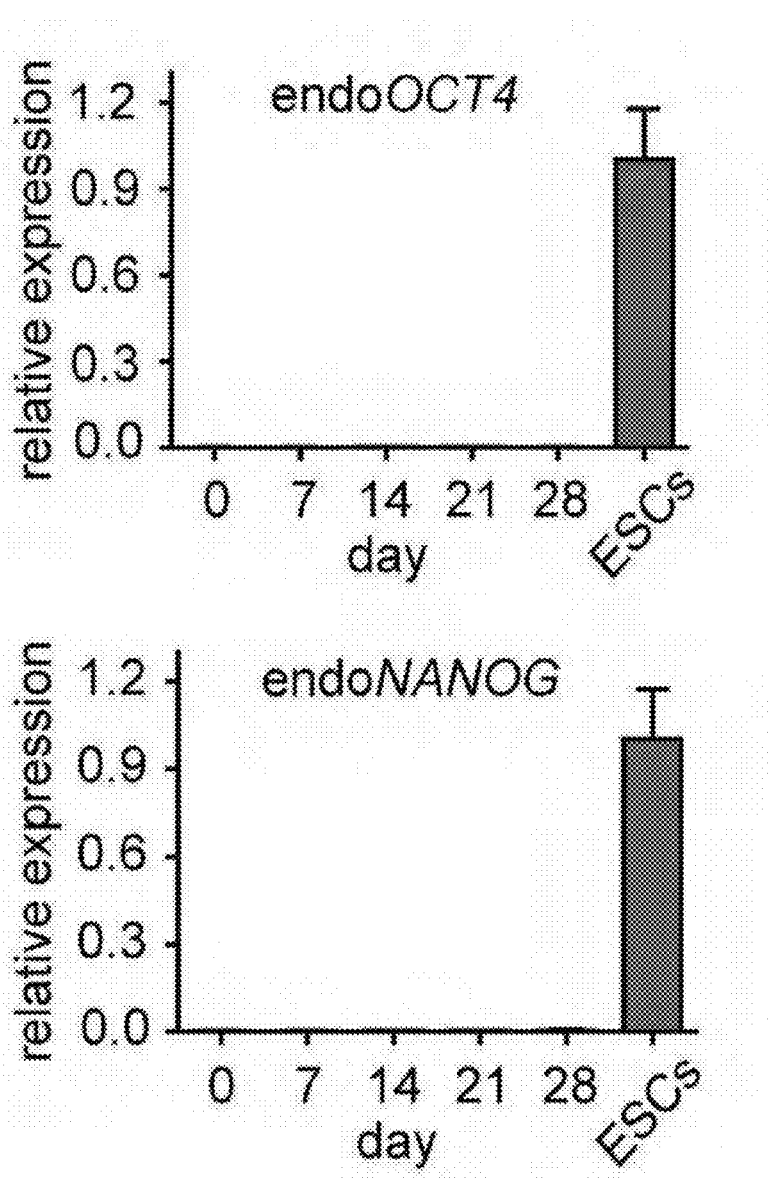
Figure 9I:
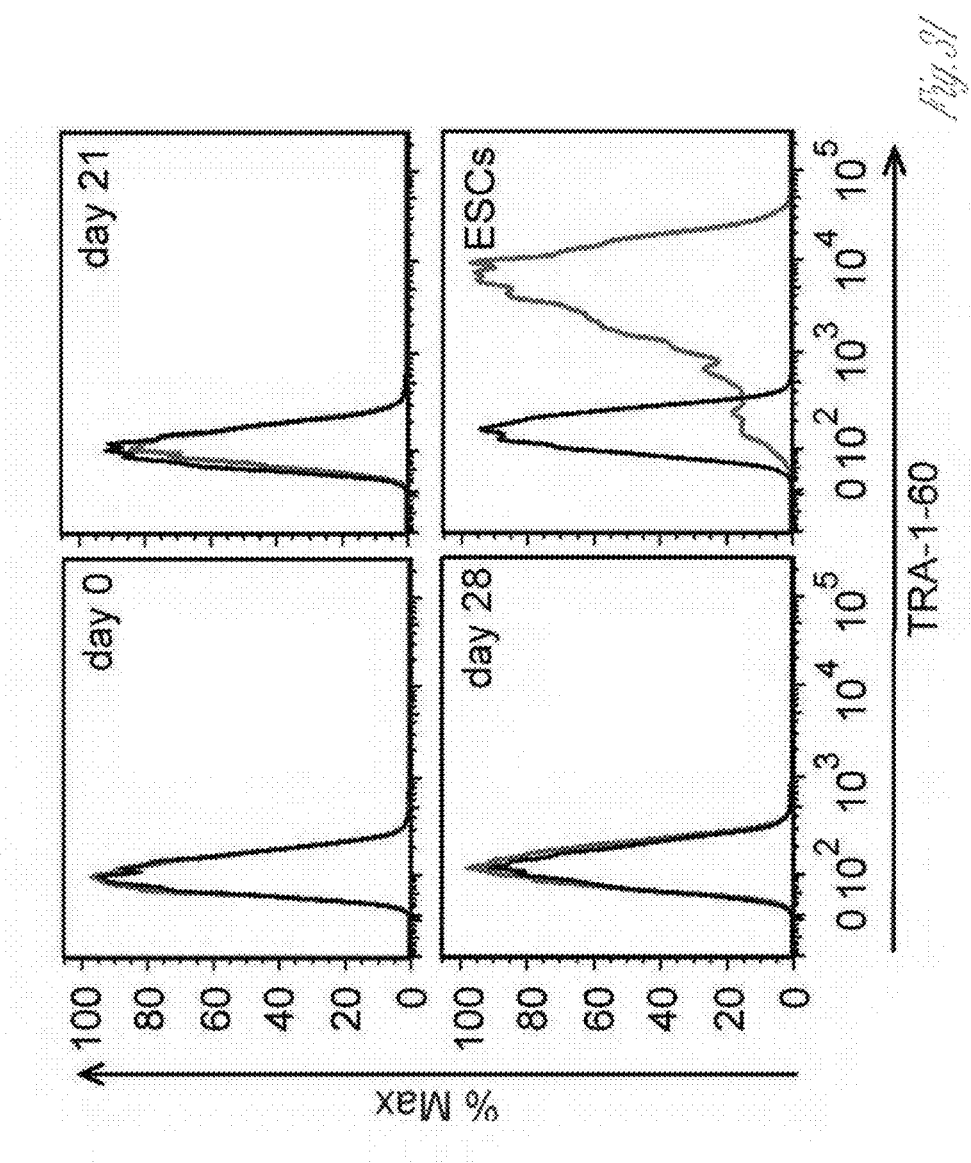
FIG. 9A-9B show that iMPC-EPCs have hepatic and pancreatic differentiation potential.
Figure 3I:
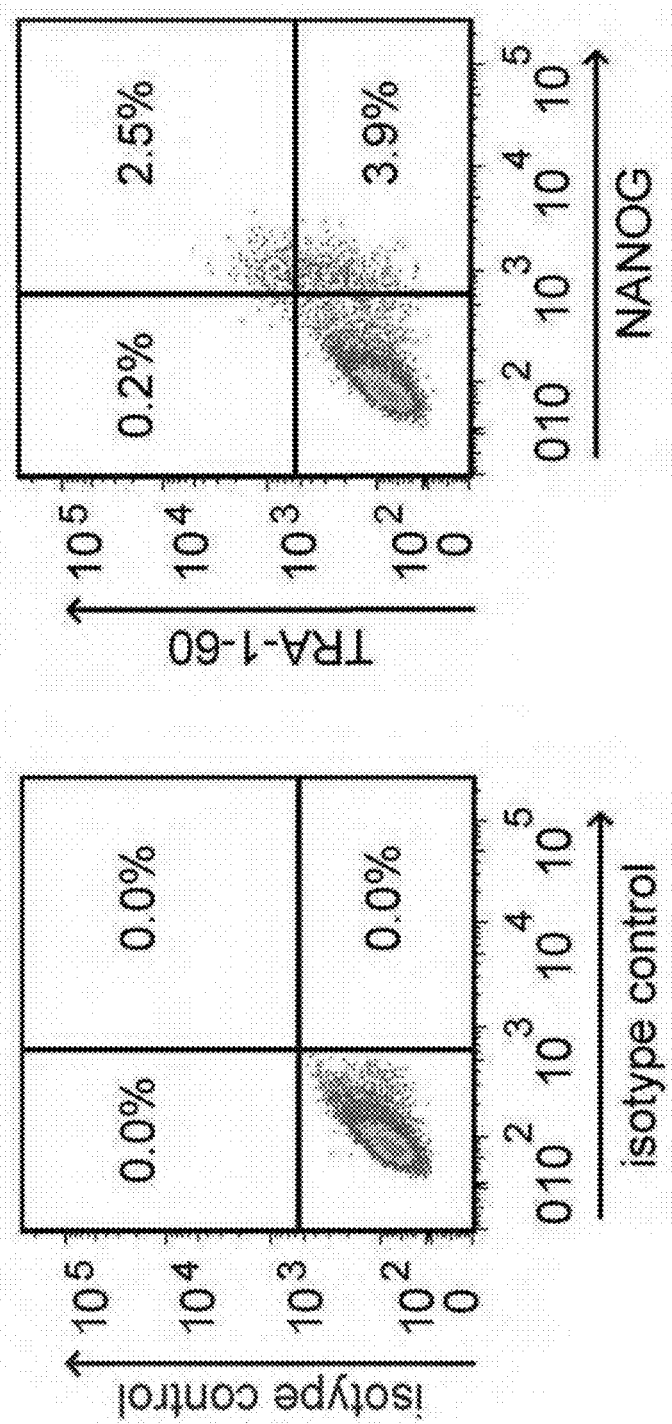
Figure 4A:
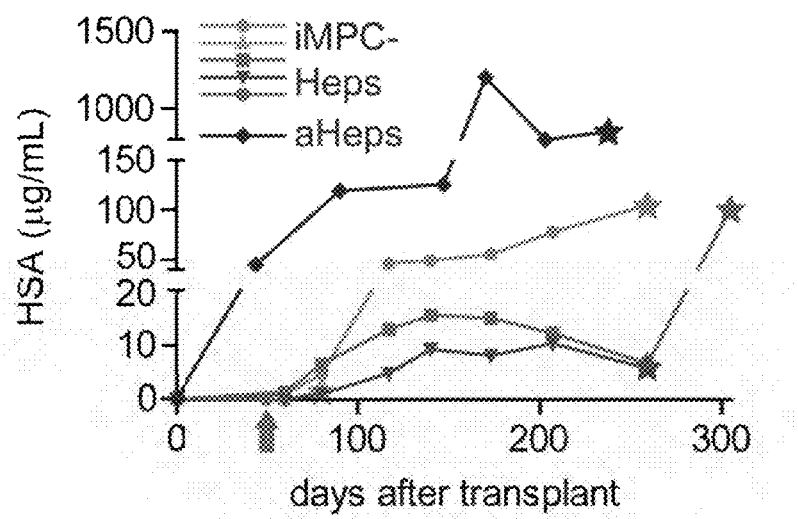
Figure 4B:
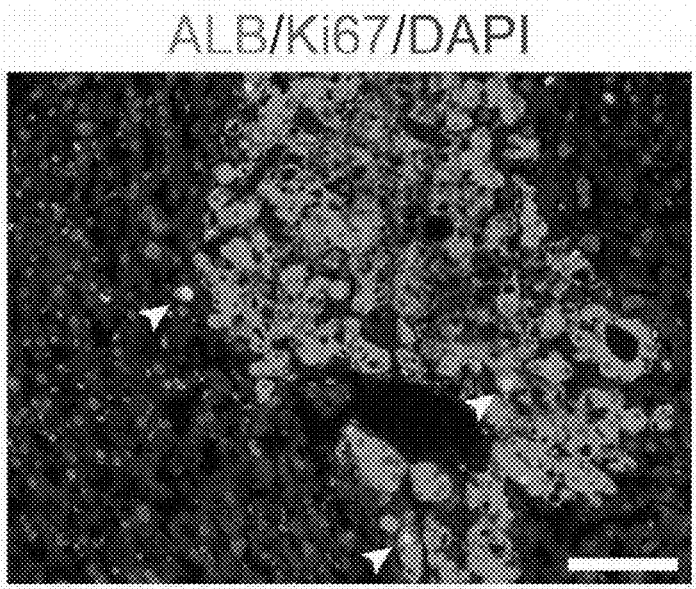
Figure 4C:
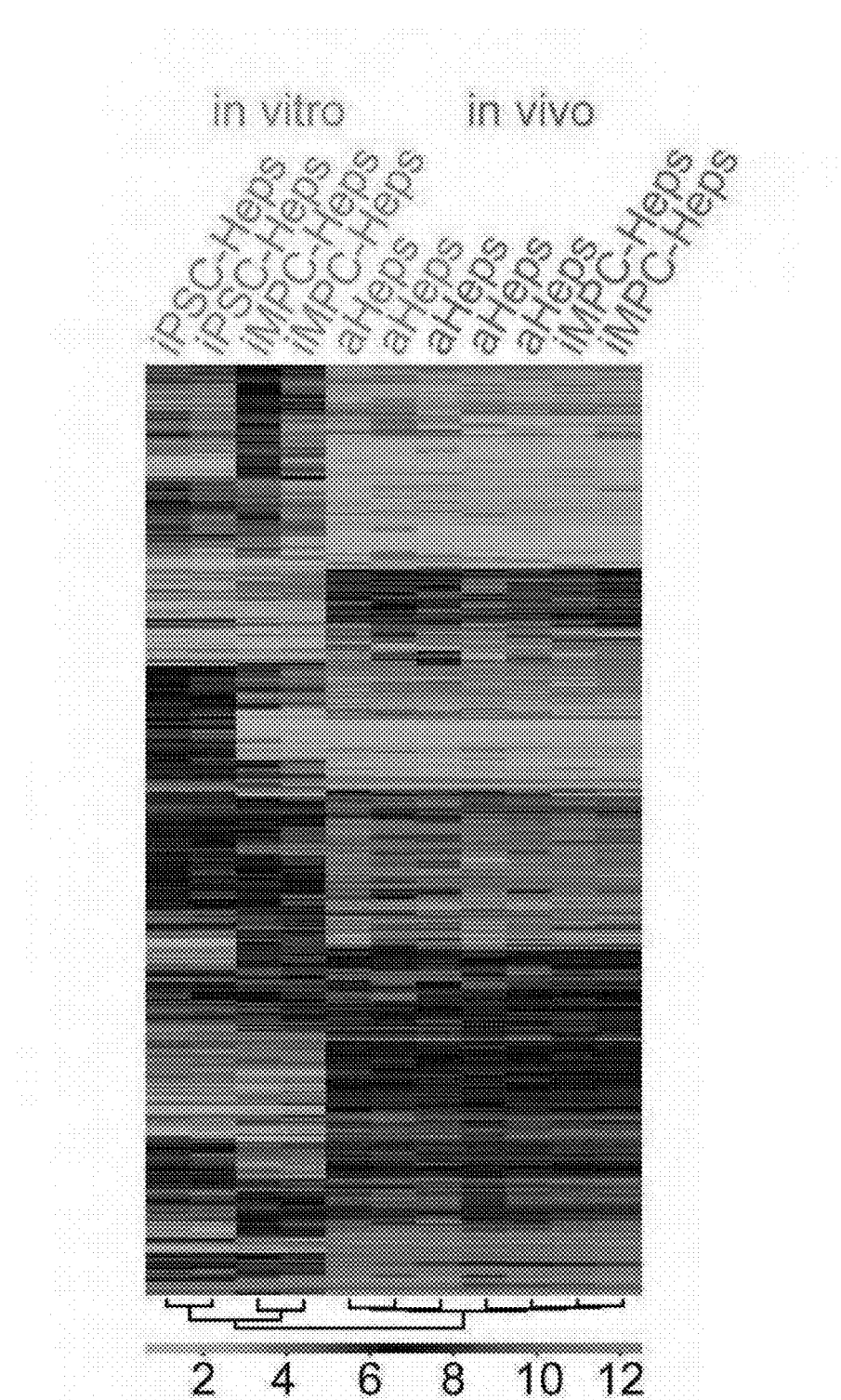
Figure 4D:
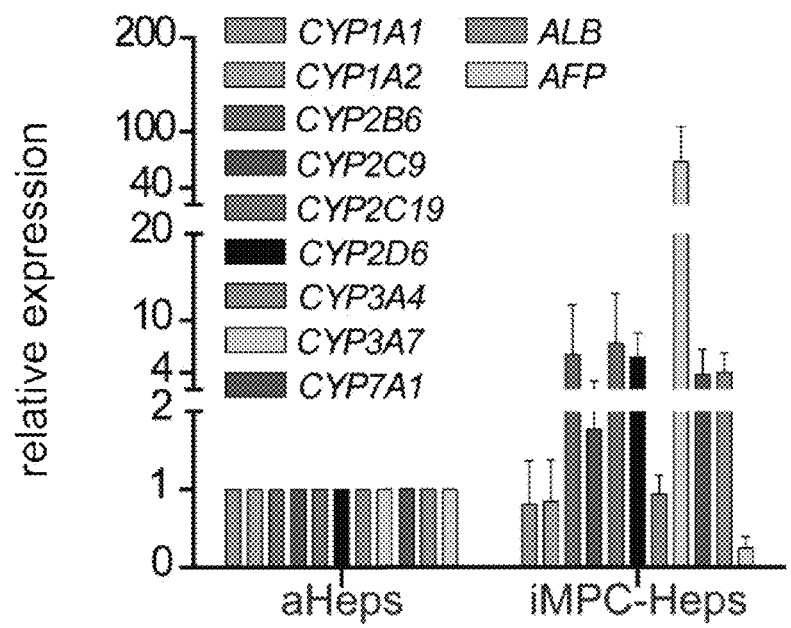
Figure 4E:
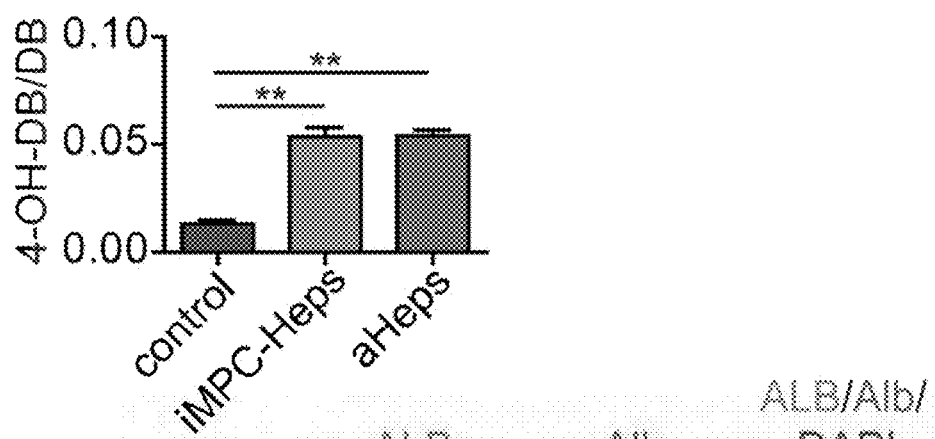
Figure 4F:
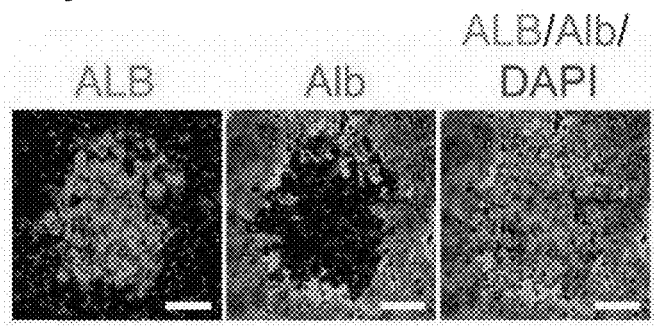
Figures 4G, 4H:
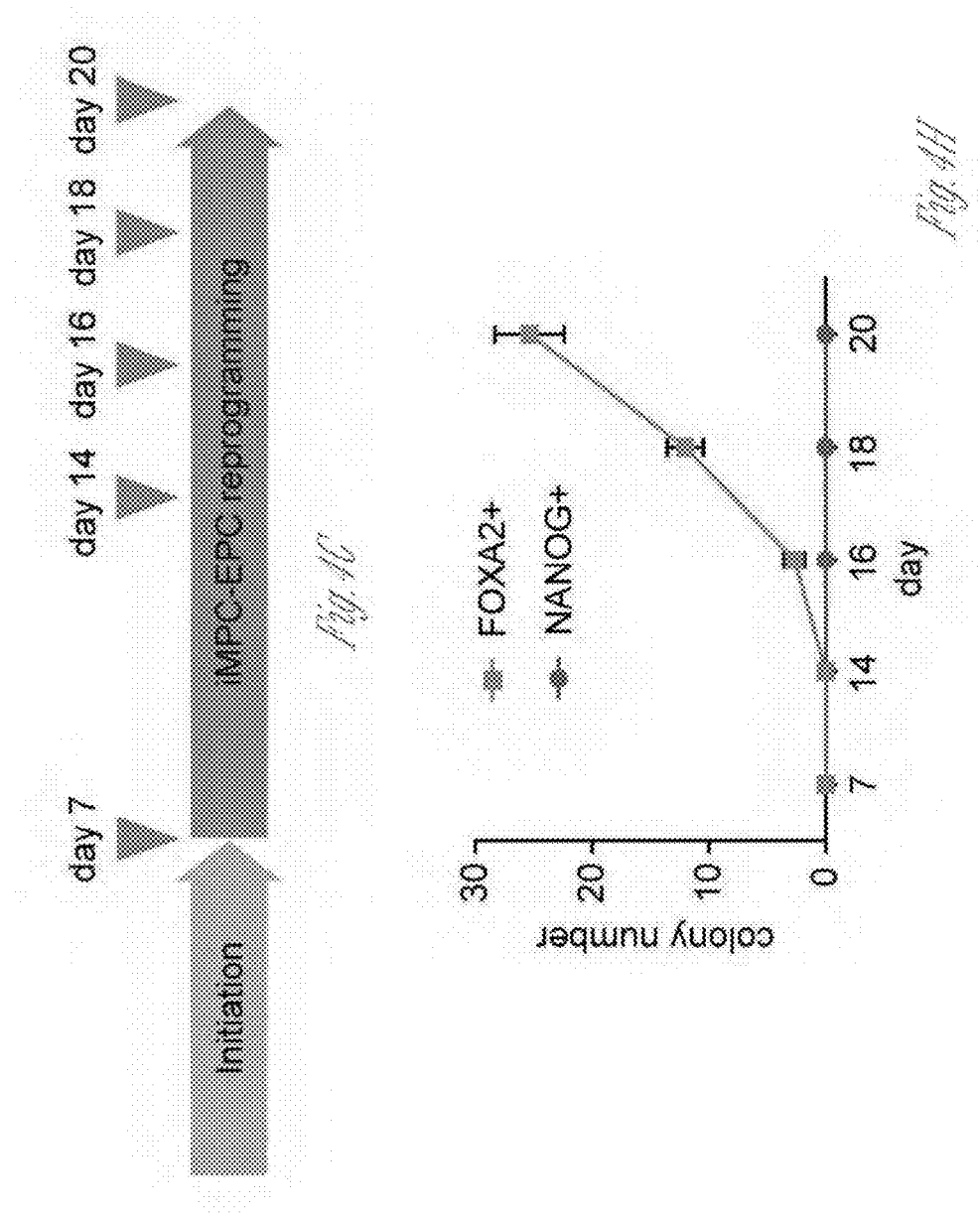
Figure 17:
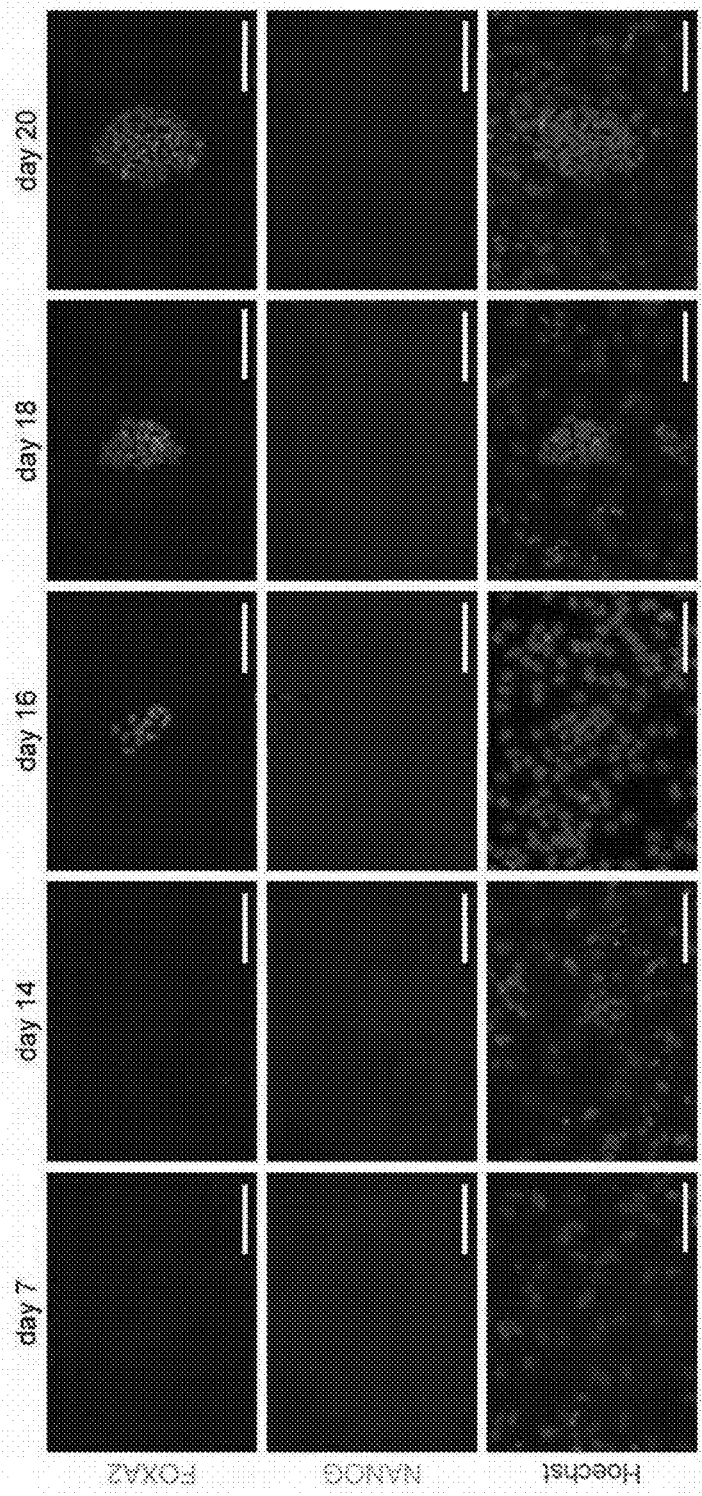
FIG. 17 illustrates in vivo maturation of iMPC-Heps by AFP immunostaining. The iMPC-Heps were co-immunostained for ALB and AFP. As shown, the immature hepatocyte-specific marker AFP was not expressed in iMPC-Hep and adult Hep nodules. Human fetal liver was used as a positive control. Scale bars=100 µm.
Figure 4J:
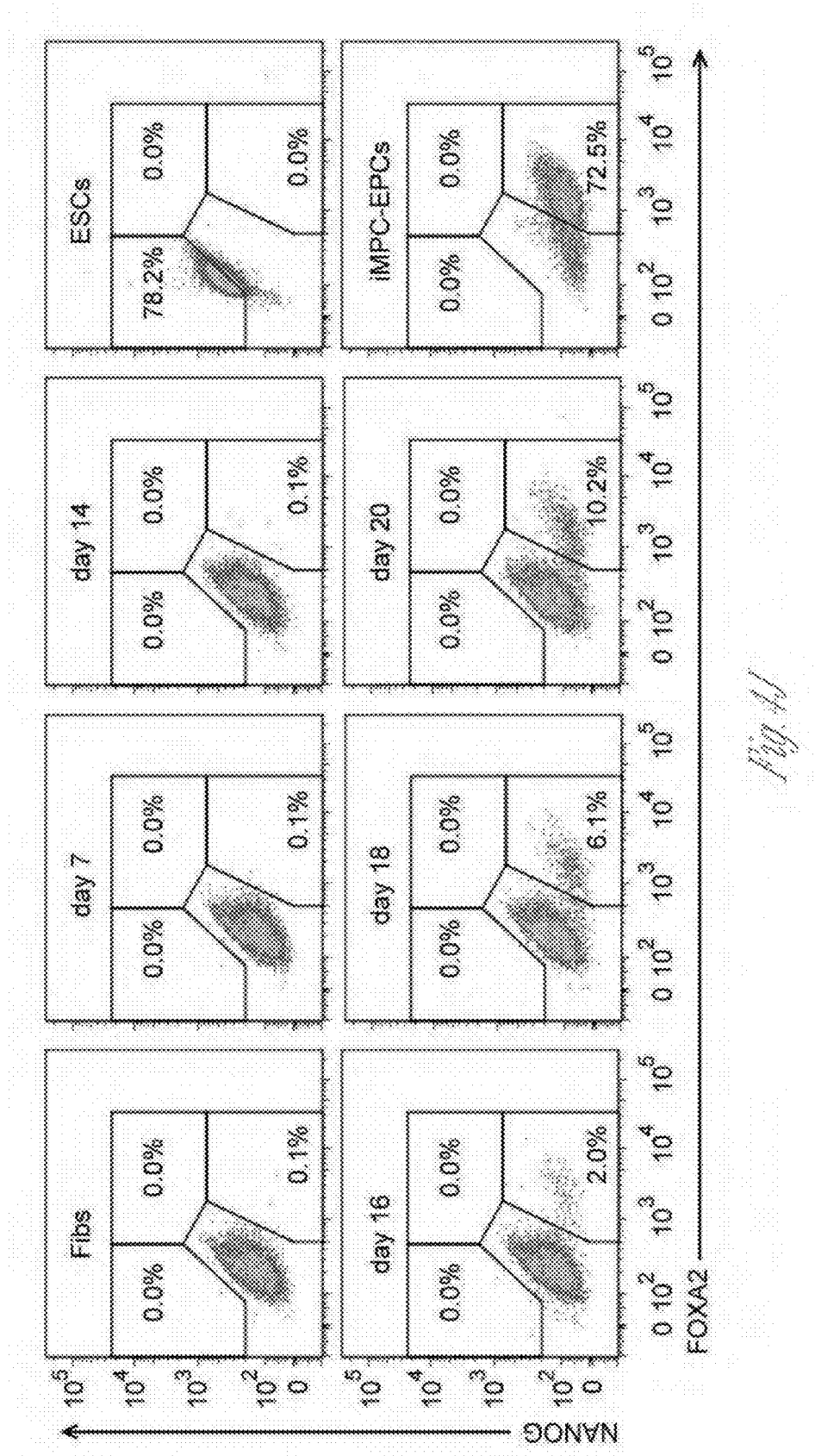
Figure 54:
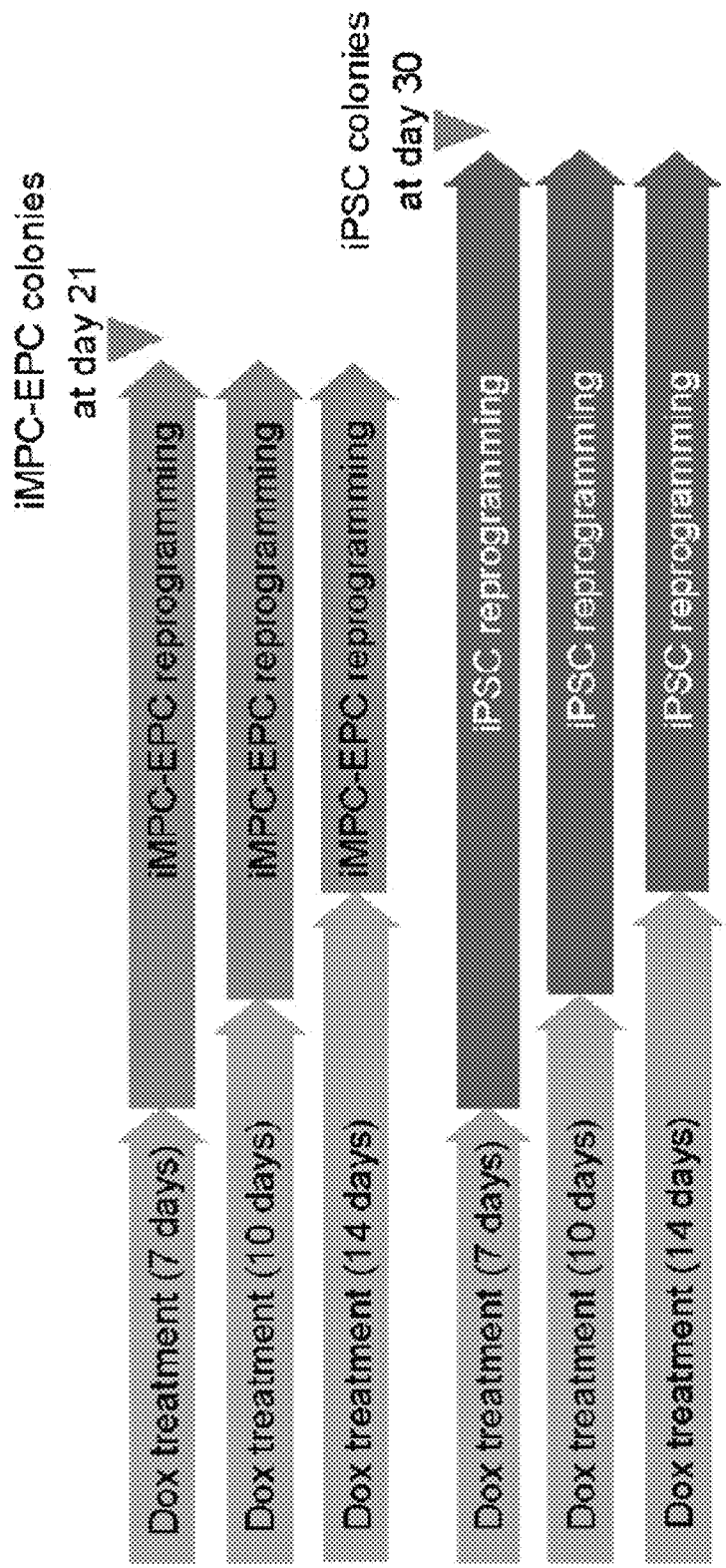

Avoiding a pluripotent state decreases the tumor risk of transplanted cells. As shown in FIG. 3H, expression of the pluripotency-specific genes OCT4 and NANOG was not detectable even at the earliest stages of the reprogramming process. These results were confirmed by flow cytometry, which showed that only a few cells expressed the pluripotency marker TRA-1-60 at the end of the reprogramming process (FIG. 3I-3J). In addition, immunostaining and flow cytometry for FOXA2 or NANOG to monitor cultures undergoing reprogramming for the emergence of endoderm cells, referred to as iMPC-EPCs (FIG. 4G). Colonies of FOXA2-positive cells were observed as early as 16 days after starting the reprogramming process, whereas NANOG-positive cells were absent at all stages of the reprogramming process (FIG. 4H-4J).

Figure 5B:
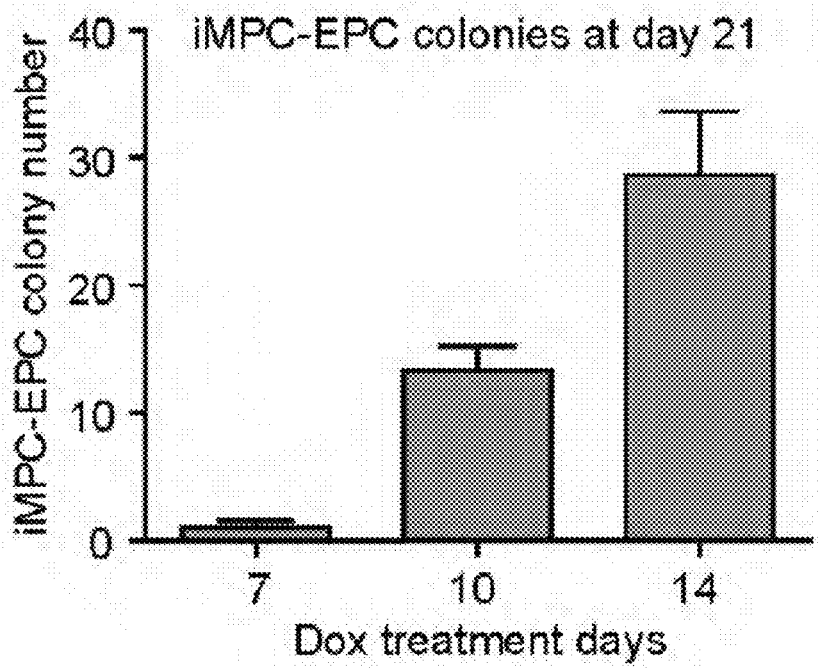
FIG. 5B graphically illustrates the number of iMPC-EPC colonies forming from newborn fibroblasts (Fibs) over time where the newborn fibroblasts were cultured under iMPC-EPC reprogramming conditions. iMPC-EPC colonies were identified by FOXA2 expression (immunostaining).
Figure 5C:
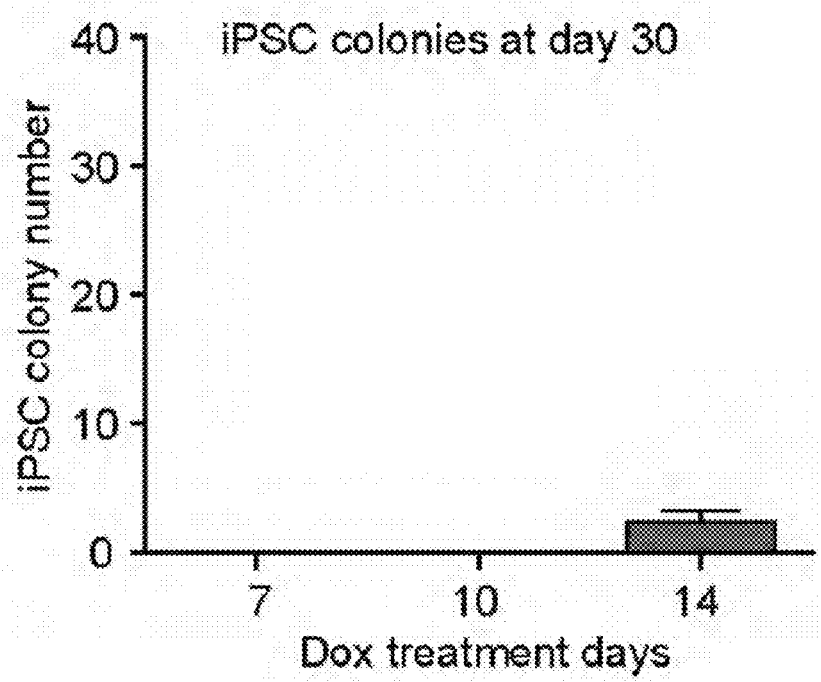
FIG. 5C graphically illustrates the number of induced pluripotent stem cell (iPSC) colonies forming over time from newborn fibroblasts cultured under reprogramming conditions suitable for generating iPSCs. iPSC colonies were identified by NANOG expression (immunostaining).

Doxycycline (Dox)-inducible lentiviruses expressing OCT4, SOX2, and KLF4 were used to compare the temporal dynamics of iMPC-EPC reprogramming to that of reprogramming to pluripotency, i.e., iPSC generation (FIG. 5A). In newborn fibroblast cultures transduced with these viruses and grown under iMPC-EPC reprogramming conditions for 21 days, iMPC-EPC colonies were detected after as few as 7 days of Dox treatment (FIG. 5B). In contrast, iPSC generation required treatment of the transduced cells with Dox for at least 14 days and then growth under iPSC reprogramming conditions for 30 days (FIG. 5B). Thus, newborn fibroblasts reprogram into iMPC-EPCs faster than into iPSCs and expression, of pluripotency markers was not detected at any stage of this process. The methods described herein do not produce a pluripotent intermediate stage.

Example 4: Expansion of the Endodermal Progenitor Cells

Figure 6A:
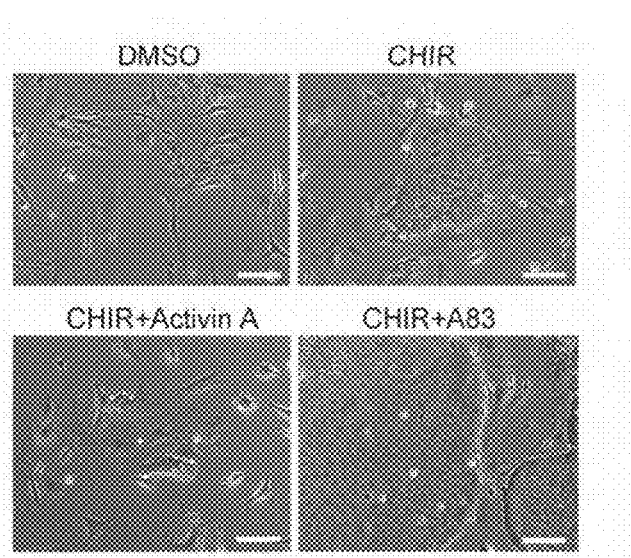
FIG. 6A-6B illustrates expansion of colonies reprogrammed to endoderm fate.
Figure 6B:
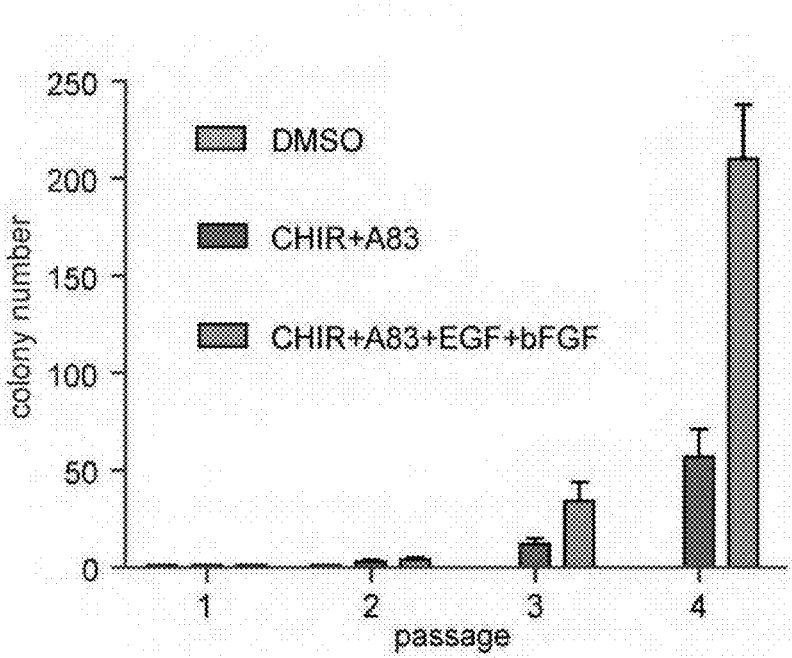

This Example shows that the iMPC-EPCs could be expanded in vitro, a prerequisite for generating the large numbers of cells needed for human liver cell therapy. After screening several small molecule and growth factor combinations, the inventors found that combining and CHIR99021 (a WNT signaling activator/GSK3 inhibitor) with A83-01 (A83), an inhibitor of the transforming growth factor β (TGFβ) type I receptors (Li et al., *Proc Natl Acad Sci USA* 108, 8299-8304, (2011)), increased iMPC-EPC colony size (FIG. 1 and FIG. 6A). Adding EGF and bFGF further increased colony size and facilitated passaging of iMPC-EPCs for more than 25 times, producing more than $1\times10^6$ cells from a single colony (FIG. 2A-2B and FIG. 6B). These cells could be thawed with high viability after cryopreservation (data not shown).

Example 5: Characteristics of the Expanded Endodermal Progenitor Cells

Figure 7:
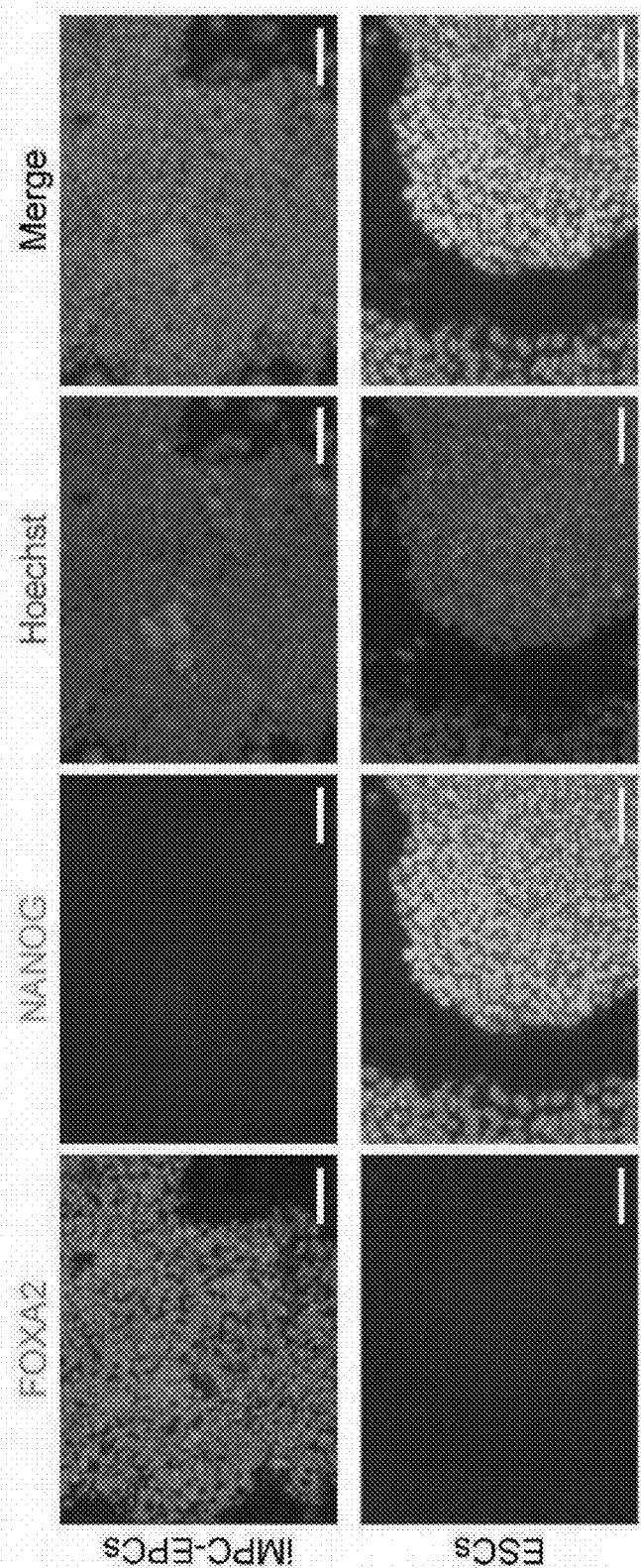
FIG. 7 illustrates that expanded iMPC-EPCs are negative for the pluripotency marker NANOG. Immunostainings show expression of FOXA2, but not NANOG, in passage 7 (P7) iMPC-EPCs. Passage 38 (P38) ESCs were used as controls. Scale bars=100 µm.
Figure 8:
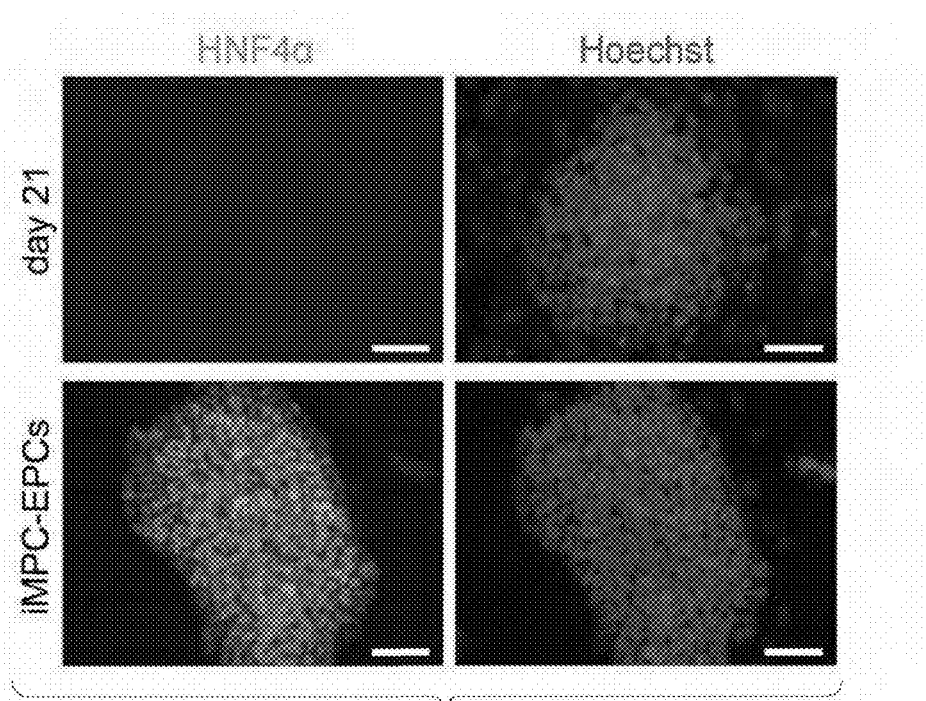
FIG. 8 shows that iMPC-EPCs acquire HNF4α expression. Immunostainings show HNF4α expression in an expanded (passage 4) iMPC-EPC colony, but not at day 21 of the reprogramming step of the protocol. The result indicates that HNF4α expression is induced during the expansion step. Scale bars=100 µm.
Figure 9A:
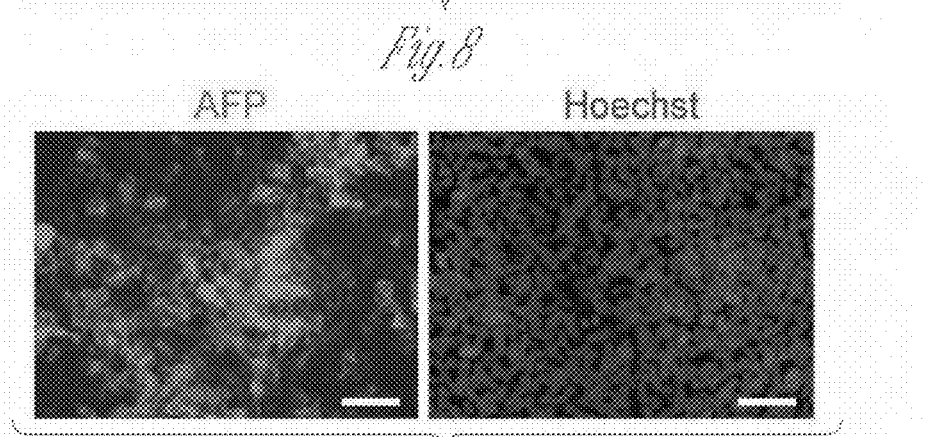
Figure 9B:
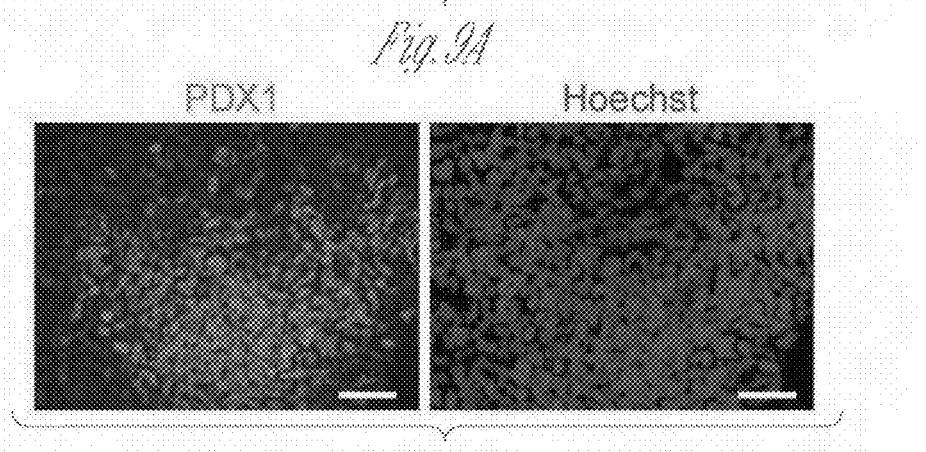

As illustrated in this Example, the iMPC-EPCs maintained an endodermal differentiation state throughout the expansion process. In particular, the expanded iMPC-EPCs expressed SOX17 and FOXA2 but were negative for NANOG expression, as detected by immunostaining (FIG. 2A and FIG. 7). The cells also acquired expression of HNF4α (FIG. 2A and FIG. 8), indicating further specification. To define their stage of differentiation, iMPC-EPCs were compared to definitive endoderm cells (DECs) and primitive gut-tube endoderm cells (GECs) derived from ESCs using methods described by Wang et al. (*Cell Stem Cell* 8, 335-346, (2011)). As shown in FIG. 2C, the expression patterns of iMPC-EPCs closely resembled ESC-GECs, except for lack of expression of (OCT4 and NANOG. The iMPC-EPCs also lacked expression of the ectoderm-specific gene PAX6 and the mesoderm-specific gene BRY, suggesting that they were committed to endoderm differentiation. Further analyses showed that iMPC-EPCs had a propensity for differentiating into specific endoderm lineages, namely hepatic and pancreatic cells, but not lung or intestinal cells (FIG. 9A-9B and data not shown). These results establish the feasibility of generating from newborn fibroblasts highly proliferative endoderm cells that share many characteristics with previously reported ESC/iPSC-derived endodermal progenitor cell lines (Cheng et al., *Cell Stem Cell* 10, 371-384, (2012)), but in contrast to these cell lines, the iMPC-EPCs appear more lineage restricted and never entered a pluripotent state.

Example 6: Differentiation of Endodermal Progenitor Cells into Hepatocytes

Figure 10:
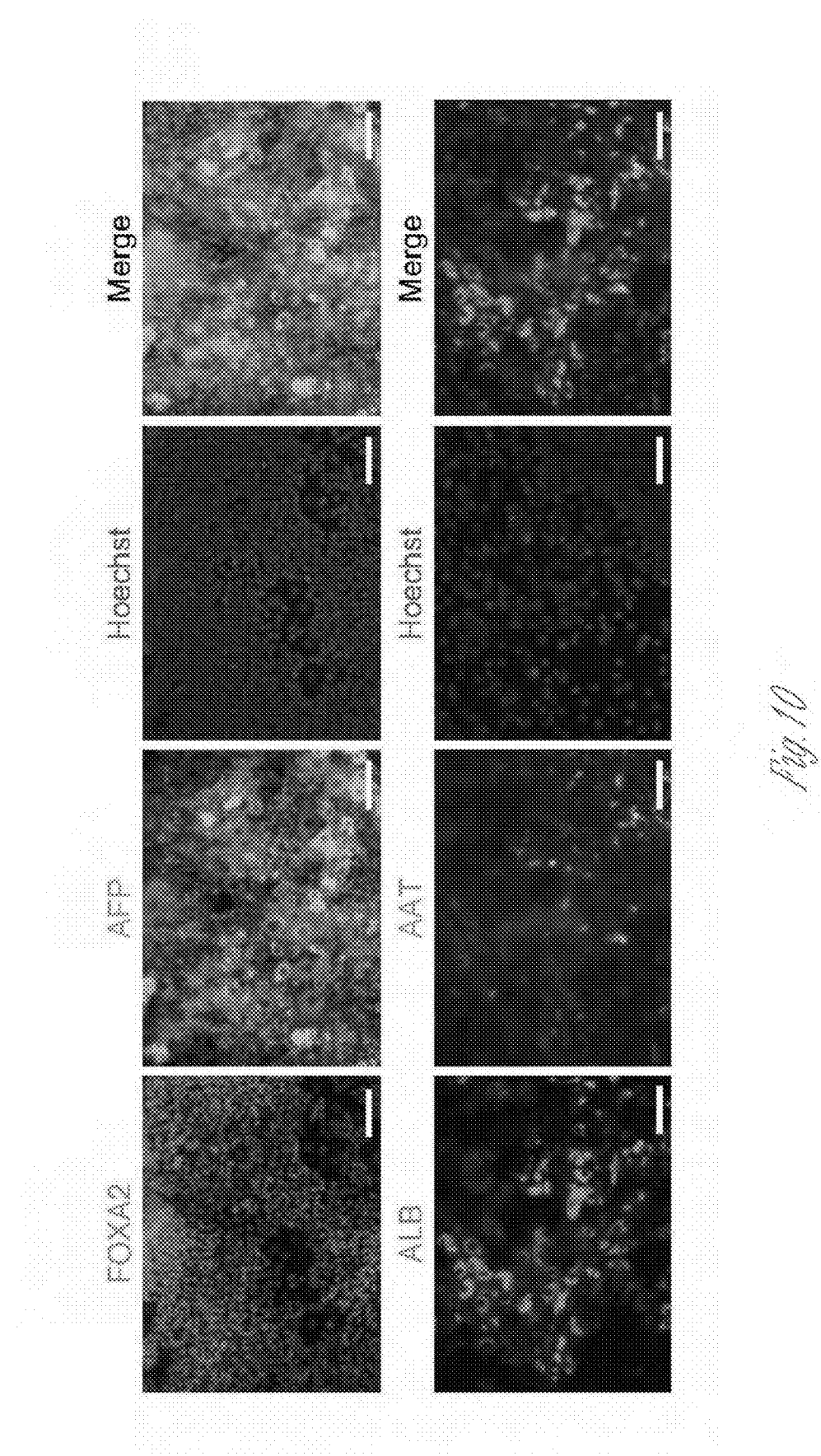
FIG. 10 illustrates the baseline hepatocyte differentiation potential of iMPC-EPCs as detected by immunostainings. As shown, almost all iMPC-EPCs express AFP after sequential exposure to bFGF, BMP4, HGF, Dexamethasone (Dex), and OSM, whereas only a subset of the cells acquires ALB and AAT expression. Scale bars=100 µm.
Figure 11:
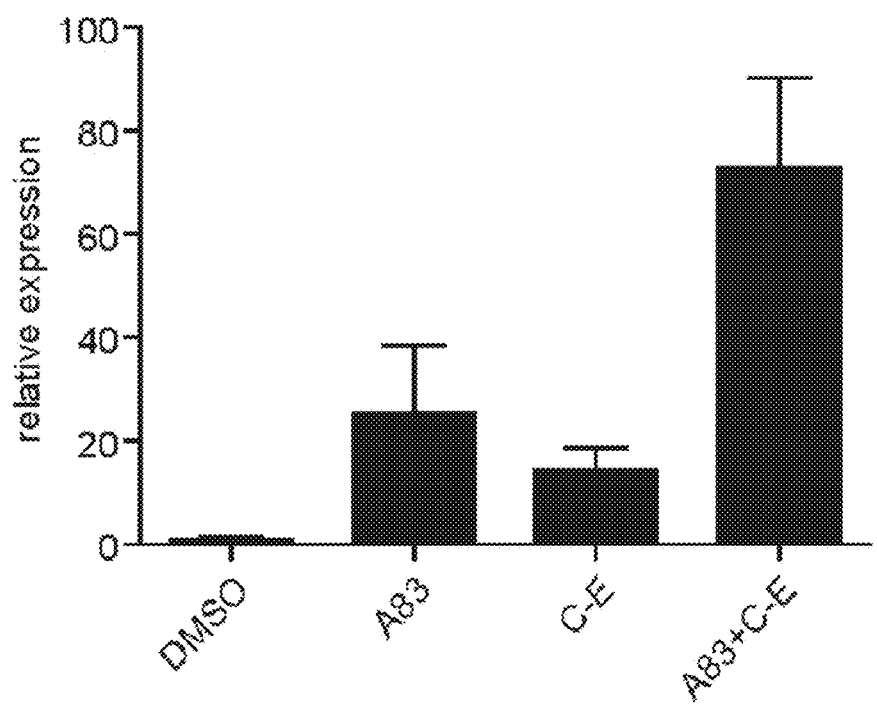
FIG. 11 shows that small molecules promote hepatocyte differentiation as detected by qRT-PCR analysis of albumin (ALB) expression levels at day 18 of the hepatocyte specification step of the protocol. As shown A83 and Compound E exhibit an additive effect in inducing ALB gene expression. Error bars represent SEM of technical replicates (n=3).

To further differentiate iMPC-EPCs into induced multipotent derived hepatocytes (iMPC-Heps), the iMPC-EPCs were cultured in medium containing factors that drive hepatic commitment and hepatocyte differentiation of induced pluripotent stem cell derived definitive endodermal cells (iPSC-DECs) (Si-Tayeb et al., *Hepatology* 51, 297-305, (2010); Rashid et al., *J Clin Invest* 120, 3127-3136, (2010); Ma et al., *Stem Cells Transl Med* 2, 409-419, (2013). Such factors included bFGF, bone morphogenetic protein 4 (BMP4), hepatocyte growth factor (HGF), dexamethasone (Dex), and oncostatin M (OSM). These factors were effective in inducing expression of the fetal hepatocyte marker α-fetoprotein (AFP), but only a few cells expressed more mature hepatocyte markers such as albumin (ALB) or α-1 Antitrypsin (AAT) (FIG. 10). To improve hepatocyte differentiation, small molecules were screened for induction of ALB gene expression. A83 and the Notch inhibitor Compound E (C-E) were effective, particularly when applied together (FIG. 1 and FIG. 11). These results therefore show that inhibiting biliary differentiation promotes differentiation of iMPC-EPCs into iMPC-Heps.

Example 7: Induced Multipotent Derived Hepatocytes (iMPC-Heps) Properties

Figure 12A:
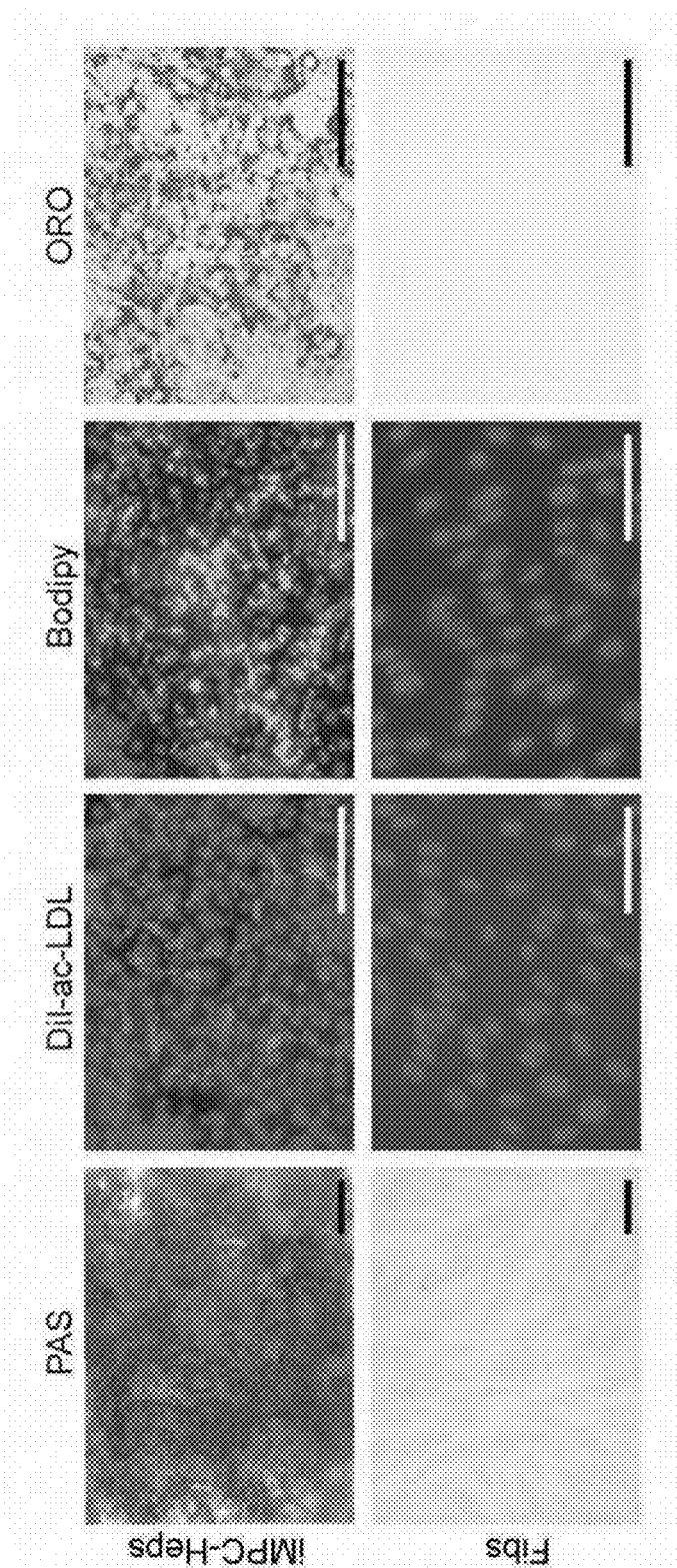
FIG. 12A-12C illustrates hepatocyte function of iMPC-Heps in vitro.
Figure 12B:
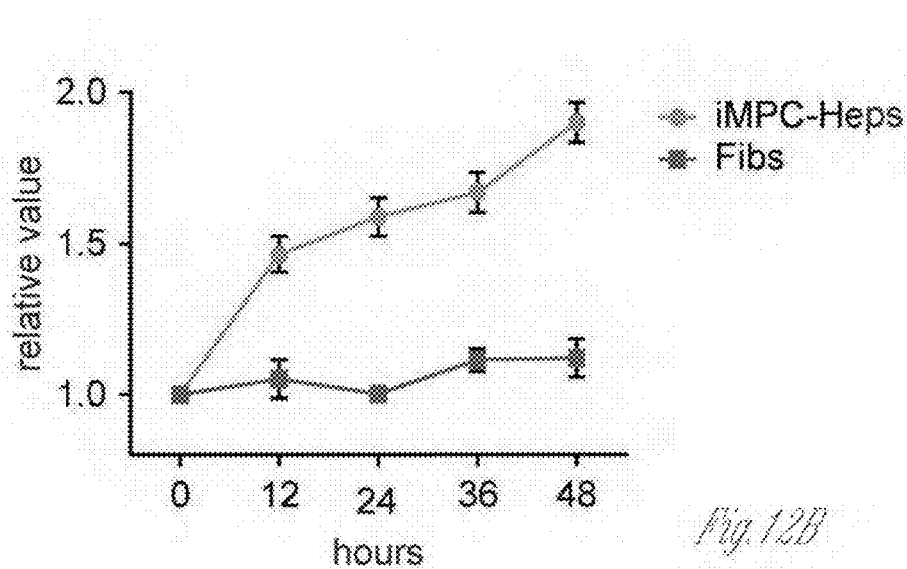
Figure 12C:
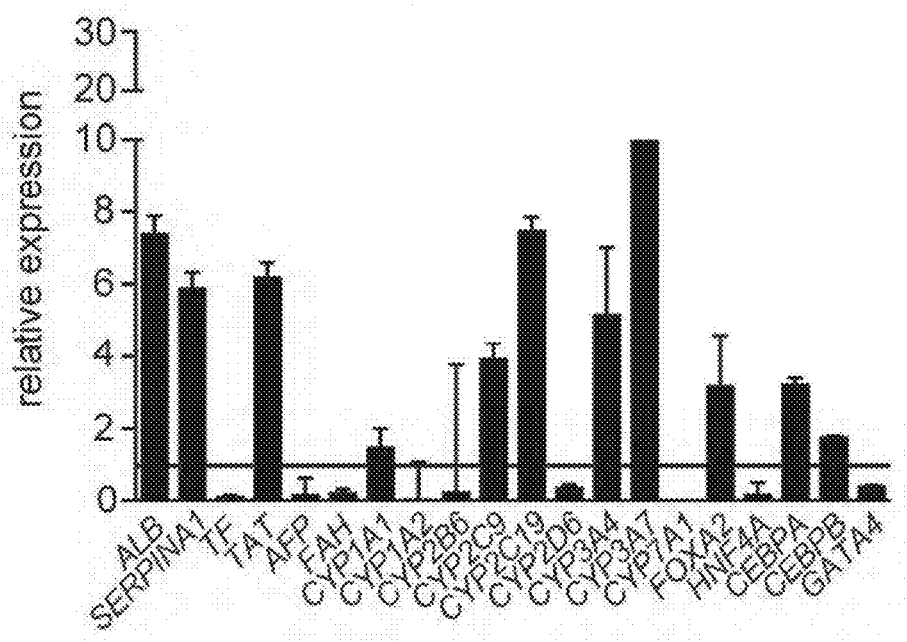
Figure 13A:
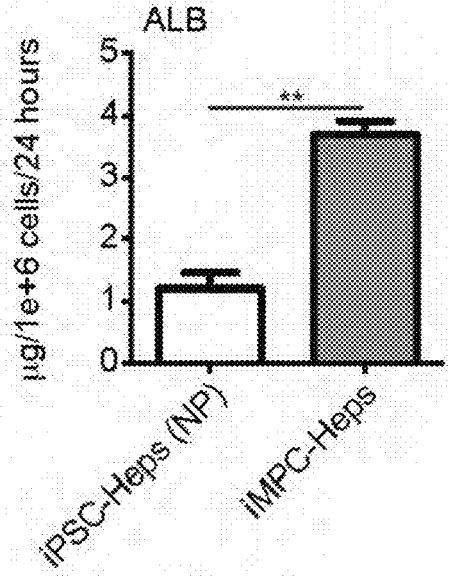
FIG. 13A-13D illustrates in vitro hepatocyte function of iMPC-Heps compared to iPSCs subjected to the iMPC-EPC/Hep generation protocol.
Figure 13B:
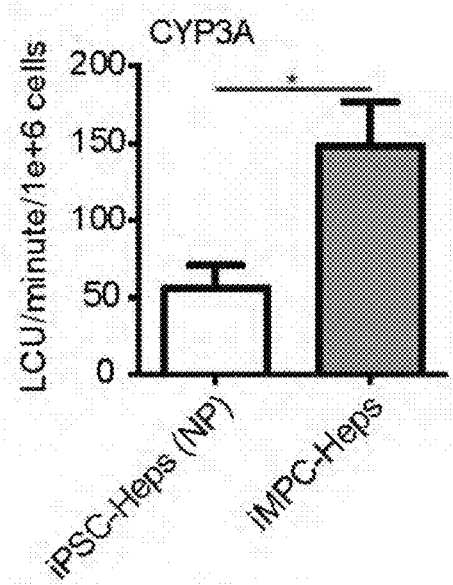
Figure 13C:
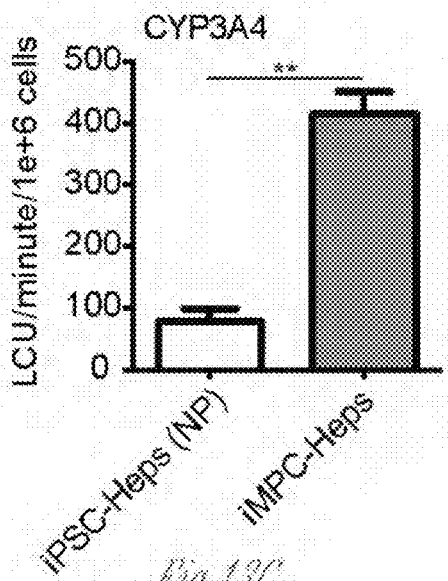
Figure 13D:
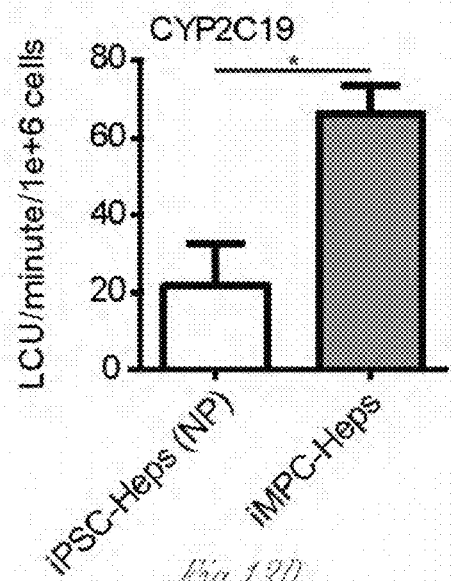

Like adult hepatocytes (aHeps), iMPC-Heps had a polygonal shape, were occasionally binucleated, and expressed the hepatocyte markers HNT4α, ALB, AAT, and cytokeratin 18 (CK18) (FIG. 3a). iMPC-Heps also exhibited hepatocyte functions such as glycogen storage, lipid uptake and storage, and urea production (FIG. 12A-12B). However, not all iMPC-Heps were equally differentiated, as evidenced by some cells not expressing ALB or HNF4α (FIG. 3B). Moreover, analysis of hepatocyte differentiation stage-specific markers by qRT-PCR showed that iMPC-Heps closely resembled human primary fetal hepatocytes (fHeps), including in CYP450 enzyme gene expression levels (FIG. 3C). However, lower AFP gene expression levels suggested that iMPC-Heps were more mature than fetal hepatocytes (fHeps), and also iPSC-Heps generated as reported by Si-Tayeb et al., *Hepatology* 51, 297-305, (2010); Rashid et al., *J Clin Invest* 120, 3127-3136, (2010); Ma et al., *Stem Cells Transl Med* 2, 409-419, (2013). See, FIG. 12C. Analysis of ALB secretion and CYP450 activities confirmed that iMPC-Heps were more differentiated than iPSC-Heps, but comparison to aHeps showed that iMPC-Heps were still immature (FIG. 3D-3G). Applying the growth factor/small molecule-supplemented media used for iMPC-EPC/Hep generation to iPSCs did not produce iPSC-Heps with better secretory or metabolic function, which underscores the importance of the developmental plasticity induced by OCT4, SOX2, and KLF4 in this process (FIG. 13A-13D).

Example 8: Transplantation of iMPC-Heps

To test whether iMPC-Heps can expand after transplantation, $1\times10^6$ cells were transplanted into FRG mice, an immune-deficient mouse model of the human liver disease tyrosinemia type I (Azuma et al., *Nat Biotechnol* 25, 903-910, (2007)). The liver injury caused by this disease creates a growth advantage for differentiated hepatocytes, but not immature liver progenitor cells. Therefore, liver repopulation of FRG mice requires both mature hepatocyte function and the ability to proliferate.

To detect potential expansion of the transplanted iMPC-Heps, human serum albumin (HSA) levels were measured monthly for more than 9 months. The earliest time point when HSA was detectable was two months after transplantation (FIG. 4A). HSA levels were at most 140 ng/mL at this time point, but continuously increased, reaching levels of up to 104 μg/mL six months later. By six months after transplantation, HSA levels were 10-fold higher in control FRG mice transplanted with $1\times10^6$ aHeps than in FRG mice transplanted with iMPC-Heps. The delayed onset but parallel upward trend of HSA levels in iMPC-Hep-transplanted mice, as compared to control mice, indicates that iMPC-Heps had lower engraftment efficiency compared to aHeps. One possibility is that iMPC-Heps need post-transplantation maturation.

Figure 14A:
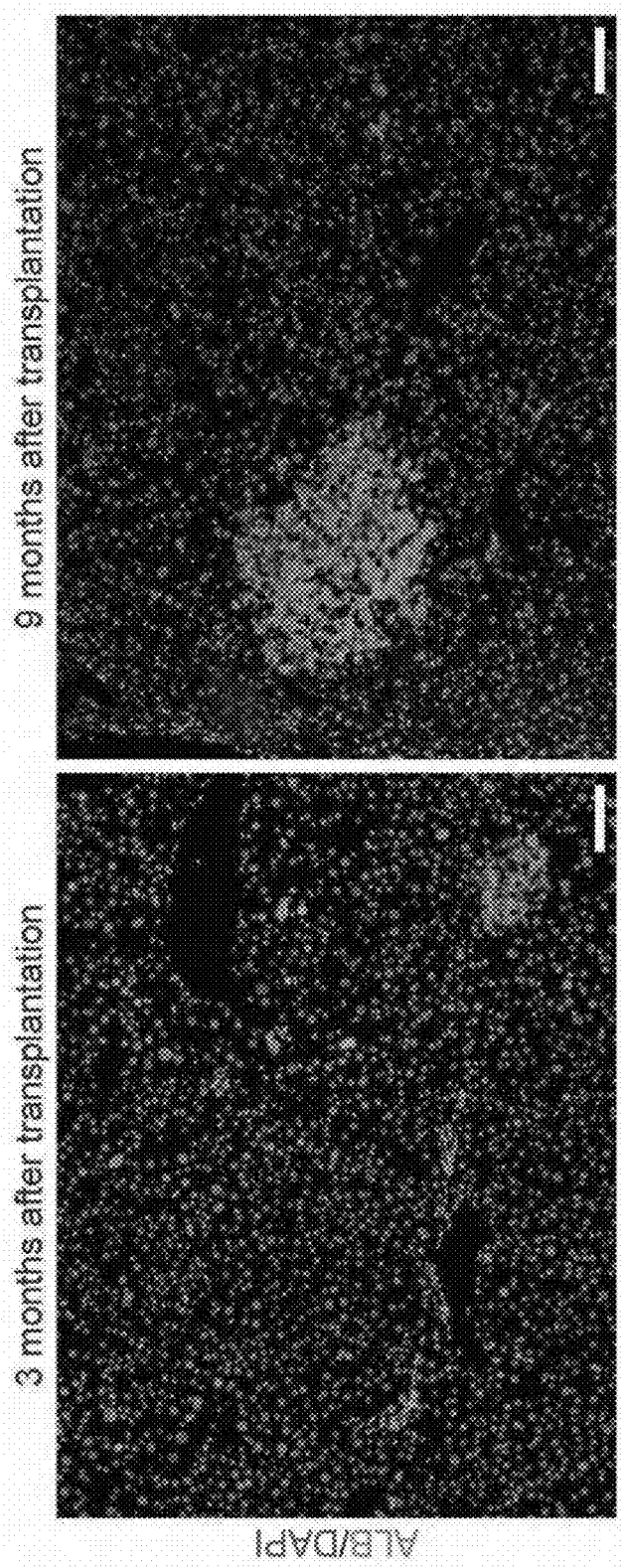
FIG. 14A-14C illustrates the amount (quantity) of liver repopulation by iMPC-Heps as detected by albumin (ALB) and fumarylacetoacetate hydrolase (FAH) immunostaining.
Figure 14B:
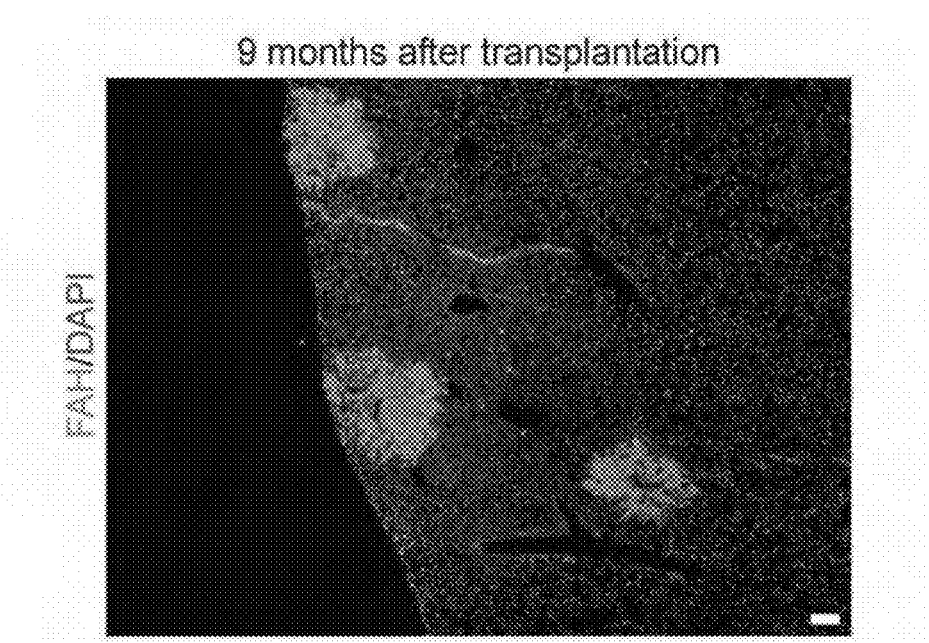
Figure 14C:
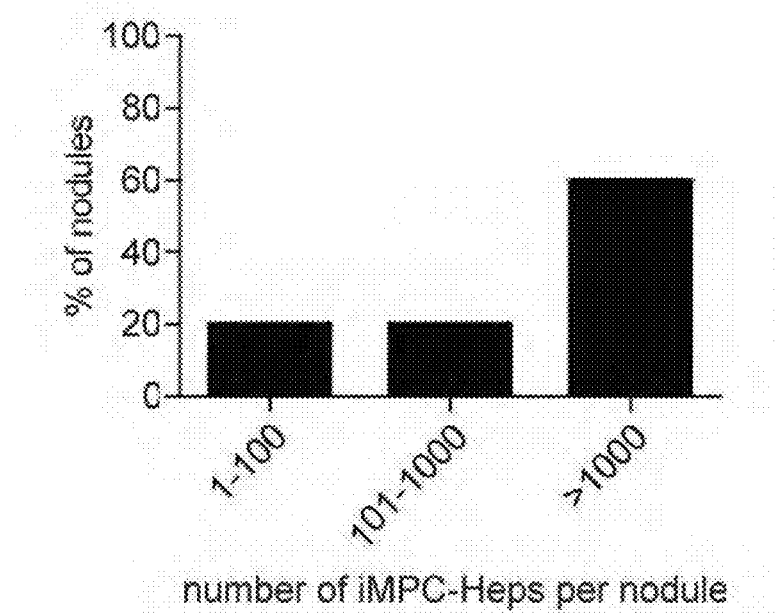

However, the iMPC-Heps were able to proliferate in vivo. Many iMPC-Heps—identified by immunostaining for human-specific ALB—expressed the pan-proliferation marker Ki67 in the periphery of repopulating nodules even as late as 9 months after transplantation (FIG. 4b). Furthermore, the repopulating nodules increased in size over time as evidenced by comparison of mice at 3 and 9 months after iMPC-Hep transplantation (FIG. 14A-14B). To date, the inventors have observed a maximum nodule size of 4,000 iMPC-Heps and a liver repopulation level of 2% (FIG. 14C).

Figure 15B:
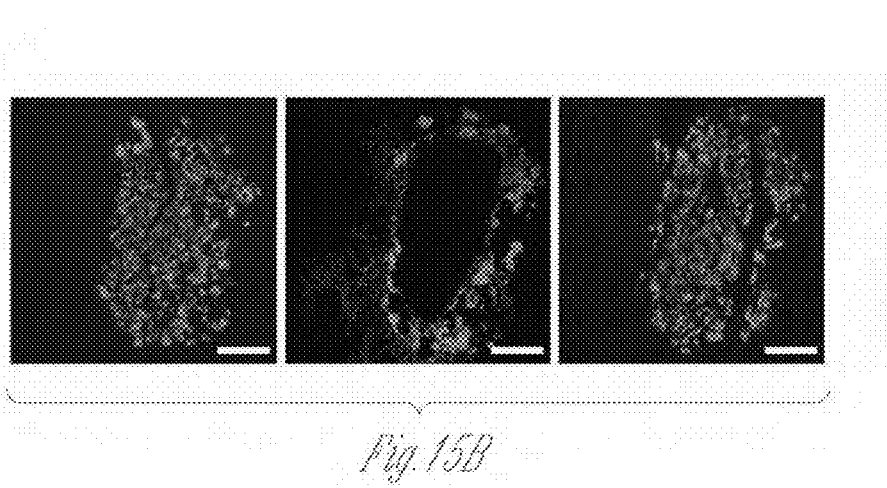
Figure 16A:
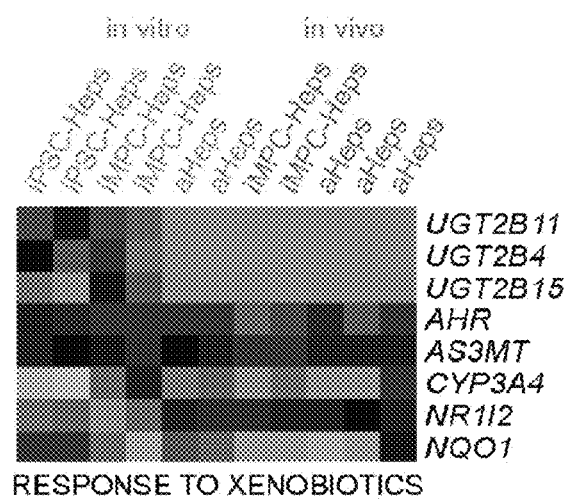
FIG. 16A-16D illustrates expression patterns of iMPC-Heps after in vive maturation based on hepatocyte function-related Gene Ontology (GO) terms. Global gene expression profiling was analyzed using gene sets of the GO terms RESPONSE TO XENOBIOTIC STIMULUS (FIG. 16A), REACTOME CYTOCHROME P450 ARRANGED BY SUBSTRATE TYPE (FIG. 16), BILE ACID METABOLIC PROCESS (FIG. 16C), and GLUCOSE METABOLIC PROCESS (FIG. 16D). GO terms and annotated genes were obtained from Molecular Signatures Database (MSigDB) v4.0.
Figure 16B:
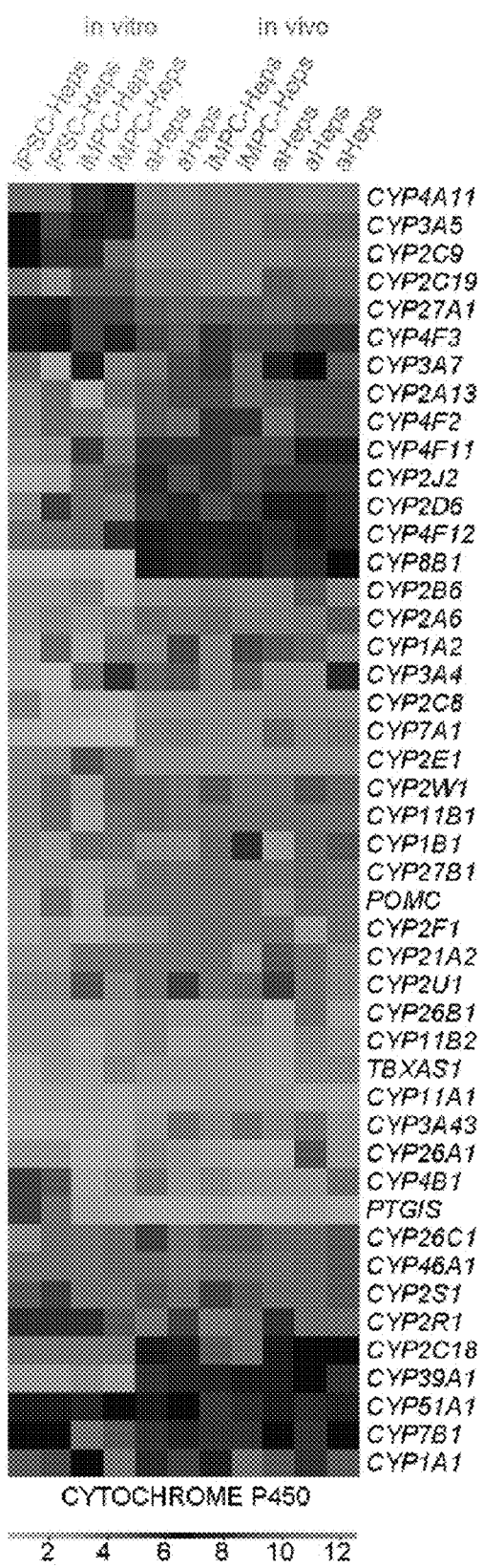
Figure 16C:
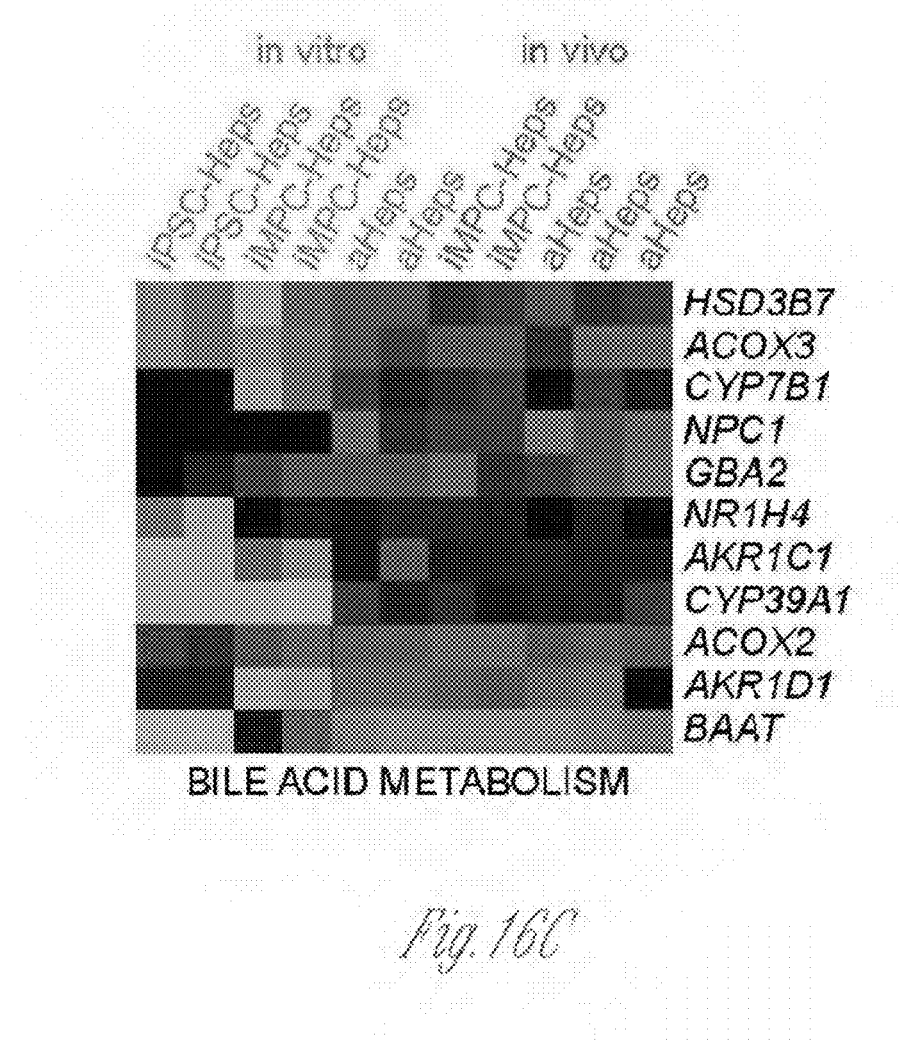
Figure 16D:
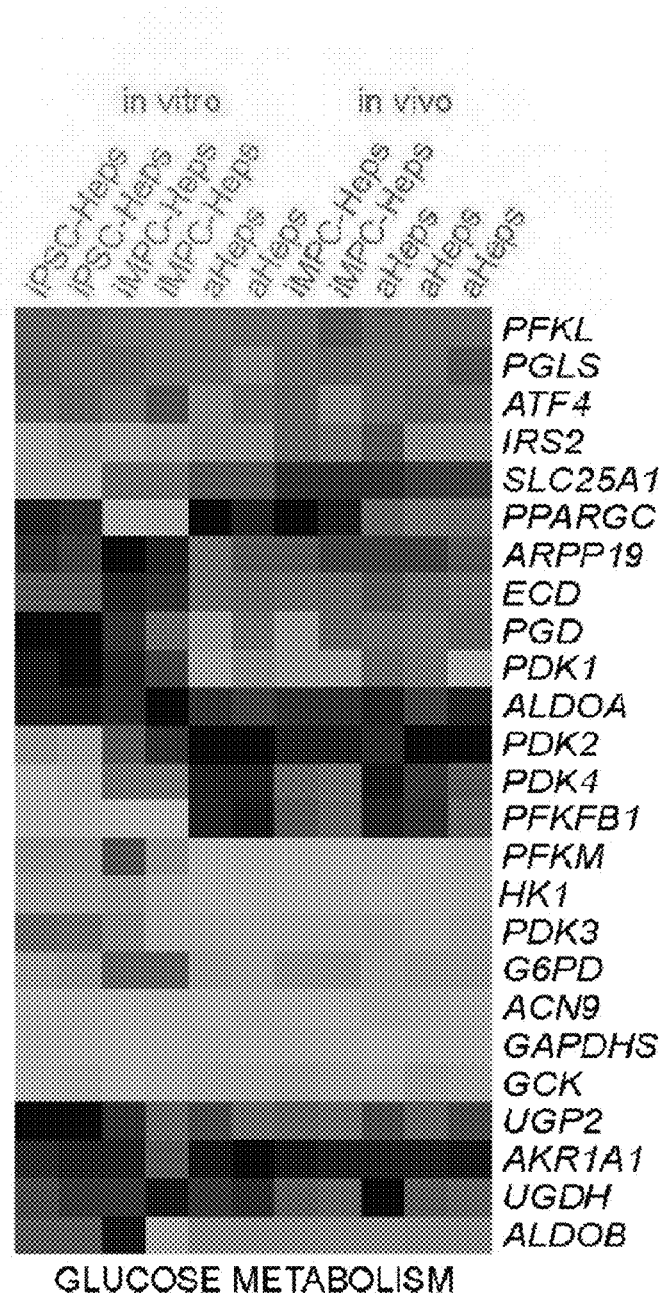
Figure 17:
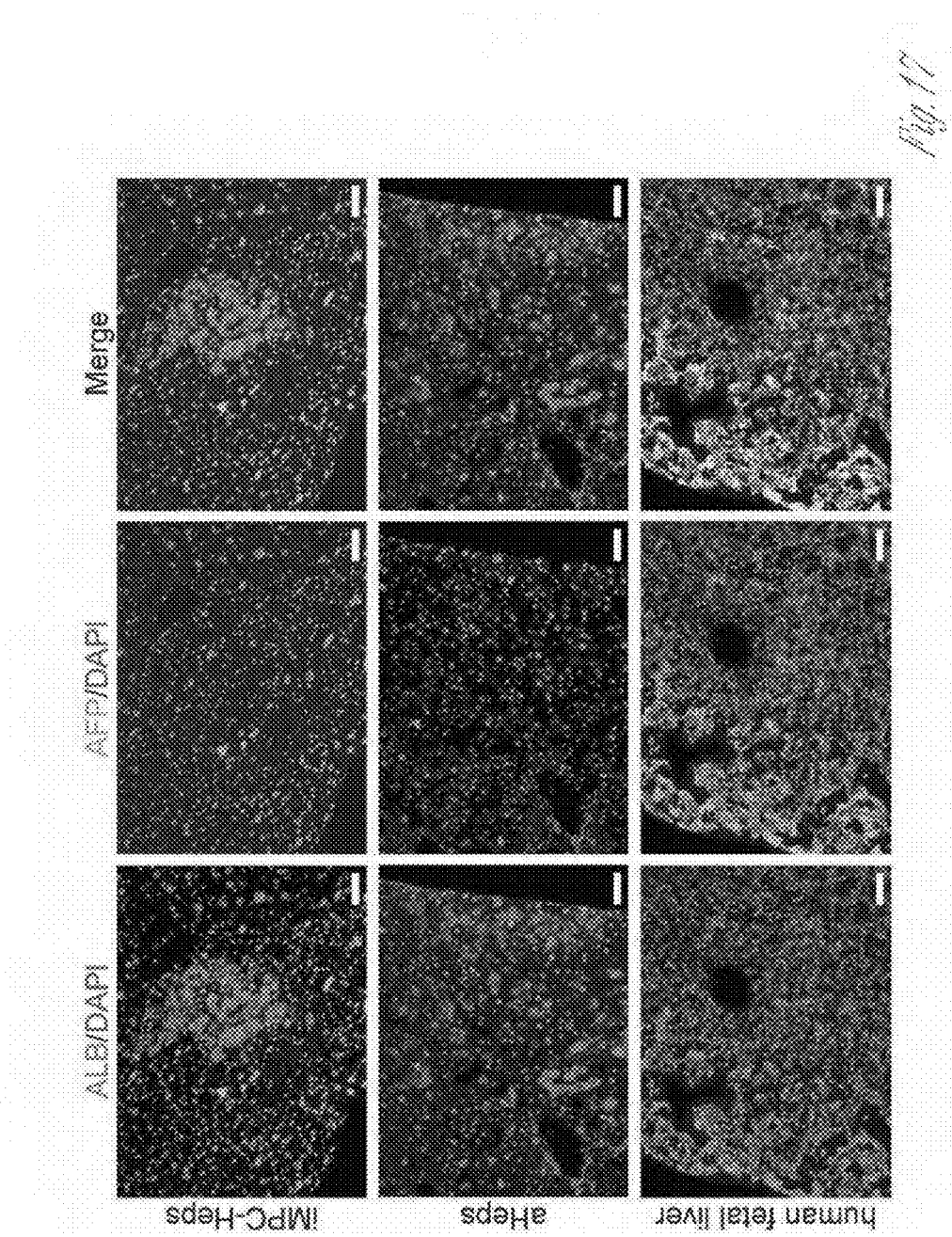

To determine whether iMPC-Heps had indeed matured after transplantation, the global gene expression profile of transplanted iMPC-Heps and aHeps was compared. Repopulating nodules of iMPC-Heps and aHeps were isolated by laser-capture microscopy (LCM) around nine months after transplantation (FIG. 15A-15B), RNA was extracted from the nodules, and the RNA was subjected to microarray analysis.

iMPC-Heps and aHeps were closely clustered together after transplantation; and only a few genes were differentially expressed (FIG. 4C, FIG. 16A-16D, and Supplementary Table). The global gene expression profile of cultured iMPC-Heps was also compared to that of freshly isolated aHeps. The expression patterns of these two cell types were very different from each other, which illustrates the extensive maturation iMPC-Heps had undergone after transplantation (FIG. 4C and FIG. 16A-16D). In fact, before transplantation, the global gene expression profile of iMPC-Heps resembled that of iPSC-Heps (FIG. 4C and FIG. 16A-16D). The microarray results were confirmed by analysis of the expression of genes specific for immature or mature hepatocytes confirmed these by qRT-PCR and immunostaining (FIGS. 4D, 17, 18A and 18B).

Figure 19A:
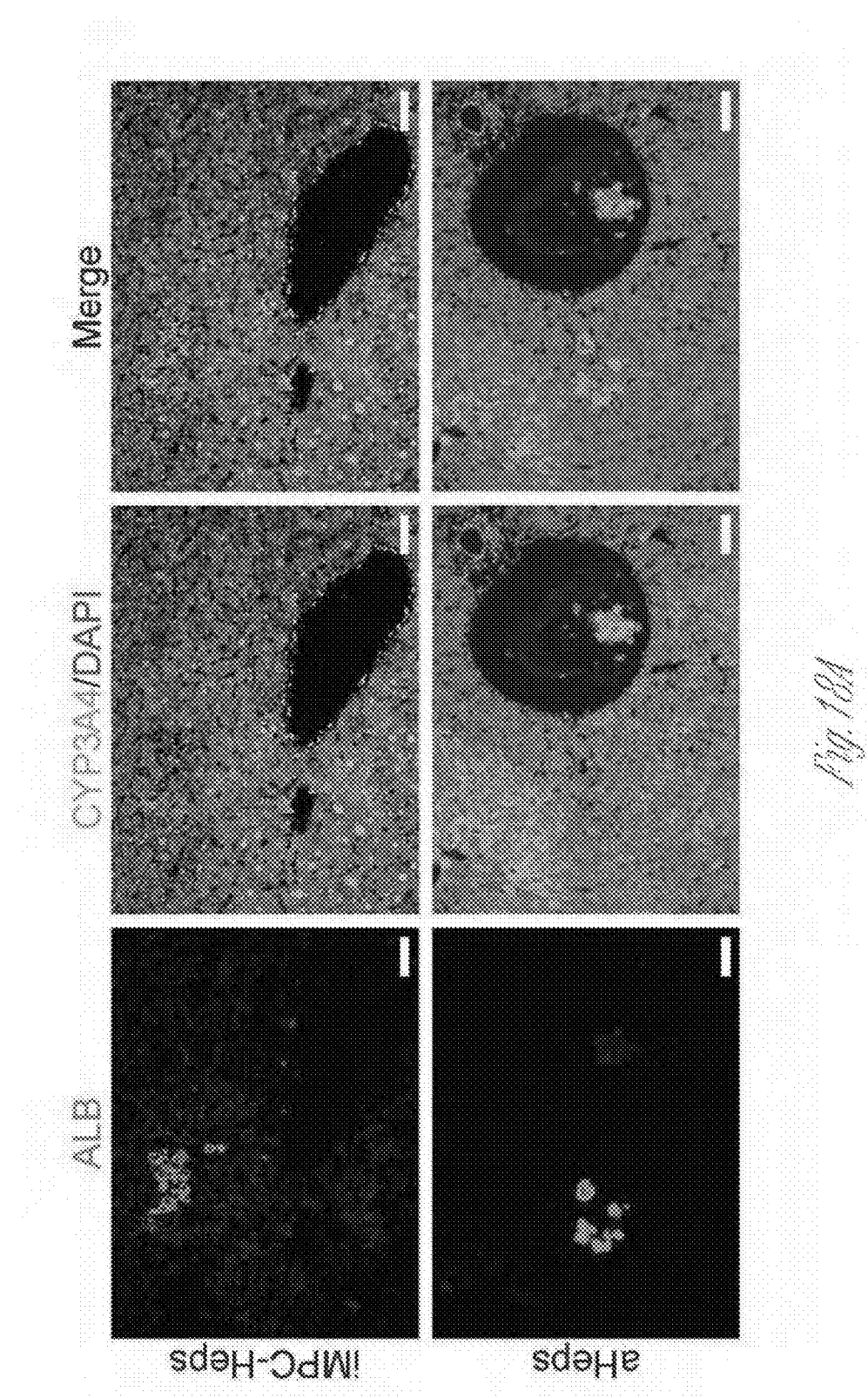
FIG. 19A-19B illustrates the therapeutic efficacy of iMPC-Heps.
Figure 18B:
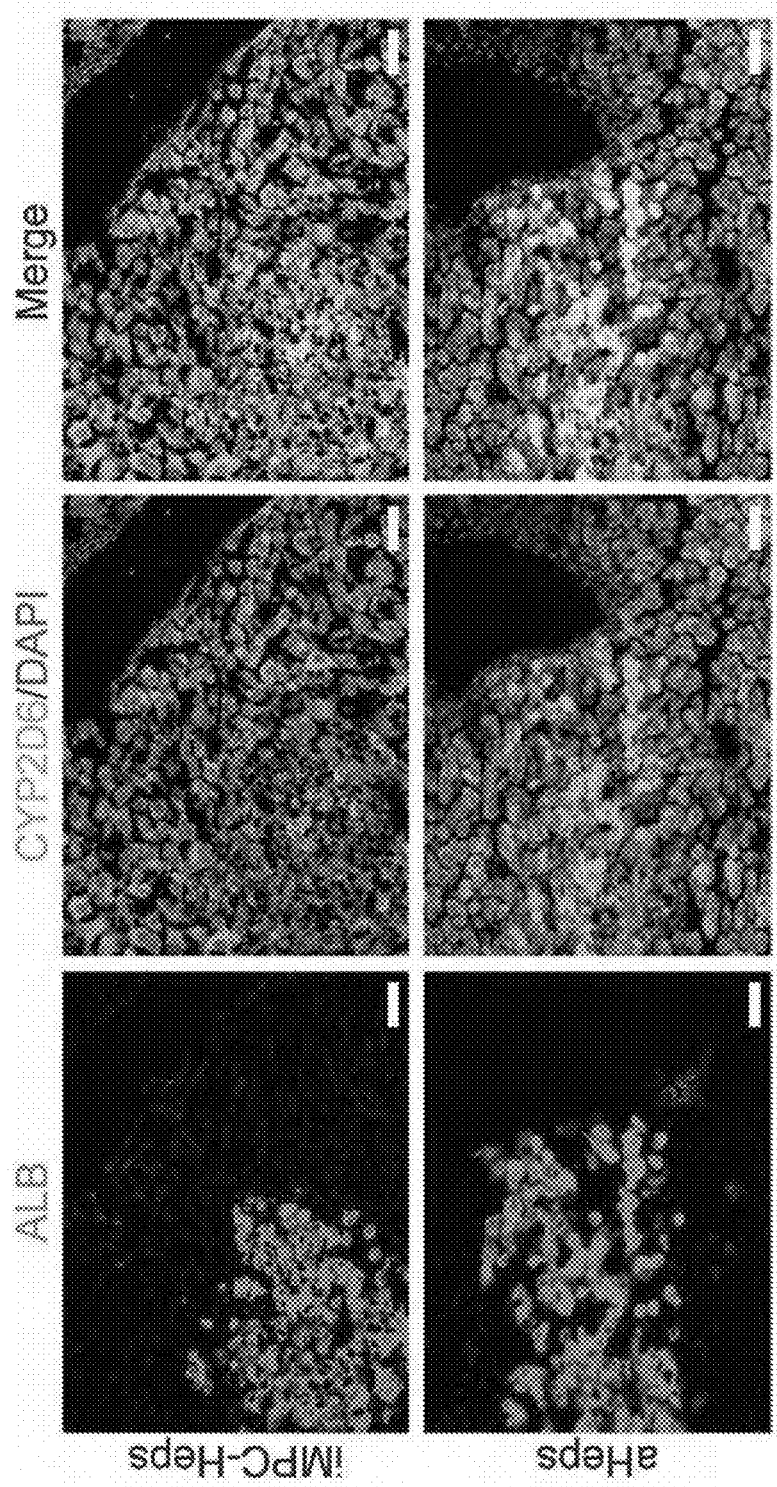
Figure 19A:
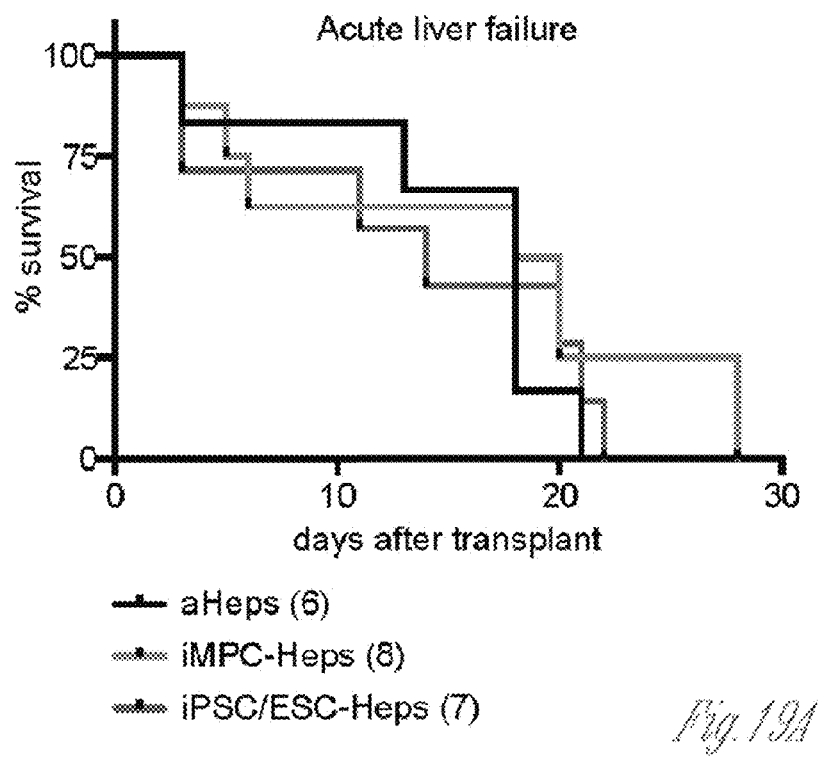
Figure 19B:
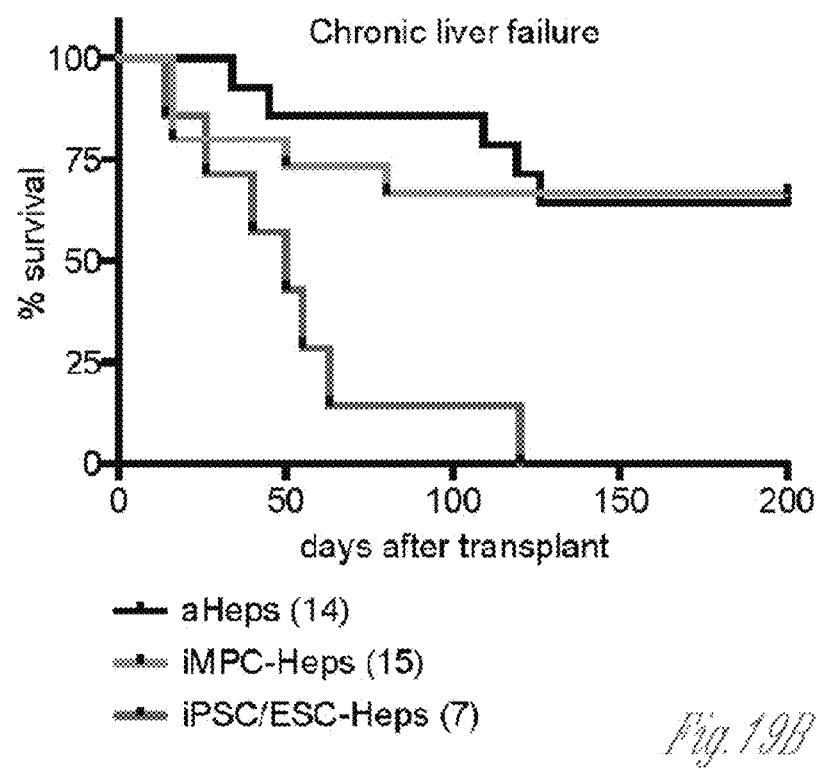

In addition, the inventors determined whether maturation of gene expression translated into normal function by measuring hydroxylation of debrisoquine (DB)—a unique metabolic function of human hepatocytes executed by CYP2D6 (Chen et al., *Proc Natl Acad Sci USA* 108, 11842-11847, (2011))—in mice repopulated to similar levels with iMPC-Heps or aHeps. No difference was observed in plasma 4-hydroxy-debrisoquine (4-OH-DB) levels between these mice, which shows that CYP2D6 had matured in iMPC-Heps from negligible expression levels in vitro to normal activity levels found in aHeps in vivo (FIG. 4E and FIG. 3C). Fusion with mouse hepatocytes was ruled out as the reason for post-transplant maturation and proliferation of iMPC-Heps by showing absence of double-positive cells in repopulating nodules co-immunostained with human- and mouse-specific albumin antibodies (FIG. 4F). In accord with the inventors' finding of a need for post-transplant maturation of iMPC-Heps, iMPC-Hep transplantation improved survival of mice suffering from chronic liver failure, but not from acute liver failure (FIG. 19A-19B).

Figure 20A:
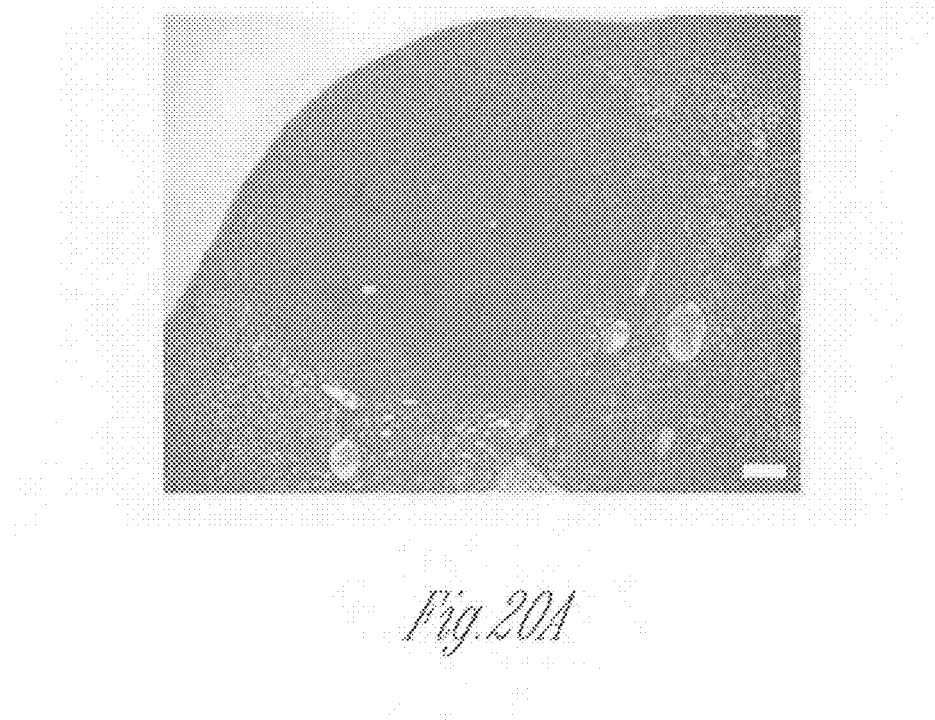

The origin of dysplastic nodules (FIG. 20A) observed in some FRG mice was investigated, both in recipients of iMPC-Heps and aHeps. Differentiation-independent, human-specific β2-microglobulin (B2M) expression was absent, showing that these nodules originated from mouse cells, and therefore represented a known complication of tyrosinemia type I (FIG. 20B) (Willenbring et al., *Cancer Cell* 14, 59-67, (2008)).

The iMPC-Heps are not impacted by major limitations of iPSC/ESC-Heps generated with current protocols, particularly deficiencies in in vivo efficacy and safety. The cells generated by the methods and compositions described herein can mature and proliferate for months after transplantation, demonstrating that they are useful for treatment of liver diseases and conditions.

REFERENCES

1 Si-Tayeb, K. et al. Highly efficient generation of human hepatocyte-*like cells from induced pluripotent stem cells*, *Hepatology* 51, 297-305, (201.0).
2 Rashid, S. T. et al. Modeling inherited metabolic disorders of the liver using human induced pluripotent stem cells. *J Clin Invest* 120, 3127-3136, (2010).
3 Ma, X. et al. Highly efficient differentiation of functional hepatocytes from human induced pluripotent stem cells. *Stem Cells Transl Med* 2, 409-419, (2013).
4 Puppi, J. et al. Improving the techniques for human hepatocyte transplantation: report from a consensus meeting in London. *Cell Transplant* 21, 1-10, (2012).
5 Liu, H., Kim, Y., Sharkis, S., Marchionni, L. & Jang, Y. Y. In vivo liver regeneration potential of human induced pluripotent stem cells from diverse origins. *Sci Transl Med* 3, 82ra39, (2011).
6 Basma, H. et al, Differentiation and transplantation of human embryonic stem cell-derived hepatocytes. *Gastroenterology* 136, 990-999, (2009).
7 Woo. D. H. et al. Direct and indirect contribution of human embryonic stem cell-derived hepatocyte-like cells to liver repair in mice. *Gastroenterology* 142, 602-611, (2012).
8 Azuma, H. et al. Robust expansion of human hepatocytes in Fah$^{-/-}$/Rag2$^{-/-}$/Il2rg$^{-/-}$ mice. *Nat Biotechnol* 25, 903-910, (2007).
9 Szabo, E. et al. Direct conversion of human fibroblasts to multilineage blood progenitors. *Nature* 468, 521-526, (2010).
10 Kurian, L. et al. Conversion of human fibroblasts to angioblast-like progenitor cells. *Nat Methods* 10, 77-83, (2013).
11 Li, J. et al. Conversion of human fibroblasts to functional endothelial cells by defined factors. *Arterioscler Thromb Vasc Biol* 33, 1366-1375, (2013).
12 Takahashi, K. et al. Induction of pluripotent stem cells from adult human fibroblasts by defined factors. *Cell* 131, 861-872, (2007).
13 Zhu, S. et al. Reprogramming of human primary somatic cells by OCT4 and chemical compounds. *Cell Stem Cell* 7, 651-655, (2010).
14 Lee, J. M. et al, A nuclear-receptor-dependent phosphatidylcholine pathway with antidiabetic effects. *Nature* 474, 506-510, (2011).
15 Chan, E. M. et al. Live cell imaging distinguishes bona fide human iPS cells from partially reprogrammed cells. *Nat Biotechnol* 27, 1033-1037, (2009).
16 Li, W. et al. Rapid induction and long-term self-renewal of primitive neural precursors from human embryonic stem cells by small molecule inhibitors. *Proc Natl Acad Sci USA* 1.08, 8299-8304, (2011).
17 Wang, P., Rodriguez, R. T., Wang, J., Ghodasara, A. & Kim, S. K. Targeting SOX17 in human embryonic stem cells creates unique strategies for isolating and analyzing developing endoderm. *Cell Stem Cell* 8, 335-346, (2011).
18 Cheng, X. et al. Self-renewing endodermal progenitor lines generated from human pluripotent stem cells. *Cell Stem Cell* 10, 371-384, (2012).
19 Clotman, F. et al. Control of liver cell fate decision by a gradient of TGF beta signaling modulated by Onecut transcription factors. *Genes Dev* 0.19, 1849-1854, (2005).
20 Kodama, Y., Hijikata, M, Kageyama, R., Shimotohno, K. & Chiba, T. The role of notch signaling in the development of intrahepatic bile ducts. *Gastroenterology* 127, 1775-1786, (2004).
21 Chen, A. A. et al. Humanized mice with ectopic artificial liver tissues. *Proc Natl Acad Sci USA* 108, 11842-11847, (2011).
22 Willenbring, H. et al. Loss of p21 permits carcinogenesis from chronically damaged liver and kidney epithelial cells despite unchecked apoptosis. *Cancer Cell* 14, 59-67, (2008).
23 Lin, T. et al. A chemical platform for improved induction of human iPSCs. *Nat Methods* 6, 805-808, (2009).
24 Song, Z. et al. Efficient generation of hepatocyte-like cells from human induced pluripotent stem cells. *Cell Res* 19, 1233-1242, (2009).
25 Maherali, N. et al. A high-efficiency system for the generation and study of human induced pluripotent stem cells. *Cell Stem Cell* 3, 340-345, (2008).
26 Leeder, J. S. et al. Variability of CYP3A7 expression in human fetal liver. *J Pharmacol Exp Ther* 314, 626-635, (2005).
27 Zhang, X., Ding, L. & Sandford, A. J. Selection of reference genes for gene expression studies in human neutrophils by real-time PCR. *BMC Mol Biol* 6, 4, (2005).
28 Aninat, C. et al. Expression of cytochromes P450, conjugating enzymes and nuclear receptors in human hepatoma HepaRG cells. *Drug Metab Dispos* 34, 75-83, (2006).
29 Xie, C. Q. et al Expression profiling of nuclear receptors in human and mouse embryonic stem cells. *Mol Endocrinol* 23, 724-733, (2009).
30 Lieber, A. et al. Adenovirus-mediated urokinase gene transfer induces liver regeneration and allows for efficient retrovirus transduction of hepatocytes in vivo. *Proc Natl Acad Sci USA* 92, 6210-6214, (1995).
31 Espejel, S. et al. Induced pluripotent stem cell-derived hepatocytes have the functional and proliferative capabilities needed for liver regeneration in mice. *J Clin Invest* 120, 3120-3126, (2010).
32 Wang, X. et al. Kinetics of liver repopulation after bone marrow transplantation. *Am J Pathol* 161, 565-574, (2002).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification

STATEMENTS

1. A composition comprising an epidermal growth factor (EGF), basic fibroblast growth factor (bFGF), an activator of WNT signaling, a nuclear receptor liver receptor homolog 1 agonist, a histone deacetylase (HDAC) inhibitor, a histone demethylase LSD1 inhibitor, a DNA methyltransferase (DNMT) inhibitor, or a combination thereof.

2. The composition of statement 1, containing at least two of the agents, or at least three of the agents, or at least four of the agents, or at least five of the agents, or at least six of the agents.
3. The composition of statement 1 or 2, comprising epidermal growth factor (EGF), basic fibroblast growth factor (bFGF), an activator of WNT signaling, a nuclear receptor liver receptor homolog 1 agonist, a histone deacetylase (HDAC) inhibitor, a histone demethylase LSD1 inhibitor, and a DNA methyltransferase (DNMT) inhibitor.
4. The composition of any of statements 1-3, wherein the WNT agonist is an agent that activates TCF/LEF-mediated transcription in a cell.
5. The composition of any of statements 1-4, wherein the WNT agonist binds and activates a Frizzled receptor family member.
6. The composition of any of statements 1-5, wherein the WNT agonist is a WNT family protein, an inhibitor of intracellular beta-catenin degradation, an activator of TCF/LEF, an inhibitor of GSK-3, or a combination thereof.
7. The composition of any of statements 1-6, wherein the WNT agonist is selected from the group consisting of WNT-3a, a GS K-inhibitor, WNT5, WNT-6a, Norrin, and another WNT family protein.
8. The composition of any of statements 1-7, wherein the GSK3 inhibitor is selected from a group consisting of CHIR99021 (6-(2-(4-(2,4-dichlorophenyl)-5-(4-methyl-1H-imidazol-2-yl)pyrimidin-2-ylamino)ethyl-amino)nicotinonitrile); 1-azakenpaullone (9-Bromo-7,12-dihydro-pyrido[3',2':2,3]azepino[4,5-b]indol-6 (5H)-one), BIO ((2'Z,3'E)-6-Bromoindirubin-3'-oxime); AR-A014418 (N-(4-Methoxybenzyl)-N'-(5-nitro-1,3-thiazol-2-yl)urea); Indirubin 3'-monoxime; 5-Iodo-indirubin-3'-monoxime; kenpaullone (9-Bromo-7,12-dihydroindolo-[3,2-d][1]benzazepin-6 (5H)-one); SB-415286 (3-[(3-Chloro-4-hydroxyphenyl)amino]4-(2-nitro-phenyl)-1H-pyrrole-2,5-dione); SB-216763 (3-(2,4-Dichlorophenyl)-4-(1-methyl-1H-indol-3-yl)-1H-pyrrole-2,5-dione); Maybridge SEW00923SC (2-anilino-5-phenyl-1,3,4-oxadiazole); (Z)-5-(2,3-Methylenedioxyphenyl)-imidazolidine-2,4-dione; TWS119 (3-(6-(3-aminophenyl)-7H-pyrrolo[2,3-d]pyrimidin-4-yloxy)phenol); CHIR98014 (N2-(2-(4-(2,4-dichlorophenyl)-5-(1H-imidazol-1-yl) pyrimidin-2-ylamino)ethyl)-5-nitropyridine-2,6-diamine); SB45286 (3-(3-chloro-4-hydroxyphenylamino)-4-(2-nitrophenyl)-1H-pyrrole-2,5-dione); Tideglusib (2-(1-naphthalenyl)-4-(phenylmethyl)); LY2090314 (3-imidazo[1,2-a] pyridin-3-yl-4-[1,2,3,4-tetrahydro-2-(1-piperidinylcarbonyl)-pyrrolo[3,2,1-jk][1,4] benzodiazepin-7-yl]); lithium salt; and any combination thereof.
9. The composition of any of statements 1-8, wherein the GSK3 inhibitor is CHIR99021, SB216763, TWS119, CHIR98014, Tideglusib (NP031112, NP-12), SB3415286, LY2090314, or any combination thereof.
10. The composition of any of statements 1-9, wherein the GSK3 inhibitor is CHIR99021.
11. The composition of any of statements 1-10, wherein the nuclear receptor liver receptor homolog 1 agonist is a phospholipid.
12. The composition of any of statements 1-11, wherein the nuclear receptor liver receptor homolog 1 agonist is a phosphoinositide.
13. The composition of any of statements 1-12, wherein the nuclear receptor liver receptor homolog 1 agonist is dilauroyl phosphatidylcholine (DLPC).
14. The composition of any of statements 1-13, wherein the histone deacetylase (HDAC) inhibitor is selected from a group consisting of sodium butyrate; phenyl butyrate; butyrate; Suberoylanilide Hydroxamic Acid; BML-210; Depudecin; HC Toxin; Scriptaid; Phenylbutyrate; Valproic Acid; Suramin; Trichostatin A; APHA Compound 8; Apicidin; Trapoxin B; Chlamydocin; Depsipeptide; CI-994; MS-27-275; MGCD0103; NVP-LAQ-824; CBHA; JNJ16241199; Tubacin; 7-[4-(4-cyanophenyl)phenoxy]-heptanohydroxamic acid; Proxamide; Oxamflatin; 3C1-UCHA; CHAP31; or any combination thereof.
15. The composition of any of statements 1-14, wherein the histone deacetylase (HDAC) inhibitor is sodium butyrate.
16. The composition of any of statements 1-15, wherein the histone demethylase LSD1 inhibitor is parnate (tranylcypromine sulfate), a salt of parnate, phenelzine (Nardil, 2-phenylethylhydrazine), a salt of phenelzine, or any combination thereof.
17. The composition of any of statements 1-16, wherein the histone demethylase LSD1 inhibitor is parnate.
18. The composition of any of statements 1-17, wherein the DNA methyltransferase (DNMT) inhibitor is selected from the group consisting of RG108, 5-aza-C, 5-aza-2'-deoxycytidine, decitabine, doxorubicin, EGCG, zebularine and any combination thereof.
19. The composition of any of statements 1-18, wherein the DNA methyltransferase (DNMT) inhibitor is RG108.
20. The composition of any of statements 1-19, further comprising Activin A.
21. The composition of any of statements 1-20, without the epidermal growth factor (EGF).
22. The composition of any of statements 1-21, without the basic fibroblast growth factor (bFGF).
23. The composition of any of statements 1-19, comprising epidermal growth factor (EGF), basic fibroblast growth factor (bFGF), CHIR99021, dilauroyl phosphatidylcholine (DLPC), sodium butyrate, parnate, and RG108.
24. The composition of any of statements 1-19, comprising CHIR99021, dilauroyl phosphatidylcholine (DLPC), sodium butyrate, parnate, and RG108.
25. The composition of any of statements 1-24, further comprising a physiologically acceptable excipient or carrier.
26. The composition of any of statements 1-25 wherein the composition is a cell reprogramming composition.
27. The composition of any of statements 1-26, wherein the agent(s) or compound(s) is present in an amount sufficient to reprogram a cell into a endodermal progenitor cell.
28. The composition of any of statements 1-27, wherein the agent(s) or compound(s) is present in an amount sufficient to induce a cell to express SOX17.
29. The composition of any of statements 1-28, wherein the agent(s) or compound(s) is present in an amount sufficient to induce a cell to express FOXA2.
30. The composition of any of statements 1-29, wherein the agent(s) or compound(s) is present in an amount sufficient to induce a cell to express HNF4α.

31. The composition of any of statements 1-30, wherein the composition does not induce a cell to express OCT4.
32. The composition of any of statements 1-31, wherein the composition does not induce a cell to express Nanog.
33. The composition of any of statements 1-32, further comprising one or more cells.
34. The composition of any of statements 1-33, further comprising one or more cells that express OCT4, SOX2, KLF4, or any combinations thereof.
35. The composition of statement 33 or 34, wherein when the one or more cells is added to the composition the one or more cells is a differentiated cell.
36. The composition of any of statements 33-35, wherein when the one or more cells is added to the composition, the one or more cells is a somatic cell.
37. The composition of any of statements 33-36, wherein when the one or more cells is added to the composition the one or more cells is an adult cell.
38. The composition of any of statements 33-37, wherein when the one or more cells is added to the composition the one or more cells is a multipotent, unipotent, or progenitor cell.
39. The composition of any of statements 33-38, wherein when the one or more cells is added to the composition the one or more cells is a newborn cord blood cell, or a newborn stem cell.
40. The composition of any of statements 33-39, wherein when the one or more cells is added to the composition the one or more cells is an allogenic or autologous cell.
41. The composition of any of statements 33-40, wherein when the one or more cells is added to the composition the one or more cells is not a hepatocyte.
42. The composition of any of statements 33-41, wherein when the one or more cells is added to the composition the one or more cells is not a pluripotent cell.
43. A method comprising incubating one or more cells with the composition of any of statements 1-42.
44. The method of statement 43, wherein when the one or more cells is added to the composition the one or more cells is a differentiated cell.
45. The method of statement 43 or 44, wherein when the one or more cells is added to the composition the one or more cells is a somatic cell.
46. The method of any of statements 43-45, wherein when the one or more cells is added to the composition the one or more cells is an adult cell.
47. The method of any of statements 43-46, wherein when the one or more cells is added to the composition the one or more cells is a multipotent, unipotent, or progenitor cell.
48. The method of any of statements 43-47, wherein when the one or more cells is added to the composition the one or more cells is an induced multipotent cell.
49. The method of any of statements 43-48 wherein when the one or more cells is added to the composition the one or more cells is a newborn cord blood cell, or a newborn stem cell.
50. The method of any of statements 43-49, wherein when the one or more cells is added to the composition the one or more cells is an allogenic or autologous cell.
51. The method of any of statements 43-50, wherein when the one or more cells is added to the composition the one or more cells is not a hepatocyte.
52. The method of any of statements 43-51, wherein when the one or more cells is added to the composition the one or more cells is not a pluripotent cell.
53. The method of any of statements 43-52, wherein the one or more cells is a population of cells.
54. The method of any of statements 43-53, wherein the one or more cells is a heterogeneous or homogeneous mixture of cells.
55. The method of any of statements 43-54, wherein the one or more cells is contacted with the composition for a time and/or with an amount sufficient to induce the one or more cells to express SOX17.
56. The method of any of statements 43-55, wherein the one or more cells is contacted with the composition for a time and/or with an amount sufficient to induce the one or more cells to express FOXA2.
57. The method of any of statements 43-56, wherein the one or more cells is contacted with the composition for a time and/or with an amount sufficient to induce the selected cell to express HNF4α.
58. The method of any of statements 43-57, wherein the one or more cells is contacted with the composition for about 2 days to about 30 days, or from 4 days to about 25 days, or from 5 days to about 23 days, or from 6 days to about 22 days.
59. The method of any of statements 43-58, wherein the one or more cells is contacted with the composition for about 4 days to about 10 days, or from about 6 days to about 8 days, or about 7 days.
60. The method of any of statements 43-59, wherein the composition does not induce a cell to express OCT4.
61. The method of any of statements 43-60, wherein the composition does not induce a cell to express Nanog.
62. The method of any of statements 43-61, which generates induced multipotent cells.
63. The method of any of statements 43-62, which generates endodermal progenitor cells.
64. The method of any of statements 43-63, furthering comprising administering the one or more cells to a subject.
65. The method of any of statements 43-64, furthering comprising administering at least about 100 of the cells to a subject.
66. The method of any of statements 43-65, comprising administering at least about 1000, or at least about 10,000, or at least about 100,000, or at least about 1,000,000, or at least about 10,000,000, or at least about 100,000,000 of the cells to a subject.
67. The method of any of statements 64-66, wherein the subject suffers from a liver condition or disease.
68. The method of any of statements 64-67, wherein the subject suffers from chronic liver failure, tyrosinemia type 1, cirrhosis, hepatitis, alcoholic liver disease, liver cancer, hepatic steatosis, liver fibrosis, primary schlerosing cholangitis, hemochromatosis, Wilson's disease, transthyretin-related hereditary amyloidosis, Gilbert's syndrome, jaundice, or a combination thereof.
69. A method comprising administrating the composition of any of statements 1-42, to a subject.
70. The method of statement 69, wherein the composition contains one or more endodermal progenitor cells and/or one or more hepatocytes.
71. The method of statement 69 or 70, wherein the composition contains one or more allogenic or autologous cell.

72. The method of any of statements 69-71, wherein the composition contains one or more, or at least about 1000, cells that express SOX17.

73. The method of any of statements 69-72, wherein the composition contains one or more, or at least about 1000, cells that express FOXA2.

74. The method of any of statements 69-73, wherein the composition contains one or more, or at least about 1000, cells that express HNF4α.

75. A composition comprising an epidermal growth factor (EGF), basic fibroblast growth factor (bFGF), an activator of WNT signaling, a TGF-β inhibitor, or any combination thereof.

76. The composition of statement 75, containing at least two of the agents, or at least three of the agents.

77. The composition of statement 75 or 76, wherein the WNT agonist is an agent that activates TCF/LEF-mediated transcription in a cell.

78. The composition of any of statements 75-77, wherein the WNT agonist binds and activates a Frizzled receptor family member.

79. The composition of any of statements 75-78, wherein the WNT agonist is a WNT family protein, an inhibitor of intracellular beta-catenin degradation, an activator of TCF-LEF, an inhibitor of GSK-3, or a combination thereof.

80. The composition of any of statements 75-79, wherein the WNT agonist is selected from the group consisting of WNT-3a, a GSK-inhibitor, WNT5, WNT-6a, Norrin, and another WNT family protein.

81. The composition of any of statements 75-80, wherein the GSK3 inhibitor is selected from a group consisting of CHIR99021 (6-(2-(4-(2,4-dichlorophenyl)-5-(4-methyl-1H-imidazol-2-yl)pyrimidin-2-ylamino)ethylamino)nicotinonitrile); 1-azakenpaullone (9-Bromo-7, 12-dihydro pyrido[3',2':2,3]azepino[4,5-b]indol-6 (5H)-one), BIO ((2'Z,3'E)-6-Bromoindirubin-3'-oxime); AR-A014418 (N-(4-Methoxybenzyl)-N'-(5-nitro-1,3-thiazol-2-yl)urea); Indirubin-3'-monoxime; 5-Iodo-indirubin-3'-monoxime; kenpaullone (9-Bromo-7,12-dihydroindolo-[3,2-d][1]benzazepin-6 (5H)-one); SB-415286 (3-[(3-Chloro-4-hydroxyphenyl)amino]-4-(2-nitro-phenyl)-1H-pyrrole-2,5-dione); SB-216763 (3-(2,4-Dichlorophenyl)-4-(1-methyl-1H-indol-3-yl)-1H-pyrrole-2,5-dione); Maybridge SEW00923SC (2-anilino-5-phenyl-1,3,4-oxadiazole); (Z)-5-(2,3-Methylenedioxyphenyl)-imidazolidine-2,4-dione; TWS119 (3-(6-(3-aminophenyl)-7H-pyrrolo[2,3-d]pyrimidin-4-yloxy)phenol); CHIR98014 (N2-(2-(4-(2,4-dichlorophenyl)-5-(1H-imidazol-1-yl) pyrimidin-2-ylamino)ethyl)-5-nitropyridine-2,6-diamine); SB415286 (3-(3-chloro-4-hydroxyphenylamino)-4-(2-nitrophenyl)-1H-pyrrole-2,5-dione); Tideglusib (2-(1-naphthalenyl)-4-(phenylmethyl)); LY2090314 (3-imidazo[1,2-a] pyridin-3-yl-4-[1,2,3,4-tetrahydro-2-(1-piperidinylcarbonyl)-pyrrolo[3,2,1-jk][1,4] benzodiazepin-7-yl]); lithium salt; and any combination thereof.

82. The composition of any of statements 75-81, wherein the GSK3 inhibitor is CHIR99021, SB216763, TWS119, CHIR98014, Tideglusib (NP031112, NP-12), SB415286, LY2090314, or any combination thereof.

83. The composition of any of statements 75-82, wherein the GSK3 inhibitor is CHIR99021.

84. The composition of any of statements 75-83, wherein the TGF-β inhibitor is selected from the group consisting of 4-[4-(1,3-benzodioxol-5-yl)-5-(2-pyridinyl)-1H-imidazol-2-yl]benzamide (SB 431542); 3-(6-Methyl-2-pyridinyl)-N-phenyl-4-(4-quinolinyl)-1H-pyrazole-1-carbothioamide (A83-01); 2-(3-(6-Methylpyridine-2-yl)-1H-pyrazol-4-yl)-1,5-naphthyridine (SJN 2511); 4-[4-(2,3-Dihydro-1,4-benzodioxin-6-yl)-5-(2-pyridinyl)-1H-imidazol-2-yl]benzamide (D 4476); 4-[3-(2-Pyridinyl)-1H-pyrazol-4-yl]-quinoline (LY 364947); 2-(4-(benzo[d][1,3]dioxol-5-yl)-2-tert-butyl-1H-imidazol-5-yl)-6-methylpyridine (SB505124); 6-[2-(1,1-Dimethylethyl)-5-(6-methyl-2-pyridinyl)-1H-imidazol-4-yl]quinoxaline (SB 525334); 2-(5-Chloro-2-fluorophenyl)-4-[(4-pyridyl)amino]pteridine (SD 208); 4-(6-(4-(piperazin-1-yl)phenyl)pyrazolo[1,5-a]pyrimidin-3-yl)quinoline (LDN-193189 and any combination thereof.

85. The composition of any of statements 75-84, wherein the TGFβ inhibitor is A83.

86. A method of expanding endodermal progenitor cells comprising incubating endodermal progenitor cells with the composition of any of statements 74-84 to thereby generate an expanded population of endodermal progenitor cells.

87. The method of statement 85, furthering comprising administering the one or more cells from the expanded population of endodermal progenitor cells to a subject.

88. The method of statement 86 or 87, furthering comprising administering at least about 100 cells from the expanded population of endodermal progenitor cells to a subject.

89. The method of any of statements 86-88, further comprising administering at least about 1000 cells, or at least about 10,000 cells, or at least about 100,000 cells, or at least about 1,000,000 cells, or at least about 10,000,000 cells, or at least about 100,000,000 cells from the expanded population of endodermal progenitor cells to a subject.

90. A composition comprising basic fibroblast growth factor (bFGF), bone morphogenetic protein 4 (BMP4), TGFβ inhibitor, dexamethasone (Dex), hepatocyte growth factor (HGF), a Notch inhibitor, oncostatin M (OSM) or any combination thereof.

91. The composition of statement 90, wherein the TGF-3 inhibitor is selected from the group consisting of 4-[4-(1,3-benzodioxol-5-yl)-5-(2-pyridinyl)-1H-imidazol-2-yl]benzamide (SB 431542); 3-(6-Methyl-2-pyridinyl)-N-phenyl-4-(4-quinolinyl)-1H-pyrazole-1-carbothioamide (A83-01); 2-(3-(6-Methylpyridine-2-yl)-1H-pyrazol-4-yl)-1,5-naphthyridine (SJN 2511); 4-[4-(2,3-Dihydro-1,4-benzodioxin-6-yl)-5-(2-pyridinyl)-1H-imidazol-2-yl]benzamide (D 4476); 4-[3-(2-Pyridinyl)-1H-pyrazol-4-yl]-quinoline (LY 364947); 2-(4-(benzo[d][1,3]dioxol-5-yl)-2-tert-butyl-1H-imidazol-5-yl)-6-methylpyridine (SB505124); 6-[2-(1,1-Dimethylethyl)-5-(6-methyl-2-pyridinyl)-1H-imidazol-4-yl]quinoxaline (SB 525334); 2-(5-Chloro-2-fluorophenyl)-4-[(4-pyridyl)amino]pteridine (SD 208); 4-(6-(4-(piperazin-1-yl)phenyl)pyrazolo[1,5-a]pyrimidin-3-yl)quinoline (LDN-193189 and any combination thereof.

92. The composition of statement 90 or 91, wherein the TGFβ inhibitor is A83.

93. The composition of any of statements 90-91, wherein the Notch inhibitor inhibits Notch signaling, inhibits Notch transcription, inhibits Notch translation, competitively inhibits Notch, inhibits gamma-secretase, or any combination thereof.

94. The composition of any of statements 90-93, wherein the Notch inhibitor is selected from the group consisting of Compound E, RO4929097, DAPT, Gamma-Secretase Inhibitor I, Gamma-Secretase Inhibitor II, and any combination thereof.
95. The composition of any of statements 90-94, wherein the Notch inhibitor is Compound E.
96. A method comprising incubating one or more endodermal progenitor cells and/or one or more immature hepatocytes in the composition of any of statements 90-95 to thereby generate hepatocytes.
97. A method comprising incubating one or more non-pluripotent cells that express OCT4, SOX2, and KLF4, with a composition comprising epidermal growth factor (EGF), basic fibroblast growth factor (bFGF), CHIR99021, dilauroyl phosphatidylcholine (DLPC), sodium butyrate, parnate, and RG108 for about 5 to 9 days to generate one or more induced multipotent cells.
98. A method comprising incubating one or more induced multipotent cells in a composition comprising CHIR99021, dilauroyl phosphatidylcholine (DLPC), sodium butyrate, parnate, RG108 and Activin A for about 10 to 25 days to generate one or more endodermal progenitor cells.
99. A method comprising expanding one or more endodermal progenitor cells in a composition comprising epidermal growth factor (EGF), basic fibroblast growth factor (bFGF), and A83 for about 5 days to about 6 months to generate an endodermal progenitor cell population.
100. A method comprising incubating one or more endodermal progenitor cells with basic fibroblast growth factor (bFGF), A83, bone morphogenetic protein 4 (BMP4), dexamethasone (Dex), for about 2 days to about 8 days to generate immature hepatocytes.
101. A method comprising incubating one or more immature hepatocytes with a composition comprising A83, hepatocyte growth factor (HGF), compound E, and oncostatin M (OSM) to generate mature hepatocytes.
102. A method comprising:
    a. incubating one or more non-pluripotent cells that express OCT4, SOX2, and KLF4, with a composition comprising epidermal growth factor (EGF), basic fibroblast growth factor (bFGF), CHIR99021, dilauroyl phosphatidylcholine (DLPC), sodium butyrate, parnate, and RG108 for about 5 to 9 days to generate one or more induced multipotent cells;
    b. incubating the induced multipotent cells in a composition comprising CHIR99021, dilauroyl phosphatidylcholine (DLPC), sodium butyrate, parnate, RG108 and Activin A for about 10 to 25 days to generate one or more endodermal progenitor cells;
    c. expanding the endodermal progenitor cells in a composition comprising epidermal growth factor (EGF), basic fibroblast growth factor (bFGF), and A83 for about 5 days to about 6 months to generate an endodermal progenitor cell population;
    d. incubating the endodermal progenitor cell population with basic fibroblast growth factor (bFGF), A83, bone morphogenetic protein 4 (BMP4), dexamethasone (Dex), for about 2 days to about 8 days to generate immature hepatocytes;
    e. incubating the immature hepatocytes with a composition comprising A83, hepatocyte growth factor (HGF), compound E, and oncostatin M (OSM) to generate hepatocytes.
103. The method of statement 102, further comprising administering the induced multipotent cells, the endodermal progenitor cells, the immature hepatocytes, the hepatocytes, or any combination thereof to a subject.
104. The method of statement 102 or 103, comprising administering at least about 1000, or at least about 10,000, or at least about 100,000, or at least about 1,000,000, or at least about 10,000,000, or at least about 100,000,000 of the induced multipotent cells, the endodermal progenitor cells, the immature hepatocytes, the hepatocytes, or any combination thereof to a subject.
105. The method of statement 103 or 104, wherein the subject suffers from a liver condition or disease.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound," "a cell," "a nucleic acid" or "a polypeptide" includes a plurality of such compounds, cells, nucleic acids or polypeptides (for example, a solution of cells, nucleic acids or polypeptides, a suspension of cells, or a series of compound, cell, nucleic acid or polypeptide preparations), and so forth. As used herein, the term "and/or" means any one of the items, any combination of the items, or all of the items with which this term is associated. In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, apparatus, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed:

1. A method comprising incubating one or more cells with:

a first composition comprising an epidermal growth factor (EGF), a basic fibroblast growth factor (bFGF), an activator of WNT signaling, a nuclear receptor liver receptor homolog 1 agonist, a histone deacetylase (HDAC) inhibitor, a histone demethylase LSD1 inhibitor, and a DNA methyltransferase (DNMT) inhibitor to generate induced multipotent cells.

2. The method of claim 1, wherein the one or more cells is a heterogeneous or homogeneous mixture of cells.

3. The method of claim 1, wherein the one or more cells is incubated with the first composition for a time and with an amount of the composition sufficient to induce the one or more cells to express SOX17 FOXA2, HNF4α, or any combination thereof.

4. The method of claim 1, wherein the one or more cells is incubated with the first composition for about 2 days to about 30 days, or from 3 days to about 25 days, or from 4 days to about 20 days, or from 5 days to about 9 days.

5. The method of claim 1, wherein the composition does not induce a cell to express OCT4, Nanog, or a combination thereof.

6. The method of claim 1, furthering comprising administering the one or more cells to a subject after incubation of the cell(s) in the composition.

7. The method of claim 1, further comprising incubating one or more of the induced multipotent cells with a second composition comprising an activator of WNT signaling, a nuclear receptor liver receptor homolog 1 agonist, a histone deacetylase (HDAC) inhibitor, a histone demethylase LSD1 inhibitor, a DNA methyltransferase (DNMT) inhibitor, Activin A, or any combination thereof to generate one or more endodermal progenitor cells.

8. The method of claim 7, wherein the one or more induced multipotent cells is incubated with the second composition for about 5 to 33 days with an amount of the second composition sufficient to induce the one or more endodermal progenitor cells.

9. The method of claim 7, furthering comprising administering one or more cells to a subject after incubation of the cell(s) in the composition.

10. The method of claim 7, further comprising incubating the one or more endodermal progenitor cells with a third composition comprising epidermal growth factor (EGF), basic fibroblast growth factor (bFGF), and a TGF-beta inhibitor.

11. The method of claim 7, wherein the one or more endodermal progenitor cells in the third composition for a time and in a sufficient amount of the third composition to generate an endodermal progenitor cell population.

12. The method of claim 11, furthering comprising administering one or more cells from the endodermal progenitor cell population to a subject.

13. The method of claim 7, further comprising incubating one or more endodermal progenitor cells in a fourth composition comprising basic fibroblast growth factor (bFGF), a TGF-beta inhibitor, bone morphogenetic protein 4 (BMP4), and dexamethasone.

14. The method of claim 13, comprising incubating one or more endodermal progenitor cells in the fourth composition for a time and in a sufficient amount of the composition to generate one or more immature hepatocytes.

15. The method of claim 13, further comprising incubating one or more endodermal progenitor cells, or one more immature hepatocytes, or a combination thereof in a fifth composition comprising a TGF-beta inhibitor, hepatocyte growth factor, a Notch inhibitor, oncostatin M (USM), or any combination thereof.

16. The method of claim 15, comprising incubating one or more endodermal progenitor cells, or one more immature hepatocytes, or a combination thereof in the fifth composition for a time and in a sufficient amount of the composition to generate one or more mature hepatocytes.

17. The method of claim 16, further comprising administering one or more mature hepatocytes to a subject.

18. The method of claim 17, wherein the subject suffers from a liver condition or disease.

19. The method of claim 18, wherein the liver condition or disease is chronic liver failure, tyrosinemia type L cirrhosis, Alagille syndrome, hepatitis, alcoholic liver disease, liver cancer, hepatic steatosis, liver fibrosis, liver cysts, primary schlerosing cholangitis, hemochromatosis, Wilson's disease, alcoholic hepatitis, enlarged liver, transthyretin-related hereditary amyloidosis, Gilbert's syndrome, jaundice, liver hemangioma, non-alcoholic fatty liver disease, nonalcoholic steatohepatitis, primary sclerosing cholangitis, or a combination thereof.

* * * * *

UNITED STATES PATENT AND TRADEMARK OFFICE
CERTIFICATE OF CORRECTION

PATENT NO. : 10,227,565 B2  
APPLICATION NO. : 15/361900  
DATED : March 12, 2019  
INVENTOR(S) : Zhu et al.

Page 1 of 2

It is certified that error appears in the above-identified patent and that said Letters Patent is hereby corrected as shown below:

On the Title Page

Item (73), in "Assignees", in Column 1, Line 2, delete "San Francisco, CA (US), A" and insert --a-- therefor In Column 2, item (56), under "Foreign Patent Documents", Line 1, delete "2004067896" and insert --2004087896-- therefor On page 2, in Column 2, item (56), under "Other Publications", Line 11, delete "primative" and insert --primitive-- therefor On page 2, in Column 2, item (56), under "Other Publications", Line 14, after "differentiation", insert --of--

On page 2, in Column 2, item (56), under "Other Publications", Line 24, delete "Inhibtors"," and insert --Inhibitors",-- therefor On page 2, in Column 2, item (56), under "Other Publications", Line 27, delete "Heaptocyte-Like" and insert --Hepatocyte-Like-- therefor In the Claims In Column 89, Line 67, in Claim 1, delete "hi stone" and insert --histone-- therefor In Column 91, Line 2, in Claim 3, after "SOX17", insert --,--

In Column 92, Line 17, in Claim 15, delete "(USM)," and insert --(OSM),-- therefor Signed and Sealed this  
Twenty-eighth Day of April, 2020

Andrei Iancu  
*Director of the United States Patent and Trademark Office*

In Column 92, Line 29, in Claim 19, delete "type L" and insert --type I,-- therefor In Column 92, Line 32, in Claim 19, delete "schlerosing" and insert --sclerosing-- therefor

SEQUENCE LISTING

```
<160> NUMBER OF SEQ ID NOS: 71

<210> SEQ ID NO 1
<211> LENGTH: 426
<212> TYPE: PRT
<213> ORGANISM: Homo sapiens

<400> SEQUENCE: 1

Met Pro Leu Leu Trp Leu Arg Gly Phe Leu Leu Ala Ser Cys Trp Ile
 1               5                  10                  15

Ile Val Arg Ser Ser Pro Thr Pro Gly Ser Glu Gly His Ser Ala Ala
             20                  25                  30

Pro Asp Cys Pro Ser Cys Ala Leu Ala Ala Leu Pro Lys Asp Val Pro
         35                  40                  45

Asn Ser Gln Pro Glu Met Val Glu Ala Val Lys Lys His Ile Leu Asn
 50                  55                  60

Met Leu His Leu Lys Lys Arg Pro Asp Val Thr Gln Pro Val Pro Lys
 65                  70                  75                  80

Ala Ala Leu Leu Asn Ala Ile Arg Lys Leu His Val Gly Lys Val Gly
                 85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
            260                 265                 270

Gly Gly Gly Glu Gly Gly Ala Gly Ala Asp Glu Glu Lys Glu Gln Ser
        275                 280                 285

His Arg Pro Phe Leu Met Leu Gln Ala Arg Gln Ser Glu Asp His Pro
    290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
```

```
            325                 330                 335
Asp Trp Ile Ile Ala Pro Ser Gly Tyr His Ala Asn Tyr Cys Glu Gly
            340                 345                 350

Glu Cys Pro Ser His Ile Ala Gly Thr Ser Gly Ser Ser Leu Ser Phe
            355                 360                 365

His Ser Thr Val Ile Asn His Tyr Arg Met Arg Gly His Ser Pro Phe
        370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
            405                 410                 415

Asn Met Ile Val Glu Glu Cys Gly Cys Ser
            420                 425
```

<210> SEQ ID NO 2
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 2
gcgagggagc ggctgacatt                                              20

<210> SEQ ID NO 3
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 3
agcactggcc aacaccaggg                                              20

<210> SEQ ID NO 4
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 4
ggcctcttcc agaaactagg                                              20

<210> SEQ ID NO 5
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 5
ccacaggcca atagtttgtc                                              20

<210> SEQ ID NO 6
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 6
aagctgcctg cctgttgcca a                                            21

<210> SEQ ID NO 7
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 7
ggcgagctac tgcccatgct t                                               21

<210> SEQ ID NO 8
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 8
atggatgatt tcgcagcttt                                                 20

<210> SEQ ID NO 9
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 9
tggctttaca ccaacgaaaa                                                 20

<210> SEQ ID NO 10
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 10
actgaattca cccccactga                                                 20

<210> SEQ ID NO 11
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 11
cctccatgat gctgcttaca                                                 20

<210> SEQ ID NO 12
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 12
aattggtcca gccttggaat                                                 20

<210> SEQ ID NO 13
<211> LENGTH: 18
<212> TYPE: DNA
<213> ORGANISM: Artificial Sequence
<220> FEATURE:

<223> OTHER INFORMATION: A synthetic oligonucleotide

<400> SEQUENCE: 13
cgttgctcac agaccaca                                                 18

<210> SEQ ID NO 14
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 14
ctcgaggctt gccagaccgt                                               20

<210> SEQ ID NO 15
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 15
gcgggcttgt cgggatctca g                                             21

<210> SEQ ID NO 16
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 16
gccctcgcag gtcaagagca                                               20

<210> SEQ ID NO 17
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 17
ttgaacaagt tccgcagggt g                                             21

<210> SEQ ID NO 18
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 18
tggatgagaa cgccaatgtc                                               20

<210> SEQ ID NO 19
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 19
tgggttgacc catagcttct                                               20

-continued

```
<210> SEQ ID NO 20
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 20
aaaccagtgg cagatcaacc                                              20

<210> SEQ ID NO 21
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 21
gcccatgcca aagataatca cc                                           22

<210> SEQ ID NO 22
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 22
caatcaggtg gtggtgtcag                                              20

<210> SEQ ID NO 23
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 23
gctcctggac tgttttctgc                                              20

<210> SEQ ID NO 24
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 24
tggagacctt ccgacactcc t                                            21

<210> SEQ ID NO 25
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 25
cgttgtgtcc cttgttgtgc                                              20

<210> SEQ ID NO 26
<211> LENGTH: 20
<212> TYPE: DNA
<213> ORGANISM: Artificial Sequence
<220> FEATURE:
<223> OTHER INFORMATION: A synthetic oligonucleotide
```

```
<400> SEQUENCE: 26
ggcacacagg caagtttaca                                              20

<210> SEQ ID NO 27
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 27
ccagcaaaga agagcgagag                                              20

<210> SEQ ID NO 28
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 28
ttcctactgc ttccgtctat caaa                                         24

<210> SEQ ID NO 29
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 29
gtgcagaatc ccacagctca                                              20

<210> SEQ ID NO 30
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 30
ggacagagac gacaagcaca                                              20

<210> SEQ ID NO 31
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 31
tggtggggag aaggtcaat                                               19

<210> SEQ ID NO 32
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 32
acttggagct gggacagaga                                              20

<210> SEQ ID NO 33
<211> LENGTH: 20
```

```
<212> TYPE: DNA
<213> ORGANISM: Artificial Sequence
<220> FEATURE:
<223> OTHER INFORMATION: A synthetic oligonucleotide

<400> SEQUENCE: 33
catctgtgta gggcatgtgg                                               20

<210> SEQ ID NO 34
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 34
cgcatcccta agggaacga                                                19

<210> SEQ ID NO 35
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 35
ttccagacgg cctcatcct                                                19

<210> SEQ ID NO 36
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 36
tgtgcctgag aacaccagag                                               20

<210> SEQ ID NO 37
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 37
gcagaggagc caaatctacc                                               20

<210> SEQ ID NO 38
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 38
cttcatccaa tggactgcat aaat                                          24

<210> SEQ ID NO 39
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 39
```
tcccaagtat aacactctac acagacaa                                              28

<210> SEQ ID NO 40
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 40 ccttaccccca attcttgaag ca                                                   22

<210> SEQ ID NO 41
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 41
tccagatcag acagagcttt gtg                                                   23

<210> SEQ ID NO 42
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 42
gatctcatcc caaacttggc cg                                                    22

<210> SEQ ID NO 43
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 43
cataggctgt tgacagtcat aaata                                                 25

<210> SEQ ID NO 44
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 44
cactttgtcc acctttgatg                                                       20

<210> SEQ ID NO 45
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 45
gctgctttca ttgcttctg                                                        19

<210> SEQ ID NO 46
<211> LENGTH: 20
<212> TYPE: DNA
<213> ORGANISM: Artificial Sequence

```
<220> FEATURE:
<223> OTHER INFORMATION: A synthetic oligonucleotide

<400> SEQUENCE: 46
ctgaccattc cccaggtcta                                              20

<210> SEQ ID NO 47
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 47
atggcttctc atcgtctgct                                              20

<210> SEQ ID NO 48
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 48
gacaagtgag agagcaagtg                                              20

<210> SEQ ID NO 49
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 49
acagtagtgg aaaccggag                                               19

<210> SEQ ID NO 50
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 50
gaagatggtg atgggatttc                                              20

<210> SEQ ID NO 51
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 51
gaaggtgaag gtcggagtc                                               19

<210> SEQ ID NO 52
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 52
cgacttctca gaaggcagag agtg                                         24
```

```
<210> SEQ ID NO 53
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 53
cttcatgtag aggccgcagg catt                                              24

<210> SEQ ID NO 54
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 54
ccaagccggt cttccatact c                                                 21

<210> SEQ ID NO 55
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 55
tgggaggtgt gtcatagtcg t                                                 21

<210> SEQ ID NO 56
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 56
cttccttctt catgccag                                                     18

<210> SEQ ID NO 57
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 57
acacgtcccc atctgaag                                                     18

<210> SEQ ID NO 58
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 58
tttggaagct gctggggaag                                                   20

<210> SEQ ID NO 59
<211> LENGTH: 20
<212> TYPE: DNA
<213> ORGANISM: Artificial Sequence
<220> FEATURE:
<223> OTHER INFORMATION: A synthetic oligonucleotide
```

```
<400> SEQUENCE: 59
gatgggagga ggggagagga                                               20

<210> SEQ ID NO 60
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 60
agtttgtgcc agggttttg                                                20

<210> SEQ ID NO 61
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 61
acttcacctt ccctccaacc                                               20

<210> SEQ ID NO 62
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 62
gtccatcttt gcttctggaa a                                             21

<210> SEQ ID NO 63
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 63
tagccaggtt gcgaagaact                                               20

<210> SEQ ID NO 64
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 64
tcgctacagc ctttgcaatg                                               20

<210> SEQ ID NO 65
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 65
ttgagggtac ggaggagttc c                                             21

<210> SEQ ID NO 66
```

```
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 66
ggcgcagcag aatccaga                                                 18

<210> SEQ ID NO 67
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 67
ccacgacttg cccagcat                                                 18

<210> SEQ ID NO 68
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 68
gcctcccagc aacgtgcttt g                                             21

<210> SEQ ID NO 69
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 69
ctcctggatc cggctgcacg                                               20

<210> SEQ ID NO 70
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 70
tccgggtgcg gcgctgag                                                 18

<210> SEQ ID NO 71
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 71
ggcgagcctc atcctccggg                                               20
```